(12) United States Patent
Karsenty et al.

(10) Patent No.: US 8,614,222 B2
(45) Date of Patent: Dec. 24, 2013

(54) METHODS OF PREVENTING AND TREATING LOW BONE MASS DISEASES

(75) Inventors: Gerard Karsenty, New York, NY (US); Patricia F. Ducy, New York, NY (US); Vijay Kumar Yadav, Cambridge (GB); Donald Landry, New York, NY (US); Shi-Xian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/128,987

(22) PCT Filed: Nov. 13, 2009

(86) PCT No.: PCT/US2009/064383
§ 371 (c)(1),
(2), (4) Date: Aug. 2, 2011

(87) PCT Pub. No.: WO2010/056992
PCT Pub. Date: May 20, 2010

(65) Prior Publication Data
US 2011/0281899 A1 Nov. 17, 2011

Related U.S. Application Data

(60) Provisional application No. 61/114,256, filed on Nov. 13, 2008, provisional application No. 61/244,656, filed on Sep. 22, 2009, provisional application No. 61/244,648, filed on Sep. 22, 2009, provisional application No. 61/244,661, filed on Sep. 22, 2009.

(51) Int. Cl.
*A61K 31/505* (2006.01)
*C07D 239/47* (2006.01)

(52) U.S. Cl.
USPC ............................................ 514/272; 544/297

(58) Field of Classification Search
None
See application file for complete search history.

(56) References Cited

U.S. PATENT DOCUMENTS

| 6,403,651 | B1 | 6/2002 | Kennaway |
| 2004/0127573 | A1 | 7/2004 | Stashenko et al. |
| 2006/0165683 | A1 | 7/2006 | Karsenty et al. |
| 2007/0191344 | A1 | 8/2007 | Choidas et al. |
| 2008/0032959 | A1 | 2/2008 | Alves et al. |
| 2008/0153852 | A1 | 6/2008 | Devasagayaraj et al. |

OTHER PUBLICATIONS

Hobar, Coburn, MD. "Prevention of Osteoporosis." eMedicineHealth: Practical Guide to Health. (2005). Accessed May 19, 2009. <http://www.emedicinehealth.com/prevention_of_osteoporosis/article_em.htm>.*
Andersen et al.; J. Med. Chem. 2002, 45, pp. 4443-4459.*
Liu, Q. et al., "Discovery and Characterization of Novel Tryptophan Hydroxylase Inhibitors that Selectively Inhibit Serotonin Synthesis in the Gastrointestinal Tract", JPET (2008), vol. 325:1, pp. 47-55.
Yadav, V. K. et al., "Lrp5 controls bone formation by inhibiting serotonin synthesis in the duodenum", Cell (2008), vol. 135, pp. 825-837.

* cited by examiner

*Primary Examiner* — Alicia L Otton
(74) *Attorney, Agent, or Firm* — Kenyon & Kenyon LLP

(57) ABSTRACT

The present invention provides methods and therapeutic agents for lowering or increasing serum serotonin levels in a patient in order to increase or decrease bone mass, respectively. In preferred embodiments, the patient is known to have, or to be at risk for, a low bone mass disease such as osteoporosis and the agents are TPH1 inhibitors or serotonin receptor antagonists.

4 Claims, 22 Drawing Sheets

WT                    Lrp5 Act Duo

| | Sham | OVX (Veh) | OVX (LP250) |
|---|---|---|---|
| BV/TV (%) | 18.1 ± 1.0 [a] | 11.1 ± 0.9 [b] | 18.9 ± 0.9 [a] |
| Nb.Ob/T.Ar. (mm⁻¹) | 97.7 ± 29.1 [a] | 136.3 ± 21.6 [b] | 188.2 ± 20.9 [c] |
| BFR (μm³/μm²/Year) | 101.2 ± 10.9 [a] | 132.1 ± 11.2 [b] | 210.9 ± 21.9 [c] |
| OcS/BS | 9.3 ± 1.8 [a] | 14.1 ± 1.9 [b] | 14.9 ± 1.6 [b] |
| Serum Serotonin (ng/ml) | 357.8 ± 39.5 [a] | 386.5 ± 26.2 [a] | 39.4 ± 20.1 [b] |

FIGURE 19

|  |  | Sham | OVX (Veh) | OVX (LP25) | OVX (LP100) | OVX (LP250) |
|---|---|---|---|---|---|---|
| Vertebrae | BV/TV (%) | 12.0 ± 0.6[a] | 8.9 ± 0.8[b] | 13.3 ± 0.4[a] | 15.3 ± 0.4[c] | 16.7 ± 0.6[d] |
| | Nb.Ob/T.Ar. (mm⁻¹) | 42.2 ± 11.2[a] | 58.2 ± 8.7[a] | 125.3 ± 17.9[b] | 153.0 ± 8.8[c] | 175.1 ± 36.4[c] |
| | BFR (μm³/μm²/Year) | 91.6 ± 7.2[a] | 122.3 ± 11.8[b] | 135.7 ± 11.9[b,c] | 152.1 ± 13.4[c] | 191.9 ± 17.3[d] |
| | OcS/BS | 22.6 ± 4.6[a] | 38.7 ± 7.4[b] | 32.8 ± 4.8[b] | 34.4 ± 3.8[b] | 31.2 ± 2.7[b] |
| Femurs | BV/TV (%) | 10.9 ± 0.7[a] | 4.9 ± 0.8[b] | 7.7 ± 0.3[c] | 9.0 ± 0.9[a,c] | 9.2 ± 1.0[a,c] |
| | Nb.Ob/T.Ar. (mm⁻¹) | 262.8 ± 37.1[a] | 323.3 ± 25.7[b] | 544.0 ± 14.8[c] | 611.8 ± 42.8[c] | 791.0 ± 35.6[d] |
| | BFR (μm³/μm²/Year) | 149.2 ± 47.1[a] | 186.2 ± 22.8[b] | 395.7 ± 18.8[c] | 347.2 ± 54.5[c] | 448.9 ± 40.3[d] |
| | OcS/BS | 23.9 ± 1.4[a] | 34.3 ± 3.1[b] | 33.3 ± 2.6[b] | 35.7 ± 1.8[b] | 32.1 ± 1.1[b] |
| Serum Serotonin (ng/ml) | | 336.4 ± 26.7[a] | 342.3 ± 36.7[a] | 203.0 ± 23.4[b] | 139.8 ± 21.6[c] | 62.9 ± 10.1[d] |
| Plasma Serotonin (ng/ml) | | 16.8 ± 1.2[a] | 18.2 ± 3.5[a] | 11.8 ± 2.1[b] | 9.9 ± 1.5[b,c] | 8.1 ± 1.4[c] |

METHODS OF PREVENTING AND TREATING LOW BONE MASS DISEASES

CROSS REFERENCE TO RELATED APPLICATION

This application is a 371 of International Patent Application No. PCT/US2009/064383, filed Nov. 13, 2009; which claims priority from U.S. Provisional Patent Application Ser. No. 61/114,256, filed Nov. 13, 2008; U.S. Provisional Patent Application Ser. No. 61/244,648, filed Sep. 22, 2009; U.S. Provisional Patent Application Ser. No. 61/244,656, filed Sep. 22, 2009; and U.S. Provisional Patent Application Ser. No. 61/244,661, filed Sep. 22, 2009; the contents of which applications are hereby incorporated by reference in their entireties.

FIELD OF THE INVENTION

The invention is in the field of prevention and therapy of diseases or disorders mediated by peripheral serotonin, e.g., diseases associated with lower than normal bone mass such as osteoporosis.

BACKGROUND OF THE INVENTION

Bone remodeling, the mechanism whereby vertebrates renew bone tissues throughout adulthood, comprises two phases: resorption of preexisting mineralized bone matrix by a specialized cell type, the osteoclast, followed by de novo bone formation by another specialized cell type, the osteoblast. Genetic and molecular studies have shown that local effectors (cytokines and growth factors) and systemic effectors (hormones and neuromediators) modulate both phases of bone remodeling.

One of the most intensively studied genes regulating bone remodeling is LDL-receptor related protein 5 (LRP5). Loss-of-function mutations in LRP5 result in osteoporosis pseudoglioma (OPPG), a disease characterized by severe bone loss due to a decrease in bone formation and by the persistence of embryonic vascularization of the eyes, causing blindness. By contrast, gain-of-function mutations in LRP5 cause another bone disease, high bone mass syndrome. The involvement of Lrp5 in two human diseases of opposite nature underscores the importance of the pathways controlled by this gene in the regulation of bone formation. However, the mechanism by which LRP5 affects bone development is not known.

Mice genetically deficient for the TPH 1 gene ("knockout mice") have been reported. In one case, the mice reportedly expressed normal amounts of serotonin in classical serotonergic brain regions, but largely lacked serotonin in the periphery. In another, the knockout mice exhibited abnormal cardiac activity, which was attributed to a lack of peripheral serotonin (Côté et al., 2003, Proc. Natl. Acad. Sci. USA 100:13525-13530).

International Patent Application No. PCT/US2009/038817, published as WO 2009/123978, the disclosure of which is incorporated herein in its entirety, is directed to methods of diagnosing, preventing, and treating bone mass diseases using therapeutic agents for lowering or increasing serum serotonin levels.

SUMMARY OF THE INVENTION

The present invention provides compounds that are inhibitors of tryptophan hydroxylase 1 (TPH1), the enzyme responsible for the first step of serotonin synthesis in enterochromaffin cells of the duodenum, as well as pharmaceutical compositions comprising the compounds. The compounds and pharmaceutical compositions comprising the compounds are useful for the treatment and/or prevention of conditions where it is beneficial to inhibit TPH1 and thus lower serum serotonin levels.

It has been discovered that elevated levels of serum serotonin due to overexpression of tryptophan hydroxylase 1 (TPH1), the enzyme responsible for the first step of serotonin synthesis in enterochromaffin cells of the duodenum, and possibly in osteoblasts, causes decreased bone mass in LRP5 loss of function mutants. Thus, certain embodiments of the invention are directed to methods for treating or preventing low bone mass diseases such as osteoporosis and OPPG by administering a therapeutic agent that inhibits serotonin synthesis or inhibits TPH1, the enzyme necessary for serotonin synthesis in duodenum, or by administering antagonists of the serotonin receptor HT1B, the receptor mediating the effect of serotonin on osteoblasts.

Certain other embodiments of the invention are directed to pharmaceutical compositions for increasing bone mass that include therapeutic agents that decrease serum serotonin levels, including one or more TPH1 inhibitors, optionally together with one or more serotonin receptor antagonists, for use in treating or preventing low bone mass diseases. In some embodiments, the present invention includes a pharmaceutical composition for treating or preventing anxiety or depression where the pharmaceutical composition includes both a selective serotonin reuptake inhibitor (SSRI) and a drug that reduces the level of serum serotonin, in order to prevent patients treated with serotonin reuptake inhibitors from developing osteoporosis or to treat osteoporosis in patients taking SSRIs.

In other embodiments, the present invention provides methods of treating patients for anxiety or depression where an SSRI and a drug that reduces the level of serum serotonin are administered to a patient via separate pharmaceutical compositions.

U.S. Provisional Patent Application Ser. No. 60/976,403, filed Sep. 28, 2007, and International Patent Application PCT/US08/77870, filed Sep. 26, 2008 and published Apr. 9, 2009 as WO 2009/045900, incorporated by reference herein in their entireties, disclose that brain-derived serotonin (hereafter abbreviated BDS) has the opposite effect of peripheral serotonin. Elevated BDS increases bone mass by acting through HT2C receptors on target neurons in the hypothalamus. Thus, some embodiments of the present invention include administering a combination of therapeutic agents that includes agents that decrease peripheral serotonin and agents that increase BDS. BDS can be increased by increasing the activity of tryptophan hydroxylase 2 (TPH2), the enzyme responsible for the first step of serotonin synthesis in neurons of the brain stem, and by administering agonists of the HT2C serotonin receptor in the brain.

Other methods disclosed herein are directed to diagnosing a person at risk of developing a low bone mass disease such as osteoporosis by determining if the serum level of serotonin in the periphery is abnormally high (about 25% or more) compared to normal individuals, taking into account the age, gender, or other factors that affect serum serotonin levels. Such a person at risk may be treated with therapeutic agents that decrease serum serotonin to prevent the low bone mass disease from developing. Those of skill in the art will understand that serum serotonin levels may vary among individuals depending on certain factors and will be able to take those factors into account to determine whether a person has abnormally high serum serotonin levels. One possible range which those skilled in the art may consider to be normal serum serotonin levels is 101-283 ng/ml (nanograms per milliliter).

Since elevated serum serotonin may not be the only cause of diseases associated with low bone mass, methods other than those measuring serum serotonin levels may also be used to determine if a person having a low bone mass disease such as osteoporosis should be treated with drugs that decrease serum serotonin.

The present invention provides a method of lowering serum serotonin levels in a patient known or suspected to be in need of lowering of serum serotonin levels comprising administering to the patient known or suspected to be in need of lowering of serum serotonin levels a TPH1 inhibitor or a serotonin receptor antagonist.

The present invention also provides a method of treating or preventing a low bone mass disease in a patient known or suspected to be in need of such treatment or prevention comprising administering to the patient known or suspected to be in need of such treatment or prevention a therapeutically effective amount of an agent that lowers the level of serum serotonin.

In preferred embodiments, the agent is a TPH1 inhibitor that does not cross the blood brain barrier. In other embodiments, the agent is a TPH1 inhibitor that does not significantly inhibit TPH2.

In certain embodiments, the agent is one or more TPH1 inhibitors selected from the following or from pharmaceutically acceptable salts and solvates thereof:

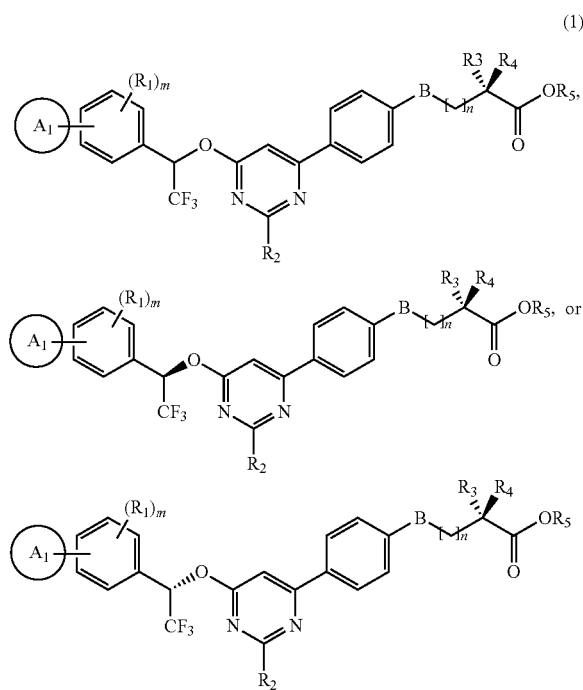

where $A_1$ is optionally substituted heterocycle or 3-fluorophenyl; B is O, N, or —$CH_2$—; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is halogen, hydrogen, $C(O)R_A$, $OR_A$, $NR_BR_C$, $S(O_2)R_A$, or optionally substituted alkyl, alkyl-aryl or alkyl-heterocycle; either $R_3$ is $NHR_6$ and $R_4$ is hydrogen or, alternatively, $R_3$ and $R_4$ together form =O; $R_5$ is hydrogen or optionally substituted alkyl, alkyl-aryl, alkyl-heterocycle, aryl, or heterocycle; $R_6$ is hydrogen, $C(O)R_A$, $C(O)OR_A$, or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 0-4; and n is 0 or 1.

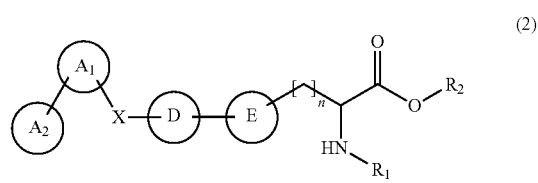

where each of $A_1$ and $A_2$ is independently a monocyclic optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and n is 0-3.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

Particular compounds include those wherein $R_1$ is hydrogen or optionally substituted alkyl.

In some compounds, $R_2$ is hydrogen or optionally substituted alkyl.

In some compounds, n is 1 or 2.

In some compounds, X is a bond or S. In others, X is —C($R_4$)=, =C($R_4$)—, —C($R_3R_4$)—, —C($R_4$)=C($R_4$)—, or —C≡C—, and, for example, $R_4$ is independently hydrogen or optionally substituted alkyl. In others, X is —O—, —C($R_3R_4$)O—, or —OC($R_3R_4$)—, and, for example, $R_3$ is hydrogen or optionally substituted alkyl, and $R_4$ is hydrogen or optionally substituted alkyl. In some, $R_3$ is hydrogen and $R_4$ is trifluoromethyl. In some compounds, X is —S($O_2$)—, —S($O_2$)N($R_5$)—, —N($R_5$)S($O_2$)—, —C($R_3R_4$)S($O_2$)—, or —S($O_2$)C($R_3R_4$)—, and, for example, $R_3$ is hydrogen or optionally substituted alkyl, $R_4$ is hydrogen or optionally substituted alkyl, and $R_5$ is hydrogen or optionally substituted alkyl. In others, X is —N($R_5$)—, —N($R_5$)C(O)N($R_5$)—, —C($R_3R_4$)N($R_5$)—, or —N($R_5$)C($R_3R_4$)—, and, for example, $R_3$ is hydrogen or optionally substituted alkyl, $R_4$ is hydrogen or optionally substituted alkyl, and each $R_5$ is independently hydrogen or optionally substituted alkyl.

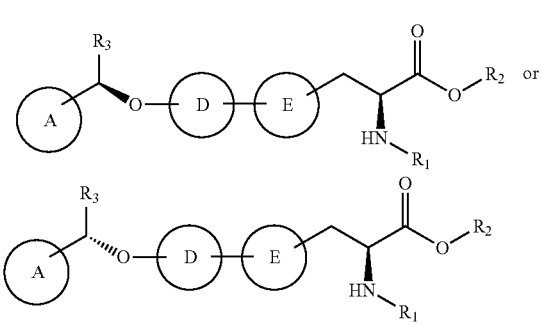

(3)

where A is optionally substituted cycloalkyl, aryl, or heterocycle; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; and $R_3$ is trifluoromethyl.

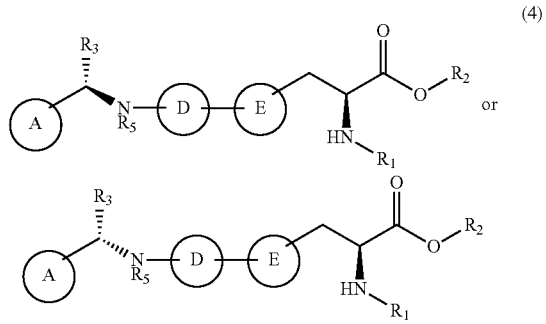

(4)

where A is optionally substituted cycloalkyl, aryl, or heterocycle; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; and $R_5$ is hydrogen or optionally substituted alkyl or aryl.

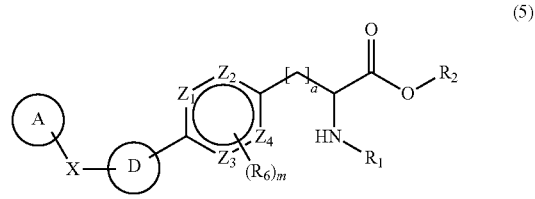

(5)

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z_1$, $Z_2$, $Z_3$, and $Z_4$ is independently N or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; m is 1-4; and n is 1-3.

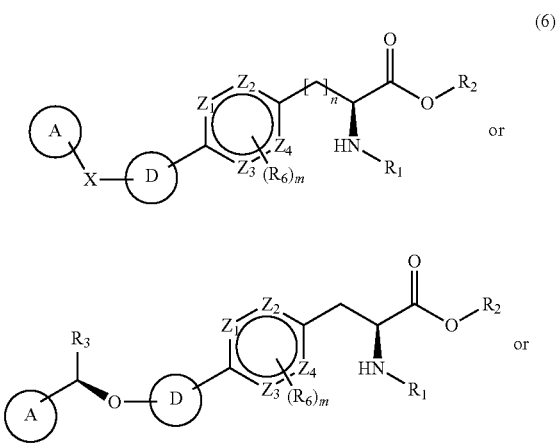

(6)

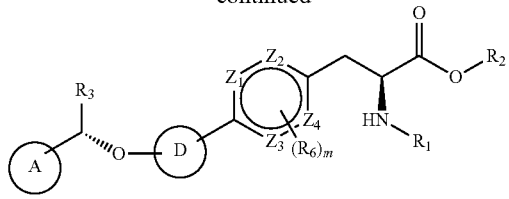

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; each of Z$_1$, Z$_2$, Z$_3$, and Z$_4$ is independently N or CR$_6$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; R$_3$ is trifluoromethyl; each R$_4$ is independently hydrogen, alkoxy, amino, cyano, halogen, hydroxyl, or optionally substituted alkyl or aryl; each R$_5$ is independently hydrogen or optionally substituted alkyl or aryl; each R$_6$ is independently hydrogen, cyano, halogen, OR$_7$, NR$_8$R$_9$, amino, hydroxyl, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; m is 1-4; and n is 1-3.

(7)

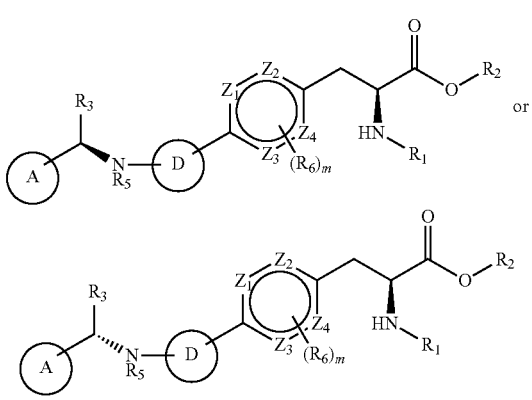

where A is optionally substituted cycloalkyl, aryl, or heterocycle; D is optionally substituted aryl or heterocycle; each of Z$_1$, Z$_2$, Z$_3$, and Z$_4$ is independently N or CR$_6$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; R$_3$ is hydrogen; R$_5$ is hydrogen or optionally substituted alkyl or aryl; each R$_6$ is independently hydrogen, cyano, halogen, OR$_7$, NR$_8$R$_9$, amino, hydroxyl, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; and m is 1-4.

Some compounds are such that all of Z$_1$, Z$_2$, Z$_3$, and Z$_4$ are N. In others, only three of Z$_1$, Z$_2$, Z$_3$, and Z$_4$ are N. In others, only two of Z$_1$, Z$_2$, Z$_3$, and Z$_4$ are N. In others, only one of Z$_1$, Z$_2$, Z$_3$, and Z$_4$ is N. In others, none of Z$_1$, Z$_2$, Z$_3$, and Z$_4$ are N.

(8)

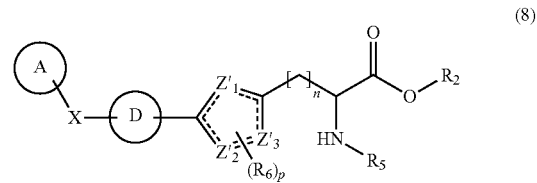

where A is optionally substituted cycloalkyl, aryl, or heterocycle; X is a bond (i.e., A is directly bound to D), —O—, —S—, —C(O)—, —C(R$_4$)=, —C(R$_4$)—, —C(R$_3$R$_4$)—, —C(R$_4$)=C(R$_4$)—, —C≡C—, N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; each of Z'$_1$, Z'$_2$, and Z'$_3$, is independently N, NH, S, O or CR$_6$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; each R$_3$ is independently hydrogen, alkoxy, amino, cyano, halogen, hydroxyl, or optionally substituted alkyl; each R$_4$ is independently hydrogen, alkoxy, amino, cyano, halogen, hydroxyl, or optionally substituted alkyl or aryl; each R$_5$ is independently hydrogen or optionally substituted alkyl or aryl; each R$_6$ is independently amino, cyano, halogen, hydrogen, OR$_7$, SR$_7$, NR$_8$R$_9$, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; n is 1-3; and p is 1-3.

(9)

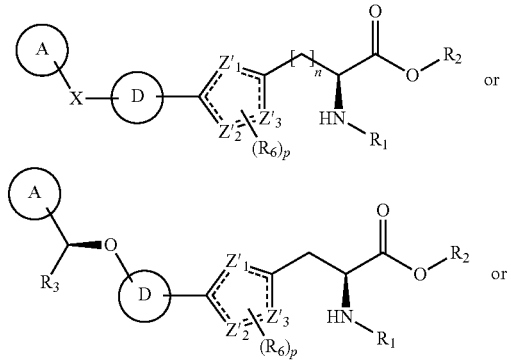

-continued

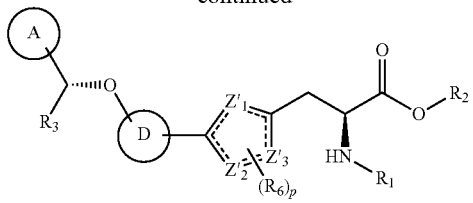

where A is optionally substituted cycloalkyl, aryl, or heterocycle; X is a bond (i.e., A is directly bound to D), —O—, —S—, —C(O)—, —C(R$_4$)═, ═C(R$_4$)—, —C(R$_3$R$_4$)—, —C(R$_4$)═C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; each of Z'$_1$, Z'$_2$, and Z'$_3$, is independently N, NH, S, O or CR$_6$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; each R$_3$ is independently hydrogen, alkoxy, amino, cyano, halogen, hydroxyl, or optionally substituted alkyl or aryl; each R$_4$ is independently hydrogen, alkoxy, amino, cyano, halogen, hydroxyl, or optionally substituted alkyl or aryl; each R$_5$ is independently hydrogen or optionally substituted alkyl or aryl; each R$_6$ is independently amino, cyano, halogen, hydrogen, OR$_7$, SR$_7$, NR$_8$R$_9$, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; n is 1-3; and p is 1-3.

(10)

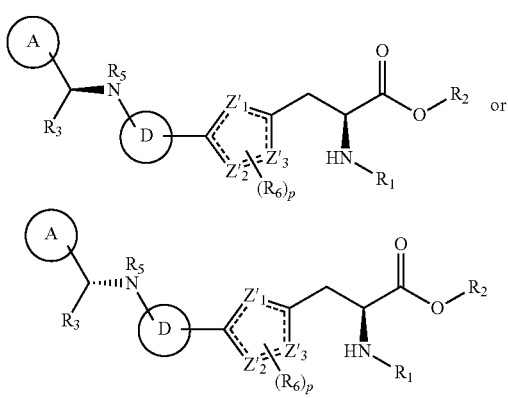

where A is optionally substituted cycloalkyl, aryl, or heterocycle; D is optionally substituted aryl or heterocycle; each of Z'$_1$, Z'$_2$, and Z'$_3$, is independently N, NH, S, O or CR$_6$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; R$_3$ is hydrogen; R$_5$ is hydrogen or optionally substituted alkyl or aryl; each R$_6$ is independently amino, cyano, halogen, hydrogen, OR$_7$, SR$_7$, NR$_8$R$_9$, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; and p is 1-3.

Some compounds are such that all of Z'$_1$, Z'$_2$, and Z'$_3$ are N or NH. In others, only two of Z'$_1$, Z'$_2$, and Z'$_3$ are N or NH. In others, only one of Z'$_1$, Z'$_2$, and Z'$_3$ is N or NH. In others, none of Z'$_1$, Z'$_2$, and Z'$_3$ are N or NH.

(11)

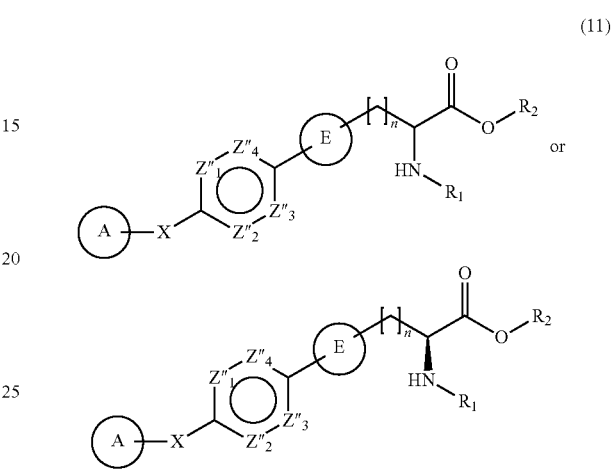

where A is optionally substituted cycloalkyl, aryl, or heterocycle; E is optionally substituted aryl or heterocycle; X is a bond, —O—, —S—, —C(O)—, —C(R$_4$)═, ═C(R$_4$)—, —C(R$_3$R$_4$)—, —C(R$_4$)═C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; each of Z''$_1$, Z''$_2$, Z''$_3$, and Z''$_4$ is independently N or CR$_{10}$; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; each R$_3$ is independently hydrogen, alkoxy, amino, cyano, halogen, hydroxyl, or optionally substituted alkyl; each R$_4$ is independently hydrogen, alkoxy, amino, cyano, halogen, hydroxyl, or optionally substituted alkyl or aryl; each R$_5$ is independently hydrogen or optionally substituted alkyl or aryl; each R$_{10}$ is independently amino, cyano, halogen, hydrogen, OR$_{11}$, SR$_{11}$, NR$_{12}$R$_{13}$, or optionally substituted alkyl, alkyl-aryl or alkyl-heterocycle; each R$_{11}$ is independently hydrogen or optionally substituted alkyl, alkyl-aryl or alkyl-heterocycle; each R$_{12}$ is independently hydrogen or optionally substituted alkyl, alkyl-aryl or alkyl-heterocycle; each R$_{13}$ is independently hydrogen or optionally substituted alkyl, alkyl-aryl or alkyl-heterocycle; and n is 1-3.

(12)

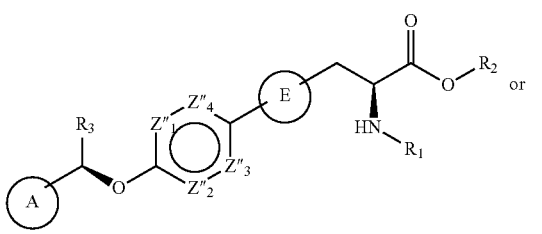

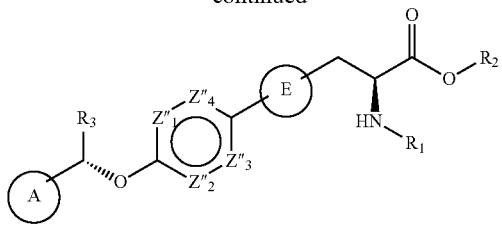

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is trifluoromethyl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

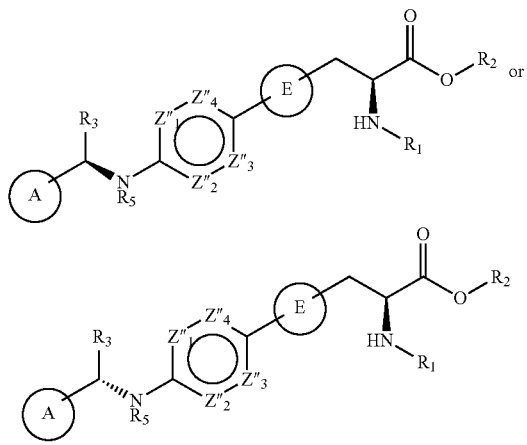

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

Some compounds are such that all of $Z''_1$, $Z''_2$, $Z''_3$, and $Z''_4$ are N. In others, only three of $Z''_1$, $Z''_2$, $Z''_3$, and $Z''_4$ are N. In others, only two of $Z''_1$, $Z''_2$, $Z''_3$, and $Z''_4$ are N. In others, only one of $Z''_1$, $Z''_2$, $Z''_3$, and $Z''_4$ is N. In others, none of $Z''_1$, $Z''_2$, $Z''_3$, and $Z''_4$ are N.

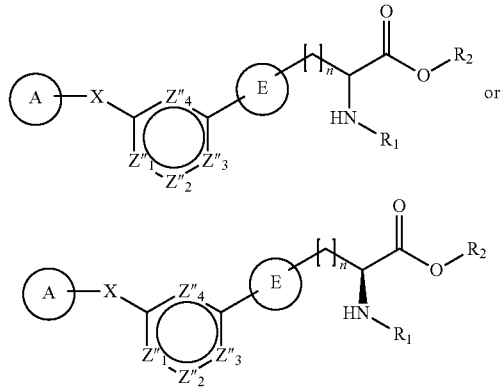

where A is optionally substituted cycloalkyl, aryl, or heterocycle; E is optionally substituted aryl or heterocycle; X is a bond, —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; each $R_{13}$ is independently hydrogen or optionally substituted alkyl, alkyl-aryl or alkyl-heterocycle; and n is 1-3.

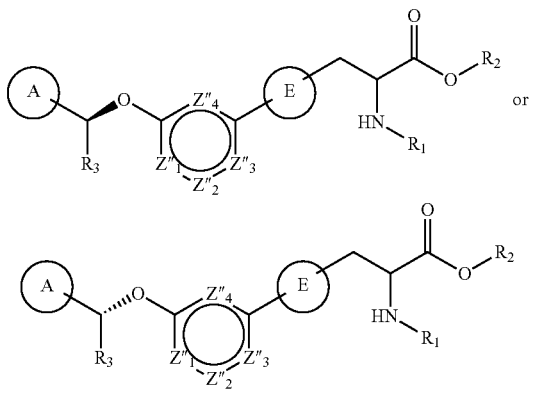

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is trifluoromethyl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

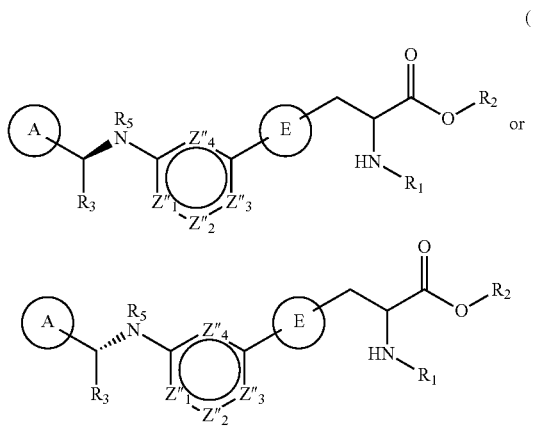

(16)

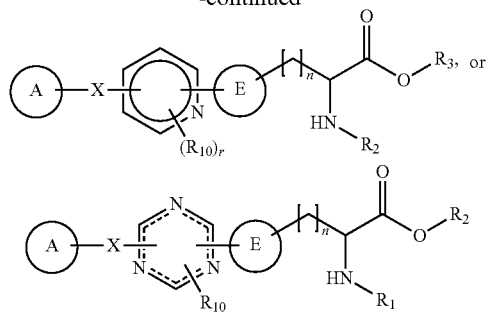

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

Some compounds are such that all of $Z''_1$, $Z''_2$, $Z''_3$, and $Z''_4$ are N. In others, only three of $Z''_1$, $Z''_2$, $Z''_3$, and $Z''$ are N. In others, only two of $Z''_1$, $Z''_2$, $Z''_3$, and $Z''_4$ are N. In others, only one of $Z''_1$, $Z''_2$, $Z''_3$, and $Z''_4$ is N. In others, none of $Z''_1$, $Z''_2$, $Z''_3$, and $Z''_4$ are N.

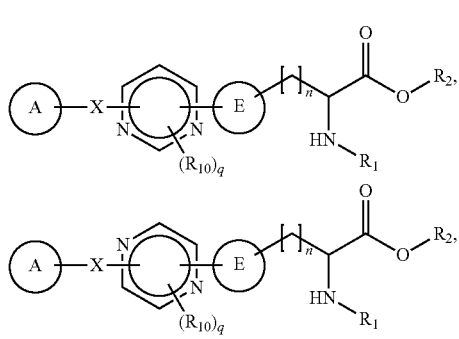

(17)

where A is optionally substituted cycloalkyl, aryl, or heterocycle; E is optionally substituted aryl or heterocycle; X is a bond, —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; each $R_{13}$ is independently hydrogen or optionally substituted alkyl, alkyl-aryl or alkyl-heterocycle; n is 1-3; q is 0-2; and r is 0-2.

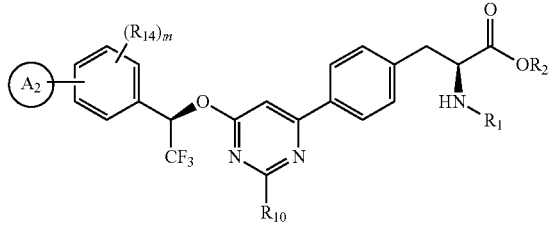

(18)

where $A_2$ is optionally substituted cycloalkyl, aryl, or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_{10}$ is amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; $R_{12}$ is hydrogen or optionally substituted alkyl, alkyl-aryl or alkyl-heterocycle; $R_{13}$ is hydrogen or optionally substituted alkyl, alkyl-aryl or alkyl-heterocycle; each $R_{14}$ is independently amino, halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

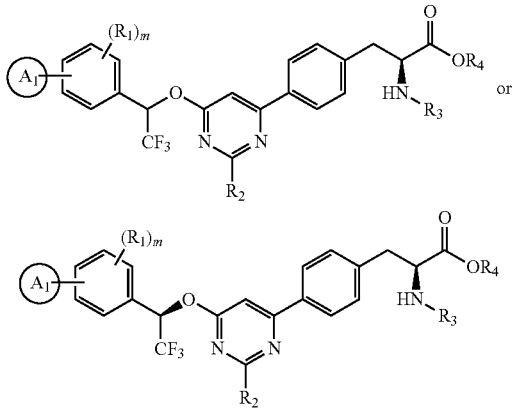

(19)

where $A_1$ is optionally substituted heterocycle; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

(20)

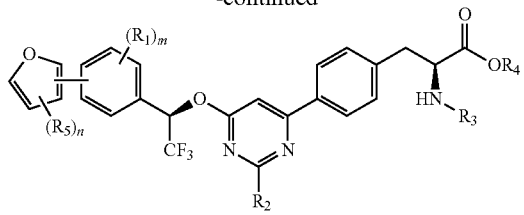

-continued where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and n is 1-3.

(21)

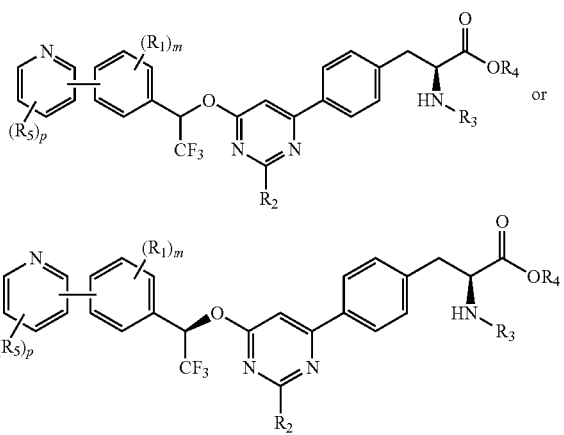

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and p is 1-3.

(22)

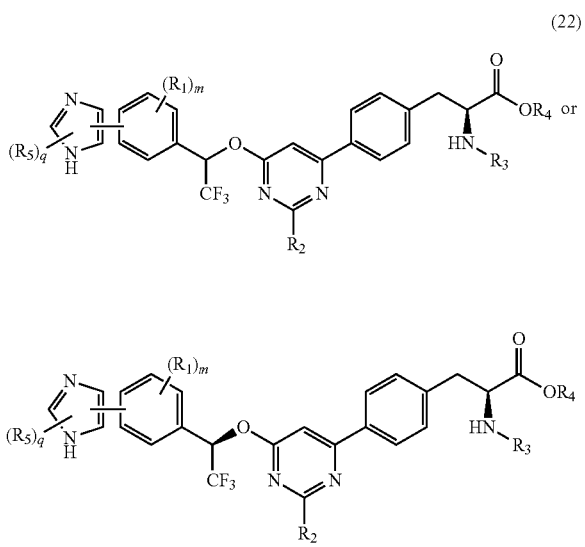

(23)

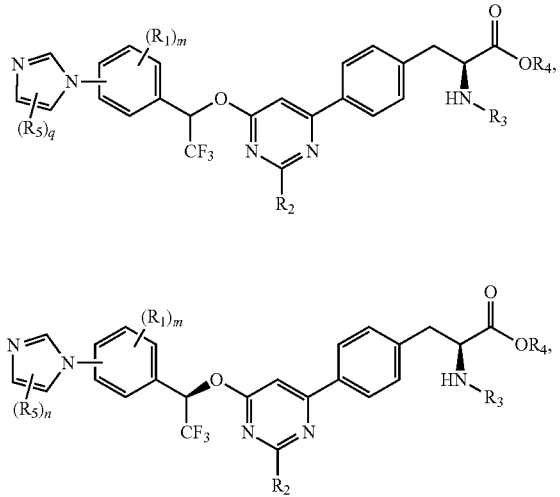

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and q is 1-2.

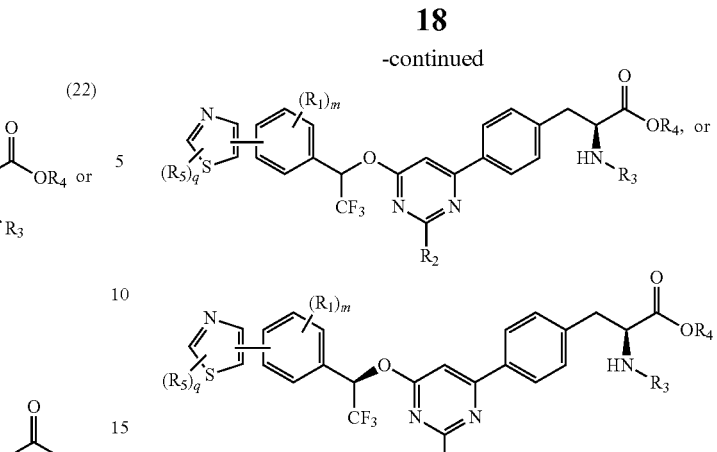

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-1-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$, is independently hydrogen or optionally substituted alkyl, alkyl-aryl or alkyl-heterocycle; m is 1-4; n is 1-3; and q is 1-2.

In particular compounds above, $A_1$ is aromatic. In others, $A_1$ is not aromatic. In some, $A_1$ is optionally substituted with one or more of halogen or lower alkyl.

In some, $R_1$ is hydrogen or halogen.

In some, m is 1.

In some, $R_2$ is hydrogen or amino.

In some, $R_3$ is hydrogen or lower alkyl. In others, $R_3$ is $C(O)OR_A$ and $R_A$ is alkyl.

In some, $R_4$ is hydrogen or lower alkyl.

In some, $R_5$ is hydrogen or lower alkyl (e.g., methyl).

In some, n is 1.

In some, p is 1.

In some, q is 1.

(24)

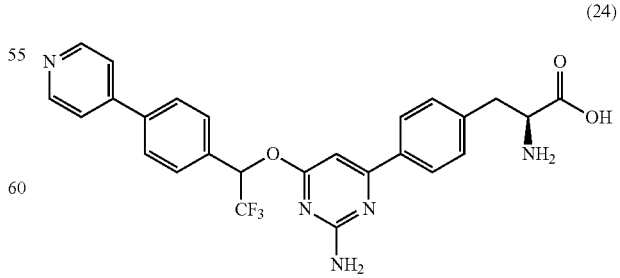

(S)-2-Amino-3-(4-{2-amino-6-[2,2,2-trifluoro-1-(4-pyridin-4-yl-phenyl)-ethoxy]-pyrimidin-4-yl}-phenyl)-propionic acid

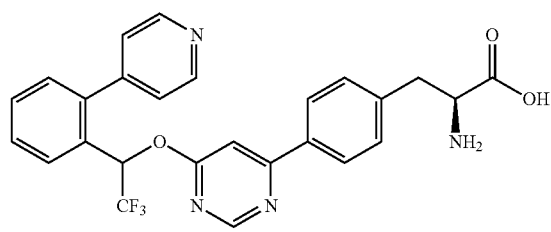

(25)

(S)-2-Amino-3-(4-{6-[2,2,2-trifluoro-1-(2-pyridin-4-yl-phenyl)-ethoxy]-pyrimidin-4-yl}-phenyl)-propionic acid

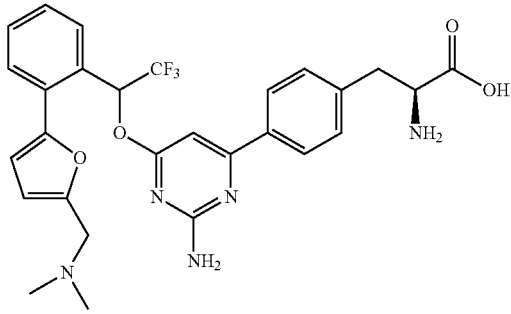

(29)

(S)-2-Amino-3-[4-{2-amino-6-{1-[2-(5-dimethylaminomethyl-furan-2-yl)-phenyl]-2,2,2-trifluoro-ethoxy}-pyrimidin-4-yl)-phenyl]-propionic acid

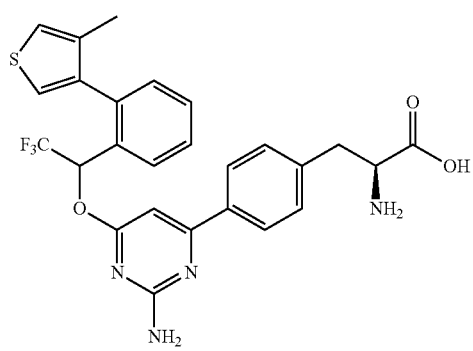

(26)

(S)-2-Amino-3-(4-{2-amino-6-[2,2,2-trifluoro-1-(2-(4-methylthiophen-3-yl)-phenyl]-ethoxy}-pyrimidin-4-yl)-phenyl]-propionic acid

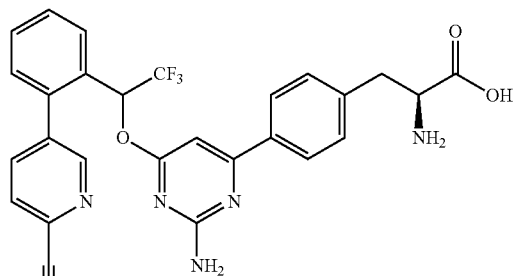

(30)

(S)-2-Amino-3[4-(2-amino-6-{1-[2-(6-cyano-pyridin-3-yl)-phenyl]-2,2,2-tri-fluoro-ethoxy}-pyrimidin-4-yl)-phenyl]-propionic acid

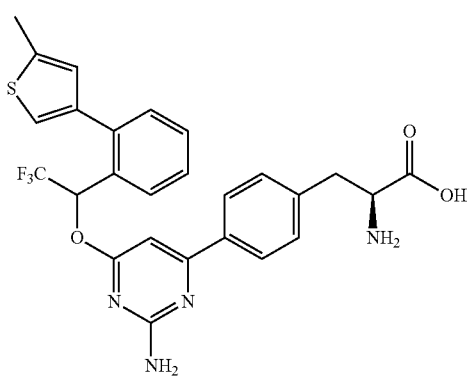

(27)

(S)-2-Amino-3-(4-{2-amino-6-[2,2,2-trifluoro-1-(2-(4-methylthiophen-3-yl)-phenyl]-ethoxy}-pyrimidin-4-yl)-phenyl]-propionic acid

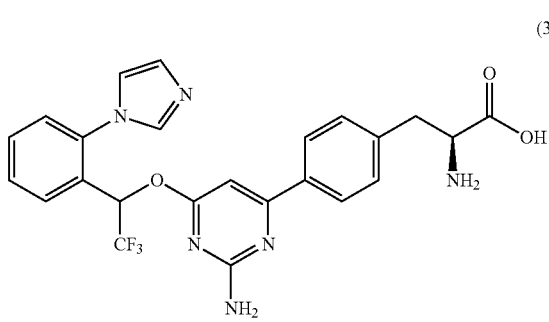

(31)

(S)-2-Amino-3-(4-{2-amino-6-[2,2,2-trifluoro-1-(2-imidazol-1-yl-phenyl)-ethoxy]-pyrimidin-4-yl}-phenyl)-propionic acid

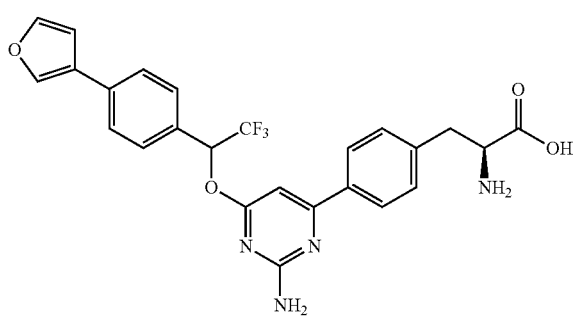

(28)

(S)-2-Amino-3-(4-{2-amino-6-[2,2,2-trifluoro-1-(4-furan-3-yl-phenyl)-ethoxy]-pyrimidin-4-yl}-phenyl)-propionic acid

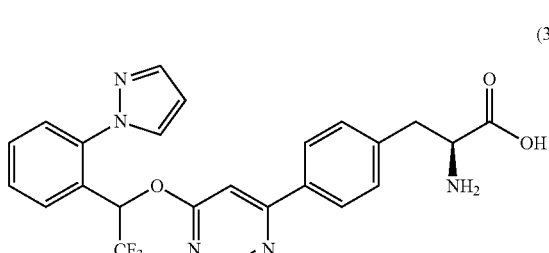

(32)

(S)-2-Amino-3-(4-{6-[2,2,2-trifluoro-1-(2-pyrazol-1-yl-phenyl)-ethoxy]-pyrimidin-4-yl}-phenyl)-propionic acid (33)

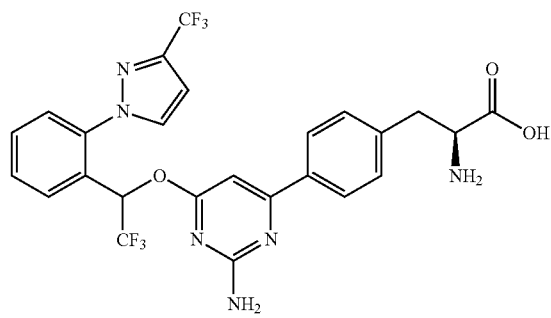

(S)-2-amino-3-[4-(2-amino-6-{2,2,2-trifluoro-1-[2-(3-trifluoromethyl-pyrazol-1-yl)-phenyl]-ethoxy}-pyrimidin-4-yl)-phenyl]-propionic acid (34)

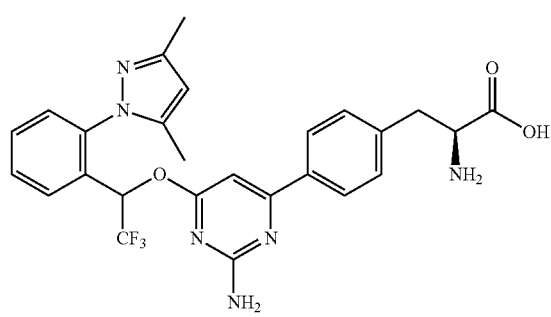

(S)-2-Amino-3-[4-(2-amino-6-{1-[2-(3,5-dimethyl-pyrazol-1-yl)-phenyl]-2,2,2-trifluoro-ethoxy}-pyrimidin-4-yl)-phenyl]-propionic acid (35)

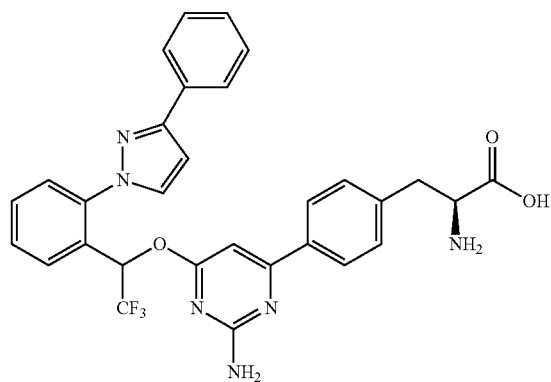

(S)-2-Amino-3-[4-(2-amino-6-{2,2,2-trifluoro-1-[2-(3-phenyl-pyrazol-1-yl)-phenyl]-ethoxy}-pyrimidin-4-yl)-phenyl]-propionic acid (36)

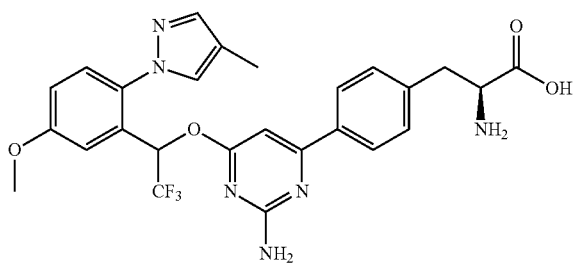

(S)-2-Amino-3-[4-(2-amino-6-{2,2,2-trifluoro-1-[5-methyl-pyrazol-1-yl)-phenyl]-ethoxy}-pyrimidin-4-yl)-phenyl]-propionic acid (37)

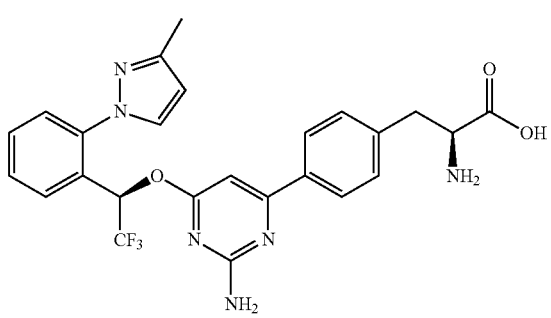

(S)-2-amino-3-[4-(2-amino-6-{(R)-2,2,2-trifluoro-1-[2-(3-methyl-pyrazol-1-yl)-phenyl]-ethoxy}-pyrimidin-4-yl)-phenyl]-propionic acid (38)

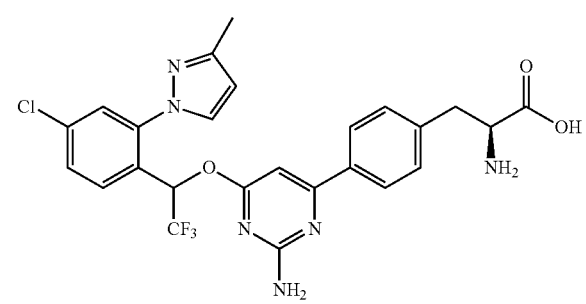

(S)-2-amino-3-[4-(2-amino-6-{1-[4-chloro-2-(3-methyl-pyrazol-1-yl)-phenyl-]-2,2,2-trifluoro-ethoxy}-pyrimidin-4-yl)-phenyl]-propionic acid (40)

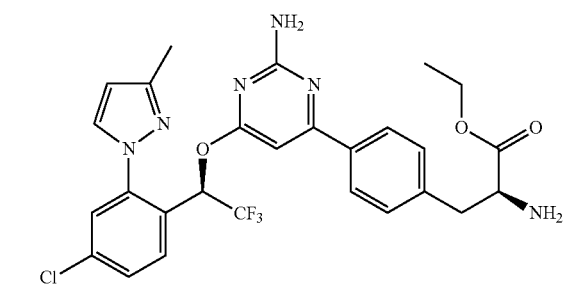

(S)-2-Amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl]-propionic acid ethyl ester (40)

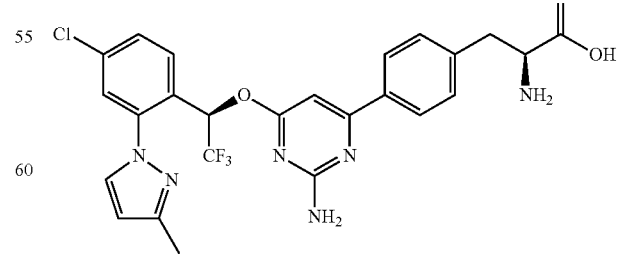

(S)-2-amino-3-(4-(2-amino-6-((R)-1-(4-chloro-2-(3-methyl-1H-pyrazol-1-yl)-phenyl)-2,2,2-trifluoroethoxy)pyrimidin-4-yl)phenyl)propionic acid

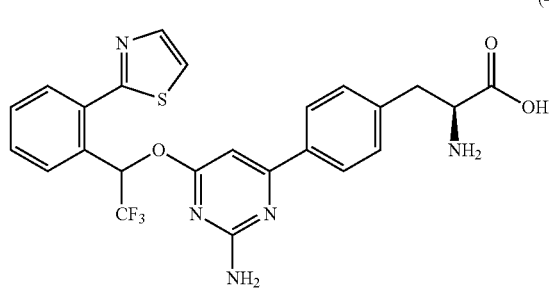

(41)

(S)-2-Amino-3-(4-{2-amino-6-[2,2,2-trifluoro-1-(2-thiazol-2-yl-phenyl)-ethoxy]-pyrimidin-4-yl}-phenyl)-propionic acid

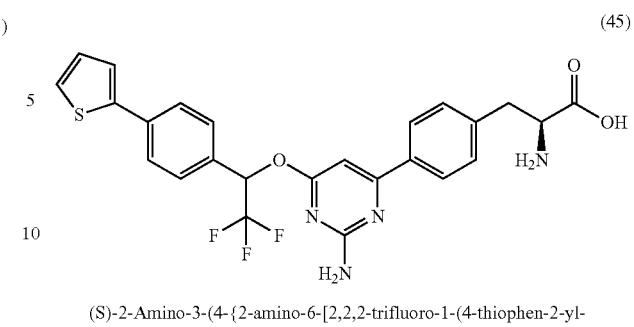

(45)

(S)-2-Amino-3-(4-{2-amino-6-[2,2,2-trifluoro-1-(4-thiophen-2-yl-phenyl)-ethoxy]-pyrimidin-4-yl}-phenyl)-propionic acid

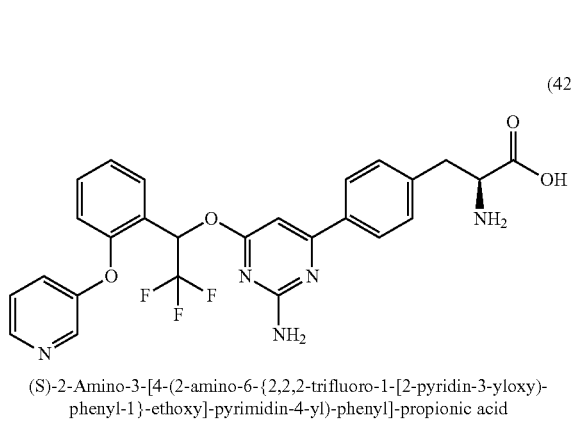

(42)

(S)-2-Amino-3-[4-(2-amino-6-{2,2,2-trifluoro-1-[2-pyridin-3-yloxy)-phenyl-1}-ethoxy]-pyrimidin-4-yl)-phenyl]-propionic acid

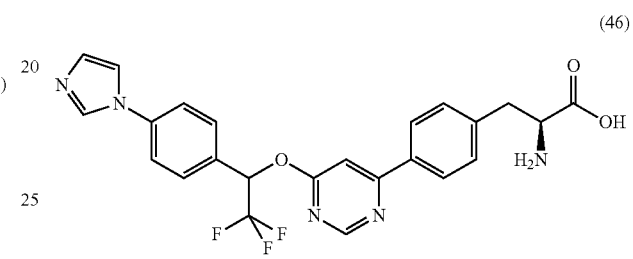

(46)

(S)-2-Amino-3-(4-{6-[2,2,2-trifluoro-1-(4-imidazol-1-yl-phenyl)-ethoxy]-pyrimidin-4-yl}-phenyl)-propionic acid

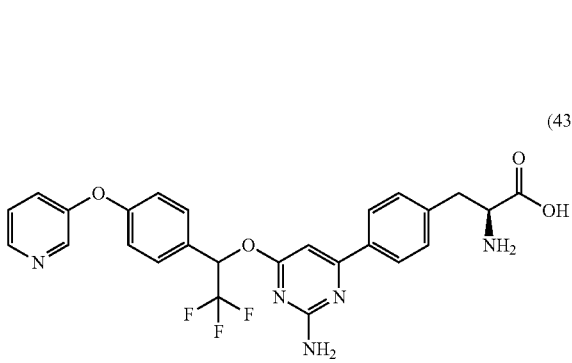

(43)

(S)-2-Amino-3-[4-(2-amino-6-{2,2,2-trifluoro-1-[4-(pyridin-3-yloxy)-phenyl]-ethoxy}-pyrimidin-4-yl)-phenyl]-propionic acid

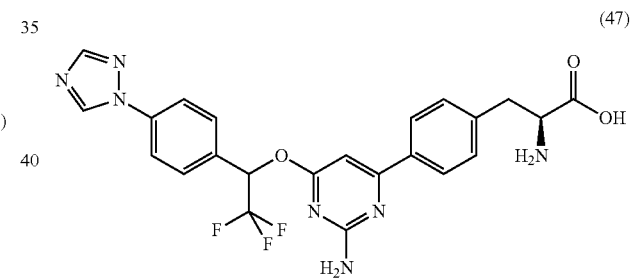

(47)

(S)-2-Amino-3-(4-{2-amino-6-[2,2,2-trifluoro-1-(4-[1,2,4]triazol-1-yl-phenyl)-ethoxy]-pyrimidin-4-yl}-phenyl)-propionic acid

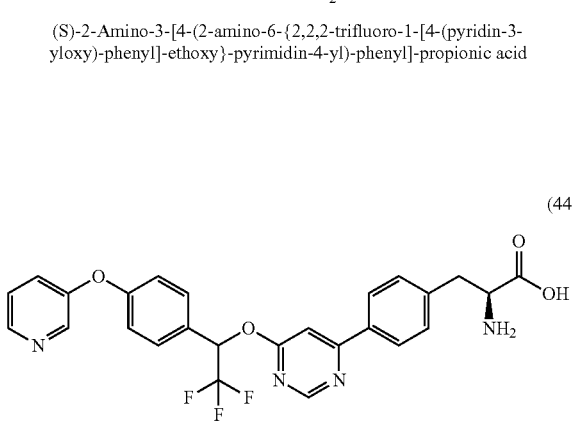

(44)

(S)-2-Amino-3-[4-(6-{2,2,2-trifluoro-1-[4-(pyridin-3-yloxy)-phenyl]-ethoxy}-pyrimidin-4-yl)-phenyl]-propionic acid

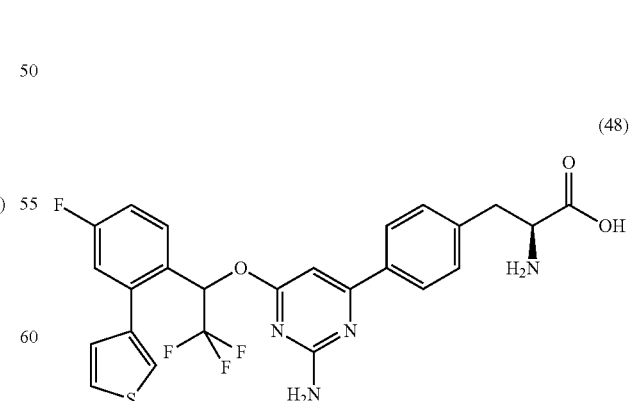

(48)

(S)-2-Amino-3-(4-{2-amino-6-[2,2,2-trifluoro-1-(4-fluoro-2-thiophen-3-yl-phenyl)ethoxy]-pyrimidin-4-yl}-phenyl)-propionic acid

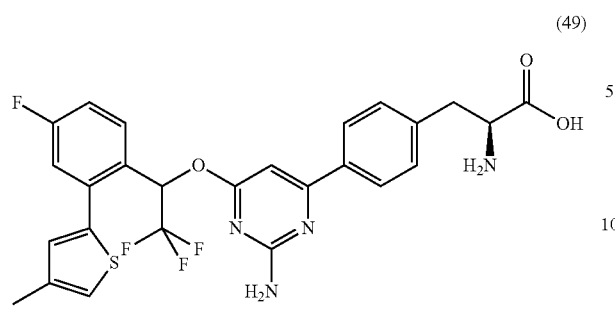

(49) (S)-2-Amino-3-(4-{2-amino-6-[2,2,2-trifluoro-1-(4-fluoro-2-thiophen-3-yl-phenyl)ethoxy]-pyrimidin-4-yl}-phenyl)-propionic acid

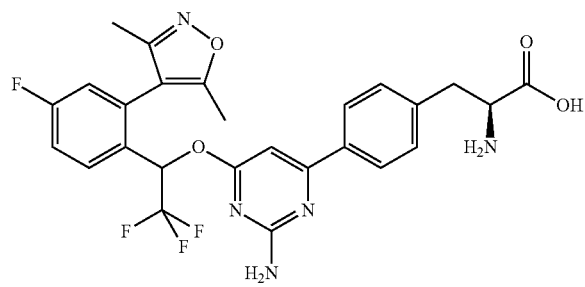

(50) (S)-2-Amino-3-[4-(2-amino-6-{1-[2-(3,5-dimethyl-isoxazol-4-yl)-4-fluoro-phenyl]-2,2,2-trifluoro-ethoxy}-pyrimidin-4-yl)-phenyl]-propionic acid

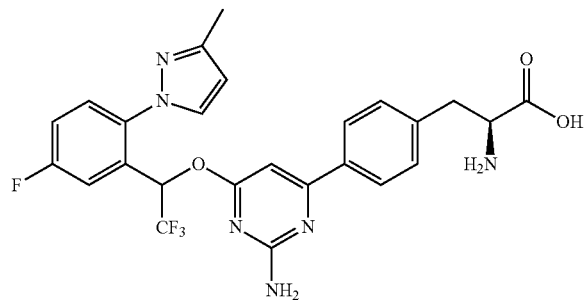

(51) (S)-2-amino-3-[4-(2-amino-6-{2,2,2-trifluoro-1-[5-fluoro-2-(3-methyl-pyrazol-1-yl)-phenyl]-ethoxy}-pyrimidin-4-yl)-phenyl]-propionic acid

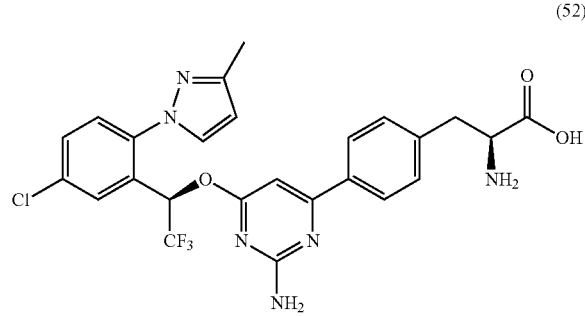

(52) (S)-2-amino-3-[4-(2-amino-6{2,2,2-trifluoro-1-[5-chloro-2-(3-methyl-pyrazol-1-yl)-phenyl]-ethoxy}-pyrimidin-4-yl)-phenyl]-propionic acid

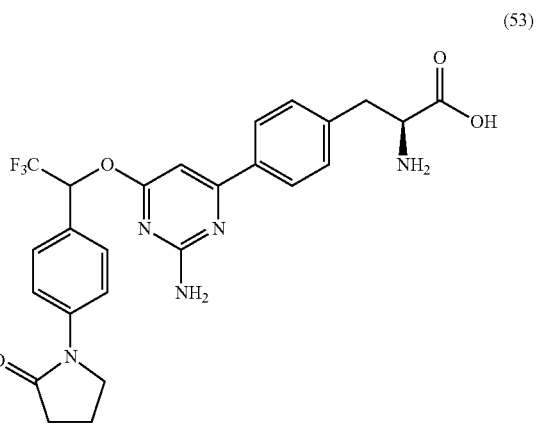

(53) (S)-2-amino-3-[4-(2-amino-6-{2,2,2-trifluoro-1-[4-(2-oxo-pyrrolidin-1-yl)-phenyl]-ethoxy}-pyrimidin-4-yl)-phenyl]-propionic acid

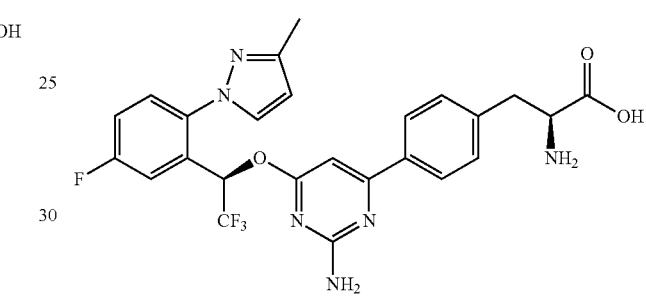

(54) (S)-2-Amino-3-[4-(2-amino-6-{(R)-2,2,2-trifluoro-1-[5-[fluoro-2-(3-methyl-pyrazol-1-yl)-phenyl]-ethoxy}-pyrimidin-4-yl)-phenyl]-propionic acid

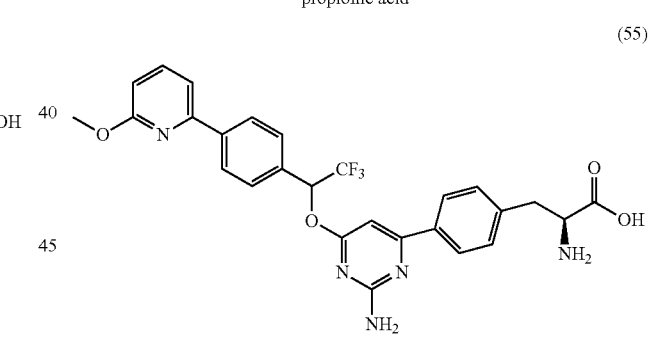

(55) (S)-2-Amino-3-[4-(2-amino-6-{2,2,2-trifluoro-1-[4-(6-methoxy-pyridin-2-yl)-phenyl]-ethoxy}-pyrimidin-4-yl)-phenyl]-propionic acid

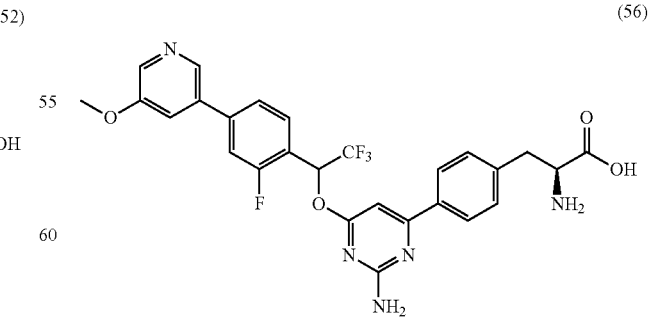

(56) (S)-2-Amino-3-[4-(2-amino-6-{2,2,2-trifluoro-1-[2-fluoro-4-(5-methoxy-pyridin-3-yl)-phenyl]-ethoxy}-pyrimidin-4-yl)-phenyl]-propionic acid

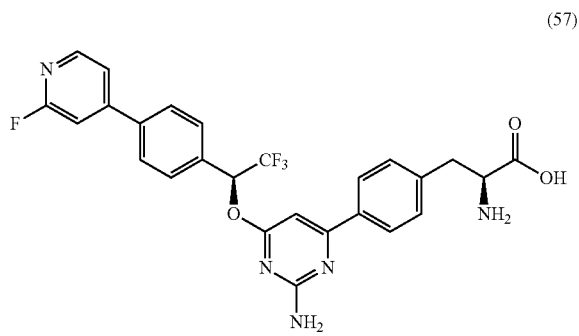

(57)

(S)-2-Amino-3-[4-(2-amino-6-{(S)-2,2,2-trifluoro-1-[4-(2-fluoro-pyridin-4-yl)-phenyl]-ethoxy}-pyrimidin-4-yl)-phenyl]-propionic acid

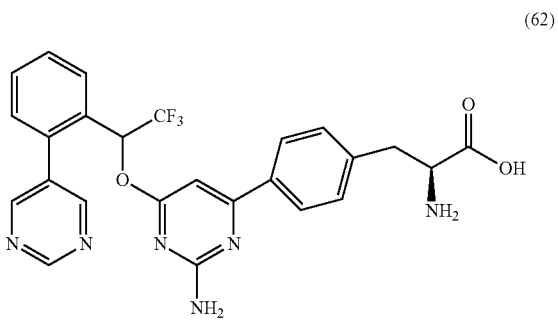

(62)

(S)-2-Amino-3-(4-{2-amino-6-[2,2,2-trifluoro-1-(2-pyrimidin-5-yl-phenyl)-ethoxy]-pyrimidin-4-yl}-phenyl)-propionic acid

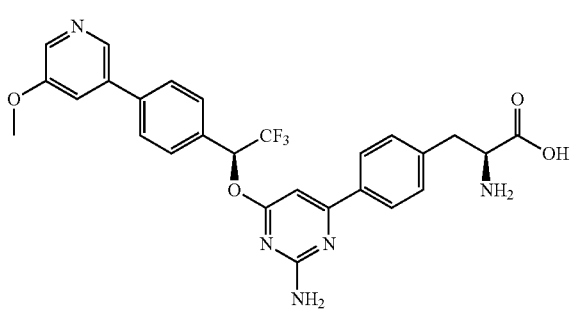

(58)

(S)-2-Amino-3-[4-(2-amino-6-{(S)-2,2,2-trifluoro-1-[4-(5-methoxy-pyridin-3-yl)-phenyl]-ethoxy}-pyrimidin-4-yl)-phenyl]-propionic acid

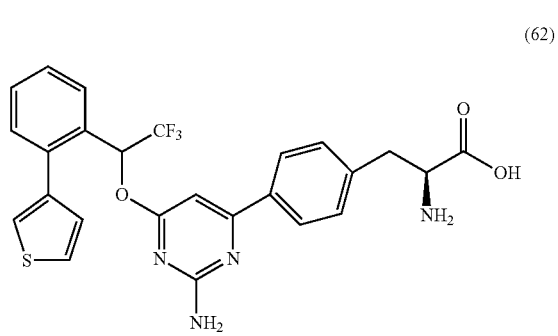

(62)

(S)-2-amino-3-(4-{2-amino-6-[2,2,2-trifluoro-1-(2-thiophen-3-yl-phenyl)-ethoxy]-pyrimidin-4-yl}-phenyl)-propionic acid

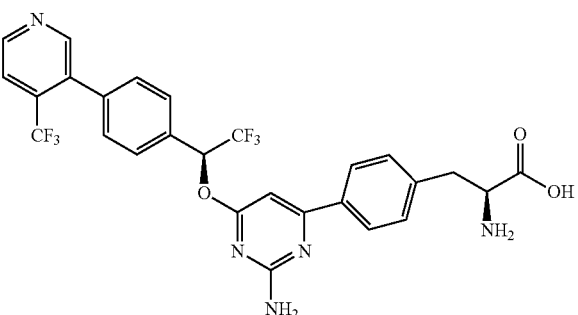

(59)

(S)-2-Amino-3-[4-(2-amino-6-{(S)-2,2,2-trifluoro-1-[4-(4-trifluoromethyl-pyridin-3-yl)-phenyl]-ethoxy}-pyrimidin-4-yl)-phenyl]-propionic acid

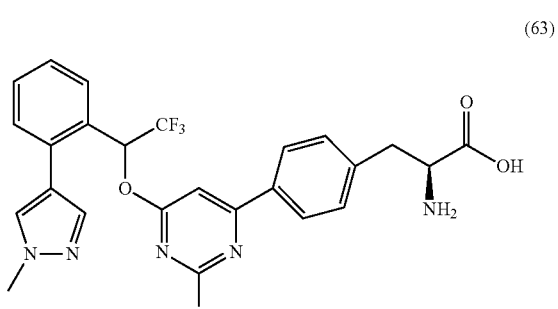

(63)

(S)-2-Amino-3-[4-(2-amino-6-{2,2,2-trifluoro-1-[2-(1-methyl-1H-pyrazol-4-yl)-phenyl]-ethoxy}-pyrimidin-4-yl)-phenyl]-propionic acid

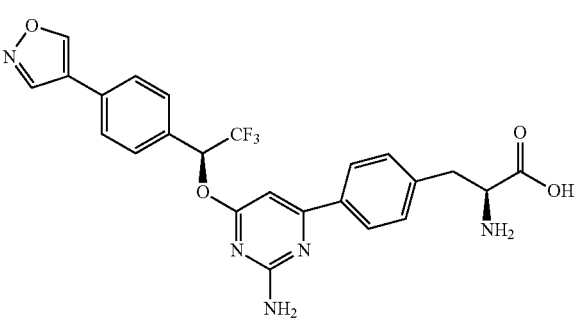

(60)

(S)-2-Amino-3-(4-{2-amino-6-[(S)-2,2,2-trifluoro-1-(4-isoxazol-4-yl-phenyl)-ethoxy]-pyrimidin-4-yl}-phenyl)-propionic acid

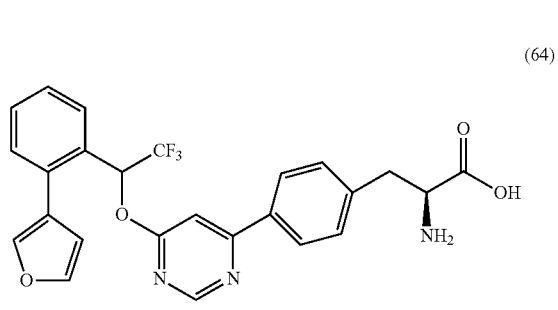

(64)

(S)-2-amino-3-(4-{6-[2,2,2-trifluoro-1-(2-furan-3-yl-phenyl)-ethoxy]-pyrimidin-4-yl}-phenyl)-propionic acid (65)

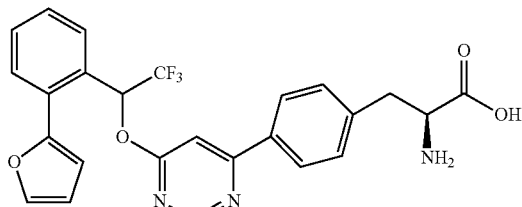

(S)-2-amino-3-(4-{6-[2,2,2-trifluoro-1-(2-furan-2-yl-phenyl)-ethoxy]-pyrimidin-4-yl}-phenyl)-propionic acid

(66) (2S)-2-amino-3-(4-(2-amino-6-(2,2,2-trifluoro-1-(4-(pyridin-3-yl)phenyl)ethoxy)pyrimidin-4-yl)phenyl)propanoic acid

(67) (2S)-2-amino-3-(4-(2-amino-6-(2,2,2-trifluoro-1-(2-(2-methylpyridin-4-yl)phenyl)ethoxy)pyrimidin-4-yl)phenyl)propanoic acid

(68) (2S)-2-amino-3-(4-(2-amino-6-(2,2,2-trifluoro-1-(2-(4-methylthiophen-3-yl)phenyl)ethoxy)pyrimidin-4-yl)phenyl)propanoic acid

(69) (2S)-3-(4-(6-(1-(2-(1H-pyrazol-1-yl)phenyl)-2,2,2-trifluoroethoxy)-2-aminopyrimidin-4-yl)phenyl)-2-aminopropanoic acid

(70) (2S)-2-amino-3-(4-(2-amino-6-(2,2,2-trifluoro-1-(4-(furan-2-yl)phenyl)ethoxy)pyrimidin-4-yl)phenyl)propanoic acid

(71) (2S)-2-amino-3-(4-(6-(2,2,2-trifluoro-1-(2-(pyridin-3-yloxy)phenyl)ethoxy)pyrimidin-4-yl)phenyl)propanoic acid

(72) (2S)-3-(4-(6-(1-(2-(1H-1,2,4-triazol-1-yl)phenyl)-2,2,2-trifluoroethoxy)-2-aminopyrimidin-4-yl)phenyl)-2-aminopropanoic acid

(73) (2S)-2-amino-3-(4-(2-amino-6-(2,2,2-trifluoro-1-(2-(furan-3-yl)phenyl)ethoxy)pyrimidin-4-yl)phenyl)propanoic acid

(74) (2S)-2-amino-3-(4-(2-amino-6-(2,2,2-trifluoro-1-(4-(furan-2-yl)-3-methoxyphenyl)ethoxy)pyrimidin-4-yl)phenyl)propanoic acid

(75) (2S)-2-amino-3-(4-(5-(2,2,2-trifluoro-1-(2-(furan-2-yl)phenyl)ethoxy)pyrazin-2-yl)phenyl)propanoic acid

(76) (2S)-3-(4-(5-(1-(2-(1H-pyrazol-1-yl)phenyl)-2,2,2-trifluoroethoxy)pyrazin-2-yl)phenyl)-2-aminopropanoic acid

(77) (2S)-2-amino-3-(4-(2-amino-6-(1-(4,5-dimethoxy-2-(1H-pyrazol-1-yl)phenyl)-2,2,2-trifluoroethoxy)pyrimidin-4-yl)phenyl)propanoic acid

(78) (2S)-2-amino-3-(4-(2-amino-6-(2,2,2-trifluoro-1-(2-(2-methyl-1H-imidazol-1-yl)phenyl)ethoxy)pyrimidin-4-yl)phenyl)propanoic acid

(79) (2S)-2-amino-3-(4-(2-amino-6-(2,2,2-trifluoro-1-(2-(5-methylthiophen-2-yl)phenyl)ethoxy)pyrimidin-4-yl)phenyl)propanoic acid

(80) (2S)-2-amino-3-(4-(2-amino-6-(1-(2-(5-(dimethylcarbamoyl)furan-2-yl)phenyl)-2,2,2-trifluoroethoxy)pyrimidin-4-yl)phenyl)propanoic acid

(81) (2S)-2-amino-3-(4-(2-amino-6-(2,2,2-trifluoro-1-(4-fluoro-2-(thiophen-2-yl)phenyl)ethoxy)pyrimidin-4-yl)phenyl)propanoic acid

(82) (2S)-2-amino-3-(4-(6-(2,2,2-trifluoro-1-(4-fluoro-2-(thiophen-2-yl)phenyl)ethoxy)pyrimidin-4-yl)phenyl)propanoic acid

(83) (2S)-2-amino-3-(4-(6-(2,2,2-trifluoro-1-(4-fluoro-2-(thiophen-3-yl)phenyl)ethoxy)pyrimidin-4-yl)phenyl)propanoic acid

(84) (2S)-2-amino-3-(4-(6-(2,2,2-trifluoro-1-(4-fluoro-2-(4-methylthiophen-2-yl)phenyl)ethoxy)pyrimidin-4-yl)phenyl)propanoic acid

(85) (S)-2-amino-3-(4-(2-amino-6-((R)-2,2,2-trifluoro-1-(4-(6-fluoropyridin-3-yl)phenyl)ethoxy)pyrimidin-4-yl)phenyl)propanoic acid

(86) (2S)-3-(4-(6-(1-(4-(1H-imidazol-1-yl)phenyl)-2,2,2-trifluoroethoxy)-2-aminopyrimidin-4-yl)phenyl)-2-aminopropanoic acid

(87) (2S)-2-amino-3-(4-(6-(2,2,2-trifluoro-1-(4-(thiophen-2-yl)phenyl)ethoxy)pyrimidin-4-yl)phenyl)propanoic acid

(88) (S)-2-amino-3-(4-(2-amino-6-((R)-2,2,2-trifluoro-1(4-(pyrimidin-5-yl)phenyl)ethoxy)pyrimidin-4-yl)phenyl)propanoic acid

(89) (2S)-2-amino-3-(4-(6-(1-(2-(3,5-dimethylisoxazol-4-yl)-4-fluorophenyl)-2,2,2-trifluoroethoxy)pyrimidin-4-yl)phenyl)propanoic acid

(90) (S)-2-amino-3-(4-(2-amino-6-((R)-2,2,2-trifluoro-1-(4-(2-methylpyridin-4-yl)phenyl)ethoxy)pyrimidin-4-yl)phenyl)propanoic acid

(91) (2S)-3-(4-(6-(1-(4-(1H-1,2,4-triazol-1-yl)phenyl)-2,2,2-trifluoroethoxy)pyrimidin-4-yl)phenyl)-2-aminopropanoic acid

(92) (2S)-2-amino-3-(4-(2-amino-6-(2,2,2-trifluoro-1-(4-(piperidin-1-ylmethyl)phenyl)ethoxy)pyrimidin-4-yl)phenyl)propanoic acid

(93) (2S)-2-amino-3-(4-(2-amino-6-(2,2,2-trifluoro-1-(2-fluoro-4-(2-methylpyridin-4-yl)phenyl)ethoxy)pyrimidin-4-yl)phenyl)propanoic acid

(94) (2S)-2-amino-3-(4-(2-amino-6-(1-(4-(6-chloropyridazin-3-yl)phenyl)-2,2,2-trifluoroethoxy)pyrimidin-4-yl)phenyl)propanoic acid

(95) (2S)-2-amino-3-(4-(2-amino-6-(1-(4-(4-tert-butylthiazol-2-yl)phenyl)-2,2,2-trifluoroethoxy)pyrimidin-4-yl)phenyl)propanoic acid

(96) (2S)-2-amino-3-(4-(2-amino-6-(2,2,2-trifluoro-1-(3'-methoxy-3-(3-methyl-1H-pyrazol-1-yl)biphenyl-4-yl)ethoxy)pyrimidin-4-yl)phenyl)propanoic acid

(97) (2S)-2-amino-3-(4-(2-amino-6-(1-(5-chloro-2-(3-methyl-1H-pyrazol-1-yl)phenyl)-2,2,2-trifluoroethoxy)pyrimidin-4-yl)phenyl)propanoic acid

(98) (S)-2-amino-3-(4-(2-amino-6-((R)-2,2,2-trifluoro-1-(3'-methoxybiphenyl-4-yl)ethoxy)pyrimidin-4-yl)phenyl)propanoate tosylate.

(99) (S)-2-amino-3-(4-(2-amino-6-((R)-2,2,2-trifluoro-1-(3'-methoxybiphenyl-4-yl)ethoxy)pyrimidin-4-yl)phenyl)propanoate maleate (100) (S)-ethyl 2-amino-3-(4-(2-amino-6-((R)-1-(4-chloro-2-(3-methyl-1-H-pyrazol-1-yl)phenyl)-2,2,2-trifluoroethoxy)pyrimidin-4-yl)phenyl)propanoate hippurate (101) (S)-ethyl 2-amino-3-(4-(2-amino-6-((R)-1-(4-chloro-2-(3-methyl-1-H-pyrazol-1-yl)phenyl)-2,2,2-trifluoroethoxy)pyrimidin-4-yl)phenyl)propanoate succinate (102)

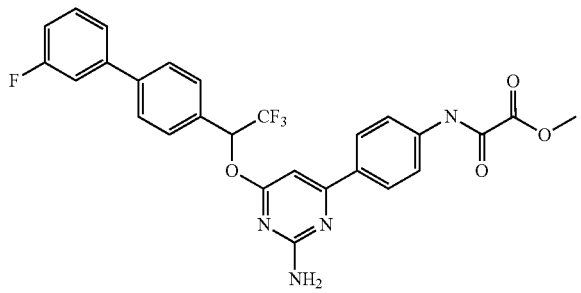

(103)

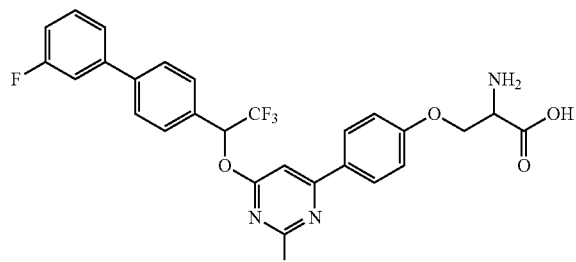

(104)

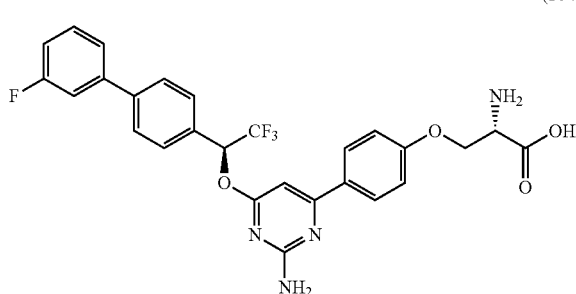

(105)

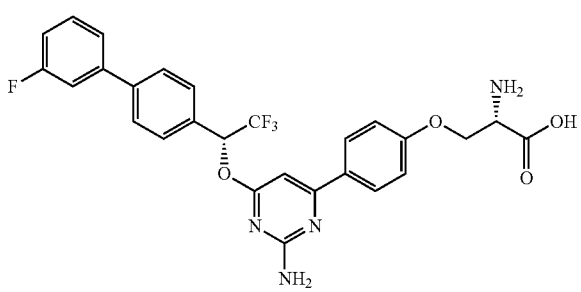

(106)

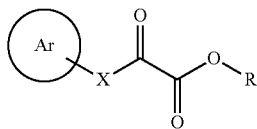

where Ar is a structure comprising multiple aryl or heterocycle rings;
X is —CH$_2$— or N; and
R is hydrogen or optionally substituted alkyl, alkyl-aryl, alkyl-heterocycle, aryl, or heterocycle.

In some compounds, X is N.
In some compounds, R is methyl, ethyl, or isopropyl.
In some compounds, X is N and R is methyl.
In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(107)

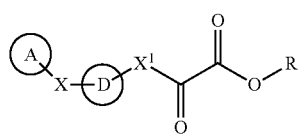

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; R is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; and X$^1$ is —CH$_2$— or N.

In some compounds, X$^1$ is N.
In some compounds, R is methyl, ethyl, or isopropyl.
In some compounds, X$^1$ is N and R is methyl.
In some compounds, X$^1$ is N, R is methyl, X is —C(R$_3$R$_4$)O—, R$_3$ is hydrogen, and R$_4$ is substituted alkyl.

(108)

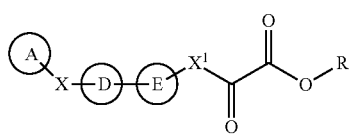

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; and X$^1$ is —CH$_2$— or N.

In some compounds, X$^1$ is N.
In some compounds, R is methyl, ethyl, or isopropyl.
In some compounds, X$^1$ is N and R is methyl.
In some compounds, A is fluoro-substituted biphenyl, X$^1$ is N, R is methyl, X is —C(R$_3$R$_4$)O—, R$_3$ is hydrogen, and R$_4$ is substituted alkyl. In some of these compounds, A is 3'-fluorobiphenyl. In some of these compounds, R$_4$ is halo-substituted methyl. In some of these compounds, D is substituted pyrimidinyl and E is phenyl. In some of these compounds, D is 2-substituted pyrimidinyl.

In some compounds, A is optionally substituted biphenyl, X is —C(R$_3$R$_4$)O—, R$_3$ is hydrogen, R$_4$ is optionally substituted lower alkyl, D is optionally substituted pyrimidinyl, E is phenyl, X$^1$ is N, and R is lower alkyl. In some of these compounds, A is 2'-, 3'-, 4'-, 5', or 6'-halo-substituted biphenyl, X is —C(R$_3$R$_4$)O—, R$_3$ is hydrogen, R$_4$ is halo-substituted methyl or ethyl, D is 2-substituted pyrimidinyl, E is phenyl, X$^1$ is N, and R is methyl or ethyl. In some of these compounds, A is 2'-, 3'-, 4'-, 5', or 6'-fluoro-substituted biphenyl, X is —C(R$_3$R$_4$)O—, R$_3$ is hydrogen, R$_4$ is fluoro-substituted methyl, D is 2-amino substituted pyrimidinyl, E is phenyl, X$^1$ is N, and R is methyl.

(109)

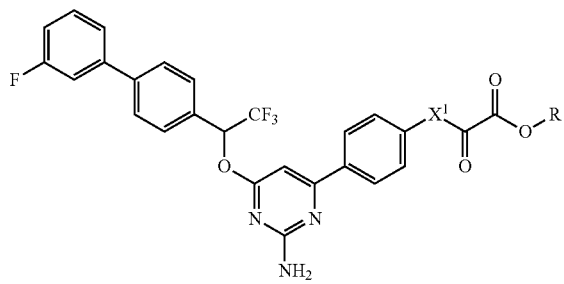

where: X$^1$ is —CH$_2$— or N; and

R is hydrogen or optionally substituted alkyl, alkyl-aryl, alkyl-heterocycle, aryl, or heterocycle.

In some compounds, X$^1$ is N.

In some compounds, R is methyl, ethyl, or isopropyl.

(110)

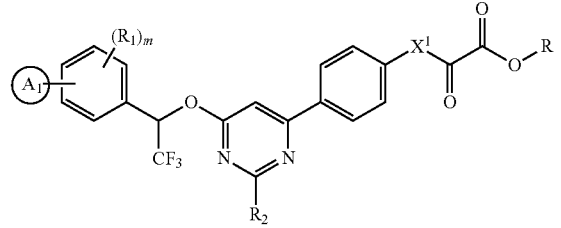

where A$_1$ is optionally substituted aryl or heterocycle; each R$_1$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; R$_2$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_C$ is independently hydrogen or optionally substituted alkyl, alkyl-aryl or alkyl-heterocycle; X$^1$ is —CH$_2$— or N; R is hydrogen or optionally substituted alkyl, alkyl-aryl, alkyl-heterocycle, aryl, or heterocycle; and m is 1-4.

(111)

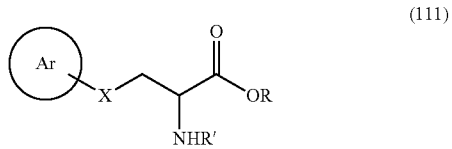

where:

Ar is a structure comprising multiple aryl or heterocycle rings;

X is N, O, or S;

R is hydrogen or optionally substituted alkyl, alkyl-aryl, alkyl-heterocycle, aryl, or heterocycle; and R' is hydrogen or optionally substituted alkyl.

In some compounds, X is O.

In some compounds, X is O and R and R' are hydrogen.

In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(112)

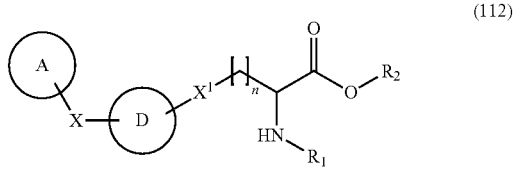

where A is optionally substituted cycloalkyl, aryl, or heterocycle; X is a bond (i.e., A is directly bound to D), —O—, —S—, —C(O)—, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —C(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; R$_1$ is hydrogen or alkyl; R$_2$ is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; n is 0-3; and X$^1$ is N, O, or S. In certain embodiments, the carbon having the HNR$^1$ group is in the S configuration.

In some compounds, X$^1$ is O and n is 1.

In some compounds, X$^1$ is O, n is 1, R$_1$ is hydrogen, and R$_2$ is hydrogen.

In some compounds, X$^1$ is O, n is 1, R$_1$ is hydrogen, R$_2$ is hydrogen, X is —C(R$_3$R$_4$)O—, R$_3$ is hydrogen, and R$_4$ is substituted alkyl.

(113)

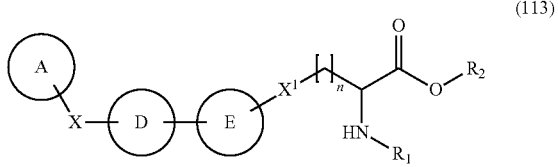

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R$_1$ is H or alkyl; R$_2$ is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; n is 0-3; and X$^1$ is N, O, or S.

In some compounds, X$^1$ is O.

In some compounds, X$^1$ is O, n is 1, R$_1$ is hydrogen, and R$_2$ is hydrogen.

In some compounds, X is O, n is 1, R$_1$ is hydrogen, R$_2$ is hydrogen, X is —C(R$_3$R$_4$)O—, R$_3$ is hydrogen, and R$_4$ is substituted alkyl. In some of these embodiments, A is fluoro-substituted biphenyl and R$_3$ is hydrogen. In some of these embodiments, A is 3'-fluorobiphenyl. In some of these embodiments, R$_4$ is halo-substituted methyl. In some of these embodiments, D is substituted pyrimidinyl and E is phenyl. In some of these embodiments, D is 2-substituted pyrimidinyl In some compounds, A is optionally substituted biphenyl, X is —C(R$_3$R$_4$)O—, R$_3$ is hydrogen, R$_4$ is optionally substituted lower alkyl, D is optionally substituted pyrimidinyl, E is phenyl, X$^1$ is O, n is 1, R$_1$ is hydrogen or lower alkyl, and R$_2$ is hydrogen or lower alkyl. In some of these compounds, A is 2'-, 3'-, 4'-, 5', or 6'-halo-substituted biphenyl, X is —C(R$_3$R$_4$)O—, R$_3$ is hydrogen, R$_4$ is halo-substituted methyl or ethyl, D is 2-substituted pyrimidinyl, E is phenyl, X$^1$ is O, n is 1, R$_1$ is hydrogen, and R$_2$ is hydrogen. In some of these compounds, A is 2'-, 3'-, 4'-, 5', or 6'-fluoro-substituted biphenyl, X is —C(R$_3$R$_4$)O—, R$_3$ is hydrogen, R$_4$ is fluoro-substituted methyl, D is 2-amino substituted pyrimidinyl, E is phenyl, X$^1$ is O, n is 1, R$_1$ is hydrogen, and R$_2$ is hydrogen.

(114)

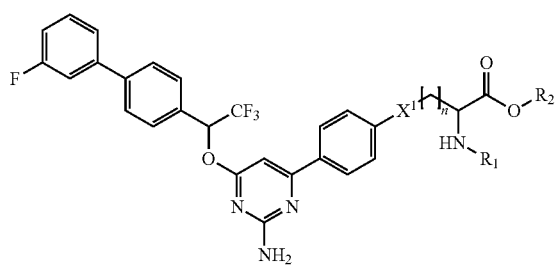

where:
X$^1$ is N, O, or S;
R$_1$ is hydrogen or optionally substituted alkyl;
R$_2$ is hydrogen or optionally substituted alkyl, alkyl-aryl, alkyl-heterocycle, aryl, or heterocycle; and
n is 0-3.

In some compounds, X$^1$ is O and n is 1. In certain embodiments, the carbon having the HNR$^1$ group is in the S configuration.

(115)

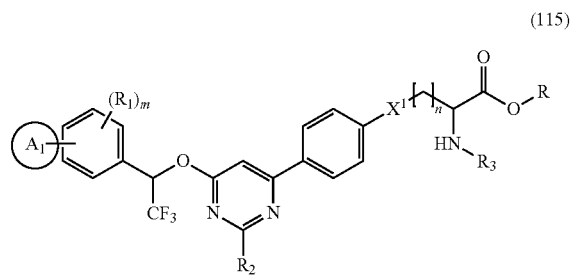

where A$_1$ is optionally substituted aryl or heterocycle; R is hydrogen or optionally substituted alkyl, alkyl-aryl, alkyl-heterocycle, aryl, or heterocycle; each R$_1$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; R$_2$ is halogen, hydrogen, C(O)R$_A$, OR$_A$, NR$_B$R$_C$, S(O$_2$)R$_A$, or optionally substituted alkyl, alkyl-aryl or alkyl-heterocycle; R$_3$ is hydrogen or optionally substituted alkyl; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_C$ is independently hydrogen or optionally substituted alkyl, alkyl-aryl or alkyl-heterocycle; X$^1$ is N, O, or S; m is 1-4; and n is 0-3. In certain embodiments, the carbon having the HNR$_3$ group is in the S configuration.

In some compounds, X$^1$ is O and n is 1.

In some compounds, X$^1$ is O, n is 1, R$_1$ is hydrogen, and R$_2$ is hydrogen.

(116)

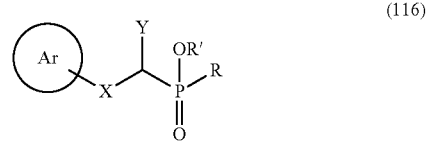

where:
Ar is a structure comprising multiple aryl or heterocycle rings;
X is —CH$_2$— or N;
Y is hydrogen or NH$_2$;
R is optionally substituted alkyl or alkoxy; and
R' is hydrogen or optionally substituted alkyl, alkyl-aryl, alkyl-heterocycle, aryl, or heterocycle.

In some compounds, X is N, Y is NH$_2$, R is optionally substituted alkyl, and R' is hydrogen.

In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(117)

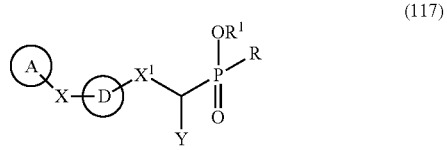

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; X$^1$ is —CH$_2$— or N; Y is hydrogen or NH$_2$; R is optionally substituted alkyl or alkoxy; and R$^1$ is hydrogen or optionally substituted alkyl, alkyl-aryl, alkyl-heterocycle, aryl, or heterocycle. In certain embodiments where Y is NH$_2$, the carbon to which Y is attached is in the S configuration. In other embodiments, the carbon to which Y is attached is in the R configuration.

In some compounds, X$^1$ is N, Y is NH$_2$, R is optionally substituted alkyl, and R' is hydrogen.

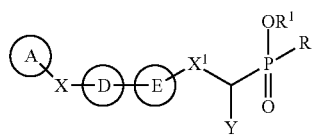

(118)

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; X$^1$ is —CH$_2$— or N; Y is hydrogen or NH$_2$; R is optionally substituted alkyl or alkoxy; and R$^1$ is hydrogen or optionally substituted alkyl, alkyl-aryl, alkyl-heterocycle, aryl, or heterocycle. In certain embodiments where Y is NH$_2$, the carbon to which Y is attached is in the S configuration. In other embodiments, the carbon to which Y is attached is in the R configuration.

In some compounds, X$^1$ is N, Y is NH$_2$, R is optionally substituted alkyl, and R' is hydrogen.

In some compounds, A is optionally substituted biphenyl, X is —C(R$_3$R$_4$)O—, R$_3$ is hydrogen, R$_4$ is optionally substituted lower alkyl, D is optionally substituted pyrimidinyl, E is phenyl, X$^1$ is —CH$_2$— or N; Y is hydrogen or NH$_2$, R is optionally substituted alkyl, and R$^1$ is hydrogen or lower alkyl. In some of these compounds, A is 2'-, 3'-, 4'-, 5', or 6'-halo-substituted biphenyl, X is —C(R$_3$R$_4$)O—, R$_3$ is hydrogen, R$_4$ is halo-substituted methyl or ethyl, D is 2-substituted pyrimidinyl, E is phenyl, X$^1$ is N; Y is hydrogen, R is optionally substituted lower alkyl, and R$^1$ is hydrogen. In some of these compounds, A is 2'-, 3'-, 4'-, 5', or 6'-fluoro-substituted biphenyl, X is —C(R$_3$R$_4$)O—, R$_3$ is hydrogen, R$_4$ is fluoro-substituted methyl, D is 2-amino substituted pyrimidinyl, E is phenyl, X$^1$ is N; Y is hydrogen, R is optionally substituted methyl or ethyl, and R$^1$ is hydrogen.

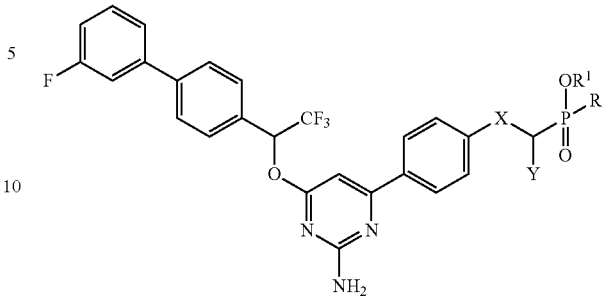

(119)

where:
X is —CH$_2$— or N;
Y is hydrogen or NH$_2$;
R is hydrogen or optionally substituted alkyl or alkoxy; and
R' is R is hydrogen or optionally substituted alkyl, alkyl-aryl, alkyl-heterocycle, aryl, or heterocycle. In certain embodiments where Y is NH$_2$, the carbon to which Y is attached is in the S configuration. In other embodiments, the carbon to which Y is attached is in the R configuration.

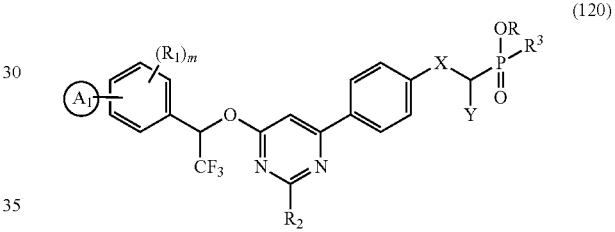

(120)

where A$_1$ is optionally substituted aryl or heterocycle; R is hydrogen or optionally substituted alkyl, alkyl-aryl, alkyl-heterocycle, aryl, or heterocycle; each R$_1$ is independently halogen, hydrogen, C(O)R$_A$, OR$_A$, NR$_A$R$_C$, S(O$_2$)R$_A$, or optionally substituted alkyl, alkyl-aryl or alkyl-heterocycle; R$_2$ is halogen, hydrogen, C(O)R$_A$, OR$_A$, NR$_B$R$_C$, S(O$_2$)R$_A$, or optionally substituted alkyl, alkyl-aryl or alkyl-heterocycle; R$_3$ is hydrogen or optionally substituted alkyl; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_C$ is independently hydrogen or optionally substituted alkyl, alkyl-aryl or alkyl-heterocycle; X is —CH$_2$— or N; Y is hydrogen or NH$_2$; and m is 1-4. In certain embodiments where Y is NH$_2$, the carbon to which Y is attached is in the S configuration. In other embodiments, the carbon to which Y is attached is in the R configuration.

The present invention provides pharmaceutical compositions comprising a therapeutically effective amount of a TPH1 inhibitor disclosed herein and at least one pharmaceutically acceptable excipient. In certain embodiments, the TPH1 inhibitor may be in the form of a salt with a physiologically acceptable acid or base.

The present invention also provides methods where the patient is administered both a TPH1 inhibitor and a serotonin receptor antagonist. The TPH1 inhibitor and the serotonin receptor antagonist may be administered together in a single pharmaceutical composition or in separate pharmaceutical compositions.

In certain embodiments, the serotonin receptor antagonist is an HT1B, HT2A, or HT2B serotonin receptor antagonist, and, most preferably, an HT1B serotonin receptor antagonist. In certain embodiments, the serotonin receptor antagonist is an HT1B serotonin receptor antagonist listed in Table 3.

In certain embodiments, the low bone mass disease is osteoporosis, osteoporosis pseudoglioma syndrome (OPPG), osteopenia, osteomalacia, renal osteodystrophy, faulty bone formation or resorption, Paget's disease, fractures and broken bones, or bone metastasis. Preferably, the low bone mass disease is osteoporosis.

In other embodiments, the patient is being treated with an SSRI, a bisphosphonate, or a beta blocker in addition to an agent that lowers the level of serum serotonin. In some embodiments, the methods of the present invention also comprise administering an SSRI, a bisphosphonate, or a beta blocker in addition to an agent that lowers the level of serum serotonin.

In certain embodiments, the patient is being treated with an agent that increases the level of serum serotonin (e.g., an SSRI) where the agent is administered for a purpose unrelated to treatment of a bone mass disease (e.g., to treat depression) or the patient has a condition associated with an increased level of serum serotonin.

In certain embodiments, the patient's level of serum serotonin is measured prior to administering the agent that lowers the level of serum serotonin. In other embodiments, the patient's level of serum serotonin is measured after administering the agent that lowers the level of serum serotonin. In some embodiments, the patient's level of serum serotonin is measured before and after administering the agent that lowers the level of serum serotonin.

In certain embodiments, the agent that lowers the level of serum serotonin is repeatedly administered to the patient and the patient's level of serum serotonin is repeatedly measured until the patient's level of serum serotonin is reduced to desired level, e.g., by at least about 10%, compared to the level measured prior to the first administration of the agent that lowers the level of serum serotonin.

In certain embodiments, the patient has been identified as having a serum serotonin level that is more than 10%, 25%, 35%, 50%, 75%, 100%, or 200% higher than the normal level of serum serotonin.

In certain embodiments, the patient is administered an agent that increases brain derived scrotonin in addition to the agent that lowers the level of serum serotonin. In preferred embodiments, the agent that increases brain derived serotonin is an agent that increases TPH2 activity.

In certain embodiments, the patient's level of serum serotonin is lowered by at least about 10%, at least about 20%, at least about 30%, at least about 40%, at least about 50%, at least about 60%, at least about 70%, at least about 80%, or at least about 90% compared to the level before administering the agent that lowers the level of serum serotonin.

In certain embodiments, the agent that lowers the level of serum serotonin is administered in an amount of from about 1 mg/day to about 2 g/day.

The present invention provides a pharmaceutical composition comprising an amount of an agent that lowers the level of serum serotonin in a patient to whom the composition is administered by at least about 10%, at least about 20%, at least about 30%, at least about 40%, at least about 50%, at least about 60%, at least about 70%, at least about 80%, or at least about 90%.

The present invention provides a pharmaceutical composition comprising a therapeutically effective amount of an agent that lowers the level of serum serotonin in a patient to whom the composition is administered. In some embodiments, the pharmaceutical composition comprises an agent that lowers the level of serum serotonin and an agent that raises the level of brain-derived serotonin.

In some embodiments, the pharmaceutical composition comprises a compound disclosed herein that lowers the level of serum serotonin and an SSRI, a bisphosphonate, or a beta blocker. In certain embodiments, the pharmaceutical composition also comprises a serotonin receptor antagonist that is an HT1B, HT2A or HT2B serotonin receptor antagonist, preferably an HT1B serotonin receptor antagonist.

In certain embodiments, the pharmaceutical composition comprises both a TPH1 inhibitor and a scrotonin receptor antagonist.

The present invention also provides a method for identifying a patient at risk of developing a disease associated with low bone mass and treating the patient, comprising, a) determining the level of serum scrotonin in a biological sample taken from the patient and in a biological sample taken from the from a normal subject, b) concluding that the patient is at risk of developing the disease if the level of serum serotonin in the sample from the patient is elevated by at least about 25% above the serum serotonin level in the sample from the normal subject, and c) administering to the patient a therapeutically effective amount of a compound disclosed herein;

whereby the patient's serum serotonin level is lowered.

BRIEF DESCRIPTION OF THE FIGURES

FIG. 19. Histological analysis of vertebrae or femurs of sham and OVX mice treated for 6 weeks with vehicle or the indicated dose (25, 100 or 250 mg/kg/day) of LP-533,401 (LP) from week 6 to 12 post-ovariectomy. BV/TV, Bone volume over trabecular volume; Nb.Ob/T.Ar, osteoblast number over trabecular area; BFR, bone formation rate; OcS/BS, osteoclast surface over bone surface.

DETAILED DESCRIPTION OF THE INVENTION

Figure 1:
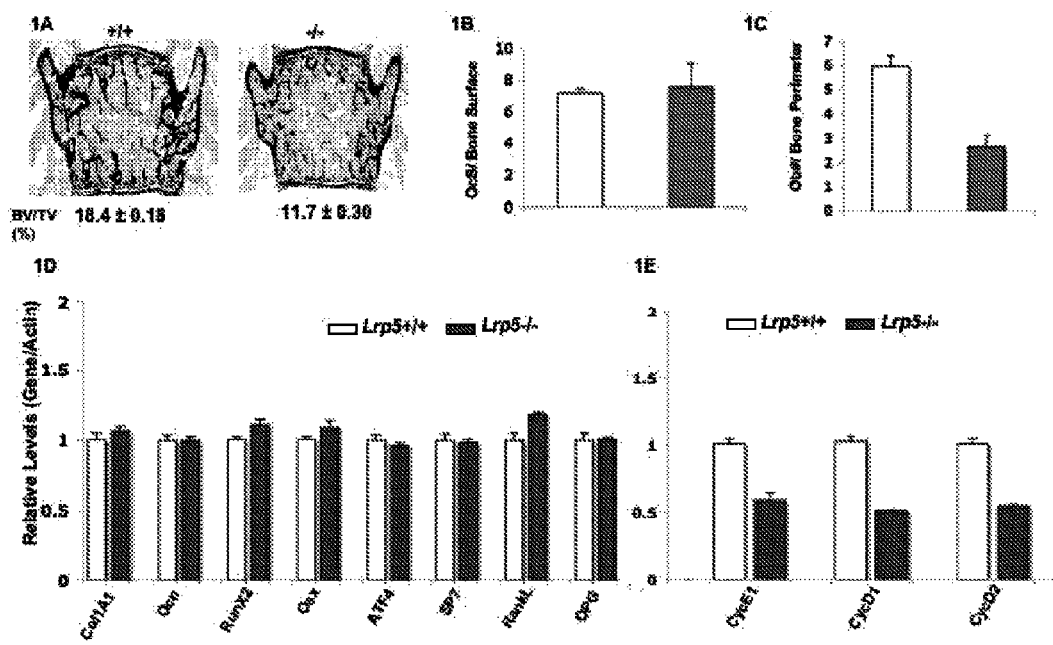
FIG. 1. Lrp5−/− mice have low bone mass (A) with no change in osteoclast surface (B) but decreased osteoblast numbers (C). Real-time PCR analysis of Lrp5−/− molecular signature. Lrp5−/− osteoblasts do not show changes in osteoblast-specific gene expression (D) but have decreased Cyclin genes expression (E).

The term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NH-CONH-alkyl-).

The term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

The term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

The term "alkoxy" means an —O-alkyl group. Examples of alkoxy groups include —$OCH_3$, —$OCH_2CH_3$, —$O(CH_2)_2CH_3$, —$O(CH_2)_3CH_3$, —$O(CH_2)_4$—$CH_3$, and —$O(CH_2)_5CH_3$.

Term "alkylaryl" or "alkyl-aryl" means an alkyl moiety bound to an aryl moiety.

The term "alkylheteroaryl" or "alkyl-heteroaryl" means an alkyl moiety bound to a heteroaryl moiety.

The term "alkylheterocycle" or "alkyl-heterocycle" means an alkyl moiety bound to a heterocycle moiety.

The term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

The term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

The term "arylalkyl" or "aryl-alkyl" means an aryl moiety bound to an alkyl moiety.

The terms "halogen" and "halo" encompass fluorine, chlorine, bromine, and iodine.

The term "heteroalkyl" refers to an alkyl moiety (e.g., linear, branched or cyclic) in which at least one of its carbon atoms has been replaced with a heteroatom (e.g., N, O or S).

The term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

The term "heteroarylalkyl" or "heteroaryl-alkyl" means a heteroaryl moiety bound to an alkyl moiety.

The term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

The term "heterocyclealkyl" or "heterocycle-alkyl" refers to a heterocycle moiety bound to an alkyl moiety.

The term "heterocycloalkyl" refers to a non-aromatic heterocycle.

The term "heterocycloalkylalkyl" or "heterocycloalkyl-alkyl" refers to a heterocycloalkyl moiety bound to an alkyl moiety.

The term "disease or disorder mediated by peripheral serotonin" refers to a disease or disorder having one or more symptoms the severity of which are affected by peripheral serotonin levels.

Diseases associated with low bone density ("low bone mass diseases"), as used herein, refers to any bone disease or state that results in or is characterized by loss of health or integrity to bone due to abnormally low bone mass, and includes, but is not limited to, osteoporosis, osteoporosis pseudoglioma syndrome (OPPG), osteopenia, osteomalacia, renal osteodystrophy, faulty bone formation or resorption, Paget's disease, fractures and broken bones, and bone metastasis. More particularly, bone diseases that can be treated and/or prevented in accordance with the present invention include bone diseases characterized by a decreased bone mass relative to that of corresponding non-diseased bone.

Prevention of bone disease means actively intervening as described herein prior to overt disease onset to prevent the disease or minimize the extent of the disease or slow its course of development.

Treatment of bone disease means actively intervening after onset to slow down, ameliorate symptoms of minimize the extent of or reverse the disease or situation in a patient who is known or suspected of having a bone disease, particularly a low bone mass disease. More specifically, treating refers to a method that modulates bone mass to more closely resemble that of corresponding non-diseased bone (that is a corresponding bone of the same type, e.g., long, vertebral, etc.) in a non-diseased state.

Unless otherwise indicated, a "therapeutically effective amount" of a compound is an amount that provides a therapeutic benefit in the treatment or management of a disease or condition, delays or minimizes one or more symptoms associated with the disease or condition, or enhances the therapeutic efficacy of another therapeutic agent. An agent is said to be administered in a "therapeutically effective amount" if the amount administered results in a desired change in the physiology of a recipient mammal (e.g., increases bone mass in a mammal having or at risk of developing a low bone mass disease) compared to pre-treatment levels. That is, drug therapy results in treatment, i.e., modulates bone mass to more closely resemble that of corresponding non-diseased bone (such as a corresponding bone of the same type, e.g., long, vertebral, etc.) in a non-diseased state. For example, a therapeutically effective amount of a TPH1 inhibitor that reduces serotonin synthesis includes, but is not limited to, an amount that reduce serum serotonin levels to a level that is at least about 10% less than the level before drug treatment.

A therapeutic agent such as a TPH1 inhibitor significantly reduces serum serotonin if the post-treatment level of serotonin is reduced at least about 10% or more compared to pre-treatment levels. Patients at risk of developing a low bone mass disease include, but are not limited to, patients whose serum serotonin levels are elevated by about 25% or more compared to serum serotonin levels in normal subjects.

A "patient" is a mammal, preferably a human, but can also be a companion animal such as dogs or cats, or farm animals such as horses, cattle, pigs, or sheep.

A patient in need of treatment or prevention for a bone disease includes a patient known or suspected of having or being at risk of developing a bone disease. Such a patient in need of treatment could be, e.g., a person known to have osteoporosis. A patient at risk of developing a bone disease could include the elderly, post-menopausal women, patients being treated with glucocorticoids, patients being treated with SSRIs, and patients having bone density outside the normal range. Other persons in need of treatment or prevention by the methods of the present invention include persons who are known to be in need of therapy to decrease serum serotonin levels in order to treat or prevent a bone disease, e.g., osteoporosis. Such persons might include persons who have been identified as having a serum serotonin level that is about 25% or more above that of serum serotonin levels in normal subjects.

A patient in need of treatment or prevention for a bone disease (e.g., a low bone mass disease) by the methods of the present invention does not include a patient being treated with a TPH1 inhibitor, another agent that decreases serum serotonin levels, or a serotonin HT1B antagonist where the patient is being treated with the TPH1 inhibitor, other agent that decreases serum serotonin levels, or serotonin HT1B antagonist for a purpose other than to treat a bone disease. Thus, a patient in need of treatment or prevention for a bone disease by the methods of the present invention does not include a patient being treated with a TPH1 inhibitor for the purpose of treating chemotherapy-induced emesis, carcinoid syndrome, or gastrointestinal disorders such as irritable bowel syndrome.

A patient in need of treatment or prevention for a low bone mass disease by the methods of the present invention does not include a patient being treated with a TPH1 inhibitor for the purpose of treating gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional anorectal disorders, functional bloating, functional dyspepsia, functional gallbladder disorders, irritable bowel syndrome (IBS; including IBD-d, IBS-c and IBS-a), lactose intolerance, MEN types I and II, nausea, Ogilvie's syndrome, Pancreatic Cholera Syndrome, pancreatic insufficiency, pheochromacytoma, scleroderma, somatization disorder, sphincter of Oddi disorders, ulcerative colitis, and Zollinger-Ellison Syndrome. A patient in need of treatment or prevention for a low bone mass disease by the methods of the present invention does not include a patient being treated with a TPH1 inhibitor for the purpose of treating these diseases and disorders.

A patient in need of treatment or prevention for a low bone mass disease by the methods of the present invention also does not include a patient being treated with a TPH1 inhibitor for the purpose of treating the following diseases and disorders: cardiovascular and pulmonary diseases and disorders, such as acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), serotonin syndrome, and subarachnoid hemorrhage.

A "TPH1 inhibitor" is a substance that reduces the amount of 5-hydroxytryptophan produced from tryptophan by TPH1 in a suitable assay, as compared to the amount of 5-hydroxytryptophan produced from tryptophan by TPH1 in the assay in the absence of the substance. Preferably, the decrease is at least about 10%. Assays for determining the level of TPH1 inhibition of an agent are described in U.S. Patent Application Publication US 2009/0029993.

A "TPH2 inhibitor" is a substance that reduces the amount of 5-hydroxytryptophan produced from tryptophan by TPH2 in a suitable assay, as compared to the amount of 5-hydroxytryptophan produced from tryptophan by TPH2 in the assay in the absence of the substance. Preferably, the decrease is at least about 10%.

Techniques for measuring bone mass include those techniques well known to those of skill in the art including, but not limited to, skeletal X-rays, which show the lucent level of bone (the lower the lucent level, the higher the bone mass); classical bone histology (e.g., bone volume, number and aspects of trabiculi/trabiculations, numbers of osteoblast relative to controls and/or relative to osteoclasts); and dual energy X-ray absorptiometry (DEXA) (Levis & Altman, 1998, Arthritis and Rheumatism, 41:577-587) which measures bone mass and is commonly used in osteoporosis. BFR means bone formation rate. Any method known in the art can be used to diagnose a person at risk of developing high or low bone mass diseases, or to determine the efficacy of drug therapy.

"Selective serotonin reuptake inhibitors (SSRIs)" refers to a class of antidepressants used in the treatment of depression, anxiety disorders, and some personality disorders. They are also typically effective and used in treating premature ejaculation problems. SSRIs increase the extracellular level of the neurotransmitter serotonin by inhibiting its reuptake into the presynaptic cell, increasing the level of serotonin available to bind to the postsynaptic receptor. They have varying degrees of selectivity for the other monoamine transporters, having little binding affinity for the noradrenaline and dopamine transporters. The first class of psychotropic drugs to be rationally designed, SSRIs are the most widely prescribed antidepressants in many countries. SSRIs include: citalopram (CELEXA®, CIPRAMIL®, EMOCAL®, SEPRAM®, SEROPRAM®); escitalopram oxalate (LEXAPRO®, CIPRALEX®, ESERTIA®); fluoxetine (PROZAC®, FONTEX®, SEROMEX®, SERONIL®, SARAFEM®, FLUCTIN® (EUR), FLUOX® (NZ)); fluvoxamine maleate (LUVOX®, FAVERIN®); paroxetine (PAXIL®, SEROXAT®, AROPAX®, DEROXAT®, REXETIN®, XETANOR®, PAROXAT®); sertraline (ZOLOFT®, LUSTRAL®, SERLAIN®), and dapoxetine (no known trade name).

Lrp5 Regulates Bone Development Through More than One Mechanism

The extreme conservation of gene function between mouse and human when it comes to skeletal biology explains why skeletal biology, and especially the study of bone remodeling and homeostasis, has been profoundly influenced by mouse and human genetic studies. Although gene inactivation experiments in mice or molecular cloning of disease genes in humans were designed initially to identify genes important during embryonic development, results of these studies went further than this initial goal by also shedding new light on the molecular bases of skeletal biology after birth. Among the genes identified either through gene deletion experiments or through human genetic studies that turned out to be important for the maintenance of bone mass in adults, one can cite the vitamin D receptor, Interleukin 6, Estrogen receptor a and LDL receptor related protein 5 (Lrp5) (Gong et al., 2001, Cell 107: 513-523; Boyden et al., 2002, N. Engl. J. Med. 346: 1513-1521; Yoshizawa et al., 1997, Nat. Genet. 16: 391-396; Ohshima et al., 1998, Proc. Natl. Acad. Sci. USA 95:822-826; Windahl et al., 2002, Trends Endocrinol. Metab. 13:195-200).

The identification of Lrp5 as a regulator of post-natal bone formation is one of the most vivid examples of how developmental studies can profoundly affect the understanding of physiology because this receptor is expressed during development but its function only becomes apparent post-natally. Indeed, loss-of-function mutations in Lrp5 cause osteoporosis pseudoglioma syndrome (OPPG) in humans, a pediatric disease, and gain-of-function mutations in Lrp5 cause high bone mass, a phenotype most often appearing only in adolescents and persisting into adulthood (Gong et al., 2001, Cell 107: 513-523; Boyden et al., 2002, N. Engl. J. Med. 346: 1513-1521; Johnson et al., 1997, Am. J. Hum. Genet. 60:1326-1332). Likewise, skeletogenesis is normal in Lrp5−/− mice and their low bone mass phenotype only develops post-natally (Kato et al., 2002, J. Cell. Biol. 157: 303-314).

The LDL receptor related protein 5 (LRP5) is required for normal bone mass, and a low bone mass phenotype is caused by Lrp5 inactivation in humans and mice (Gong et al., 2001, Cell 107:513-523; Kato et al., 2002, J. Cell. Biol. 157: 303-314). Lrp5−/− mice have low bone mass with no change in osteoclast surface but decreased osteoblast numbers. Realtime PCR analysis of Lrp5−/− molecular signature shows that Lrp5−/− osteoblasts do not show changes in osteoblast-specific gene expression but have decreased expression of cyclin genes (FIG. 1).

Lrp5 and its closest relative Lrp6 are the vertebrate homologues of the *Drosophila* gene arrow that encodes a surface receptor functioning as a co-receptor for Wingless, the *drosophila* homologue of the Wnt proteins (Wehrli et al., 2000, Nature 407:527-530; Tamai et al., 2000, Nature 407:530-535). In vertebrate cells, Wnt signaling is mainly mediated by β-catenin. Upon binding of a Wnt ligand to its receptor, β-catenin is translocated to the nucleus where it cooperates with Lef/Tcf transcription factors to activate gene expression (Logan et al., 2004, Annu. Rev. Cell Dev. Biol. 20:781-810; Mao et al., 2001, Mol. Cell, 7:801-809). According to this canonical model, co-transfection of Lrp5 increases the ability of Wnt proteins to enhance the activity of a Tcf-dependent promoter such as the TopFlash (Gong et al., 2001, Cell 107: 513-523; Boyden et al., 2002, N. Engl. J. Med. 346:1513-1521; Mao et al., 2001, Mol. Cell, 7:801-809). Together, the homology of sequence between arrow and Lrp5 and the ability of Lrp5 to favor Wnt signaling through its canonical pathway have led to a model whereby Wnt signaling would regulate bone mass post natally and during adulthood by regulating osteoblast proliferation and function. There is no reason to question the notion that Lrp5 may be a co-receptor for Wnts and that Wnt signaling is involved in the regulation of bone formation (Glass et al., 2005, Dev. Cell 8:751-764; Holmen et al., 2005, J. Biol. Chem. 280:21162-21168; Day et al., 2005, Dev. Cell, 8:739-750; Hu et al., 2005, Development 132:49-60). Nevertheless, there may be additional mechanisms that explain the bone abnormalities observed in either Lrp5 loss- or gain-of-function models.

Lrp5 Regulates Bone Mass in the Periphery Through Serotonin

TPH1 encodes the first enzyme in the biochemical pathway resulting in serotonin synthesis outside the central nervous system. It is viewed as a cell-specific gene mostly expressed in the enterochromaffin cells of the duodenum (Gershon & Tack, 2007, Gastroenterology, 132:397-414). By contrast, serotonin synthesis in the brain relies on TPH2, which is encoded by a different gene expressed in the central nervous system (CNS).

In an effort to elucidate the molecular mechanisms whereby Lrp5 inactivation affects bone formation, a microarray analysis in WT and Lrp5−/− bones was performed. Tryptophan hydroxylase 1 (TPH1) was identified as the gene most highly over expressed in Lrp5−/− bones having low bone mass disease. This result was surprising since it is the opposite of what would be expected given the role of serotonin in the brain, where it increases bone mass. Remarkably, TPH1 expression was normal in mice lacking β-catenin in osteoblasts only (Glass et al., 2005, Dev. Cell 8:751-764).

Figure 7:
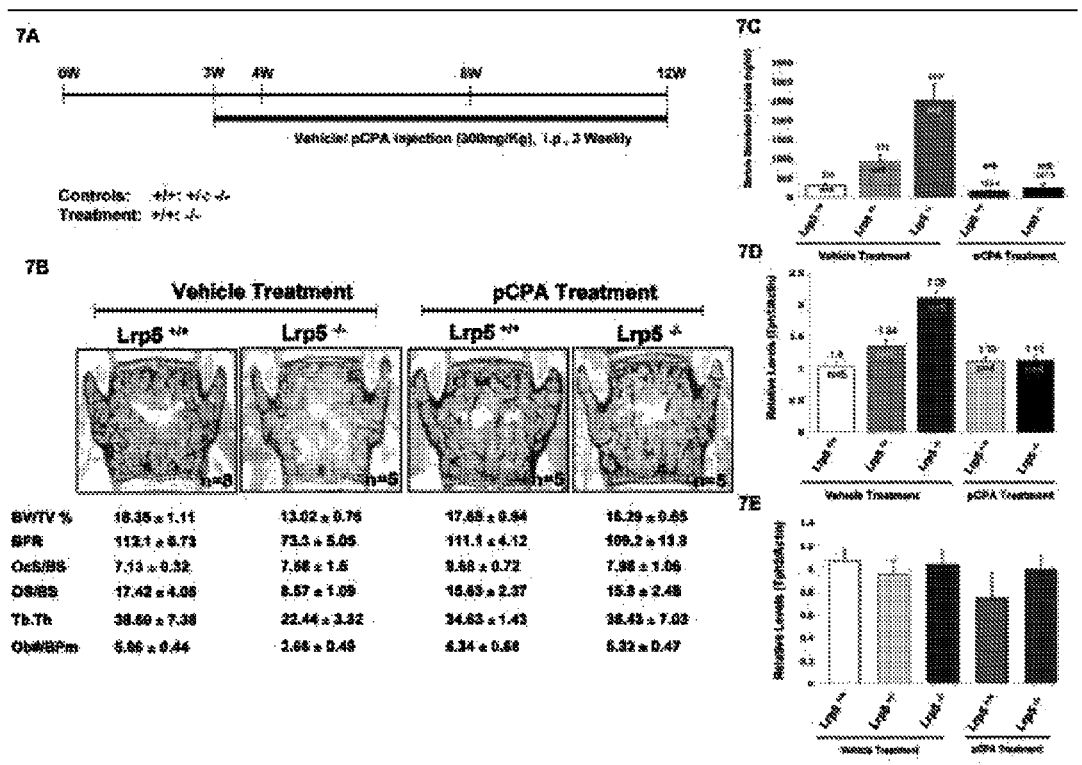
FIG. 7. Tryptophan hydroxylase inhibitor (pCPA) treatment normalizes serum serotonin levels and corrects bone abnormalities observed in Lrp5−/− mice. Treatment regimen for the pCPA treatment (A), histomorphometric analysis of bone phenotype (B), serum serotonin levels (C), gut Tph1 expression levels (D), brain Tph2 expression upon vehicle and pCPA treatment.

It was shown that TPH1 is overexpressed not only in bone, but also in the duodenum in Lrp5−/− mice, where TPH1 expression is more than 1300-fold higher than in osteoblasts. It was further discovered that serum serotonin levels are normal in newborn Lrp5−/− mice but increase steadily with age as their bone phenotype develops. This is consistent with the fact that the low bone mass phenotype in Lrp5−/− mice is not present at birth but appears later during development. Further discoveries showed that treating Lrp5−/− mice with an inhibitor of serotonin synthesis called pCPA corrects their low bone phenotype (FIG. 7). Finally, it was discovered that TPH1 expression is increased in aging animals, i.e., when bone mass is well-known to decrease. Based on these and additional data described below, it can be conclude that LRP5, through yet unknown mechanisms, is a negative regulator of serotonin synthesis in the duodenum, and that increasing serum serotonin signaling negatively impacts osteoblast proliferation and function.

Serotonin, a Multifaceted Molecule

Serotonin (5-hydroxytryptamine, 5-HT) is a biogenic amine that functions both as a neurotransmitter in the mammalian central nervous system and as a hormone in the periphery, where most of it is produced (Gershon et al., 1990, Neuropsychopharmacology, 3:385-395.). Serotonin is generated through an enzymatic cascade in which L-tryptophan is converted into L-5-hydroxytryptophan by an enzyme called tryptophan hydroxylase (TPH). This intermediate product is then converted to serotonin by an aromatic L-amino acid decarboxylase. There are two TPH encoding genes, TPH1 and TPH2, which are 71% identical in amino acid sequence and about 90% similar in the catalytic domain. While TPH1 controls serotonin synthesis in the periphery, TPH2 is responsible for serotonin synthesis in the brain (Walther et al., 2003, Science 299:76). Given that serotonin cannot cross the blood-brain barrier, these two genes are therefore solely responsible for regulating the level of this molecule in the periphery and in the brain, respectively. As a consequence, designing TPH1 inhibiting compounds that cannot cross the blood brain barrier is one of the ways to achieve selective inhibition of TPH1 in the periphery and decrease serotonin levels in this physiologic compartment.

TPH1 is expressed almost exclusively in cells of the duodenum, and it is responsible for the synthesis of peripheral serotonin, which represents 95% of total serotonin (Gershon & Tack, 2007, 132:397-414). TPH1 expression in any tissues other than duodenum is at least 100-1000 fold lower. Thus, TPH1 can be viewed as a duodenum-specific gene and peripheral serotonin production as a duodenum-specific process.

Besides its role as a neuromediator, and because of its abundance in the general circulation, serotonin has been implicated in a variety of developmental and physiological processes in peripheral tissues, including heart development, gastrointestinal movement, liver regeneration and mammary gland development (Lesurtel et al., 2006, Science, 312:104-107; Matsuda et al., 2004, Dev. Cell, 6:193-203; Nebigil et al., 2000, Proc. Natl. Acad. Sci. USA 97:9508-9513). To carry out its functions, serotonin can bind to at least 14 receptors, most of them being G-protein coupled receptors (GPCRs). One or several serotonin receptors are present in most cell types, including osteoblasts (Westbroek et al., 2001, J. Biol. Chem. 276:28961-28968).

Type 1 Collagen, Osteocalcin, Regulatory Genes Affecting Osteoblast Differentiation and/or Extracellular Matrix Protein Synthesis (Runx2 and Osterix and Atf4) and Osteoclast Differentiation (RankL and Osteoprotegrin) are Normal in LrpS-Deficient Mice Lrp5−/− mice are indistinguishable by all accounts from WT mice at birth, but afterward progressively develop a significant low bone mass phenotype (Kato et al., 2002, J. Cell. Biol. 157: 303-314). Histological and histomorphometric analyses established that this low bone mass phenotype is due to a decrease in bone formation while bone resorption is unaffected. Importantly, osteoblast differentiation is not affected in the mutant mice while osteoblast proliferation is decreased two fold in the absence of Lrp5. See FIG. 1, which shows that Lrp5−/− mice have low bone mass (A) with no change in osteoclast surface (B) but have decreased osteoblast numbers (C).

Real-Time PCR Analysis of Lrp5−/− Molecular Signature.

To delineate the molecular signature of the disruption of Lrp5 signaling, the expression of multiple genes characterizing either the osteoblast lineage or determining cell proliferation was studied using Lrp5−/− mice (Kato et al., 2002, J. Cell. Biol. 157: 303-314). The expression of genes particularly relevant to bone formation was first analyzed. Expression of type I collagen and Osteocalcin, two genes highly expressed in osteoblasts, is normal in Lrp531 /− bones (data not shown). This finding is important as it establishes that the bone phenotype of the Lrp5−/− mice is not caused by a defect in type I collagen synthesis, the main constituent of the bone extracellular matrix (ECM). Expression of regulatory genes affecting osteoblast differentiation and/or extracellular matrix protein synthesis was also studied. Expression of Runx2 and Osterix and Atf4, the three known osteoblast-specific transcription factors, was unaltered in Lrp5−/− bones (FIG. 1D). Likewise, expression of RankL and Osteoprotegerin (OPG), two regulators of osteoclast differentiation expressed by osteoblasts is unaffected by Lrp5 deletion (FIG. 1D). This latter feature distinguishes Lrp5−/− from β-catenin osteoblast-specific deficient (βcatob−/−) bones (Glass et al., 2005, Dev. Cell 8:751-764; Holmen et al., 2005, J. Biol. Chem. 280:21162-21168).

Given the decrease in osteoblast proliferation characterizing Lrp5−/− bones, the expression of marker genes of cell cycle progression was also studied. Expression of Cyclin D1, D2 and E1, three genes necessary for the transition from the G1 to S phase of the cell cycle, was decreased in the Lrp5−/− bones (FIG. 1E). Based on these results, it appears that at the molecular level the low bone mass phenotype caused by the absence of Lrp5 is purely a cell proliferation defect while expression of type I collagen, the main protein constituent of the bone extracellular matrix (ECM), and of all 3 known osteoblast-specific transcription factors is normal.

Low Bone Phenotype in Lrp5−/− Mice is not Due to Abnormal Wnt Signaling

Figure 2:
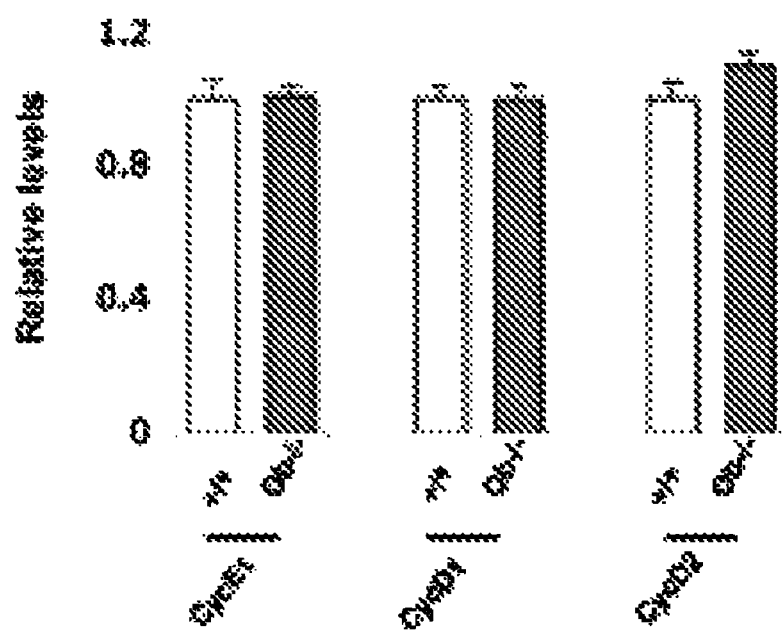
FIG. 2. Real-time PCR analysis of cell cycle marker genes in β-cat$_{ob}$−/− bones (ob−/−).

Given the sequence homology and convincing experimental arguments suggesting that Lrp5 could be a co-receptor for Wnt and may be part of the Wnt canonical signaling pathway, whether the bone phenotype of Lrp5−/− mice was due to abnormal Wnt signaling was investigated. To that end, mice lacking β-catenin in osteoblasts only were analyzed (Glass et al., 2005, Dev. Cell 8:751-764). It had been shown earlier that mice lacking β-catenin only in osteoblasts developed a low bone mass phenotype and that this phenotype was caused by a totally different mechanism than the one operating in the Lrp5−/− mice. Indeed, β-cat$_{ob}$−/− mice have a normal number of osteoblasts, an increase of the number of osteoclasts and an increase in elimination of deoxypyridinoline, abnormalities that are secondary to a decrease in OPG expression (Glass et al., 2005, Dev. Cell 8:751-764). In addition, unlike in Lrp5−/− bones, expression of the cell cycle markers Cyclin D1, D2 and E1 was normal in the in β-cat$_{ob}$−/− bones (FIG. 2). Thus, the cellular and molecular bases of the β-cat$_{ob}$−/− and Lrp5−/− mice bone phenotype appear to be quite different. Although these unexpected results do not rule out that Lrp5 could act as a Wnt co-receptor, there was still a possibility that other mechanisms could explain how the loss of Lrp5 could affect bone formation so specifically. To that end, a micro-array analysis looking for genes abnormally expressed in Lrp5−/− compared to WT bones was performed.

TPH1 is Overexpressed in Bone and Duodenum in Lrp5−/− Mice

Figure 3:
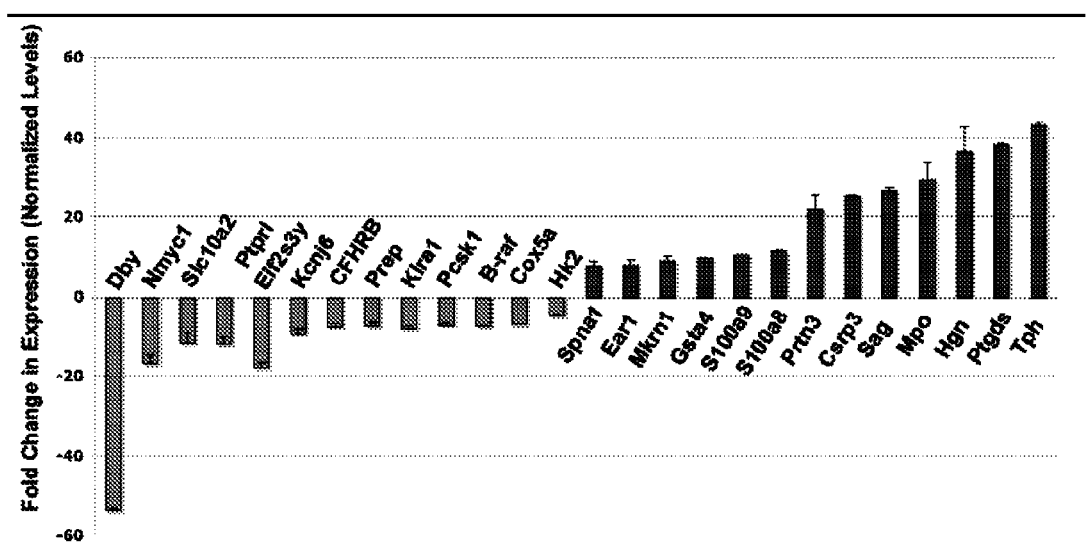
FIG. 3. Microarray analysis of Lrp5−/− bones reveals an increased expression of Tryptophan hydroxylase 1 (Tph1) gene expression compared to wt bones. Gray and black bars indicate a decrease and an increase in gene expression, respectively. Genes including and to the left of Hk2 showed decreased expression while genes including and to the right of Spna1 showed increased expression.

A microarray analysis of Lrp5−/− bones surprisingly showed that one of the genes most highly over expressed was TPH1 (FIG. 3). It is important to emphasize that TPH1 expression is normal in β-cat$_{ob}$−/− bones and osteoblasts, further underscoring the molecular differences that exist between these two mutant mouse strains. Given the rather confined pattern of expression of TPH1 in WT mice, where it is restricted to the duodenum, its overexpression in Lrp5−/− bones was surprising and raised the question whether it was an osteoblast-specific feature.

Figure 4:
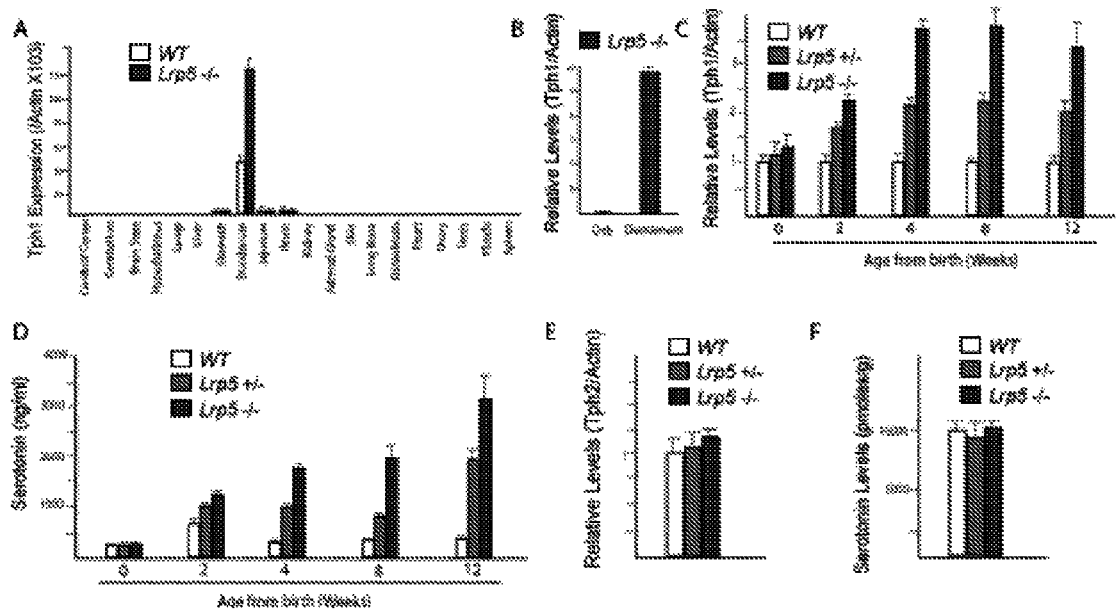
FIG. 4. Tph1 expression is increased in the duodenum of Lrp5−/− mice (A). Tph1 expression is 1000 fold higher in duodenum than in bone in Lrp5−/− mice (B). Tph1 expression in duodenum (C) and serum serotonin levels (D) increase progressively with age in Lrp5−/− mice. Neither Tph2 expression nor serotonin levels are altered in the brain of Lrp5−/− mice (E and F).
Figure 5:
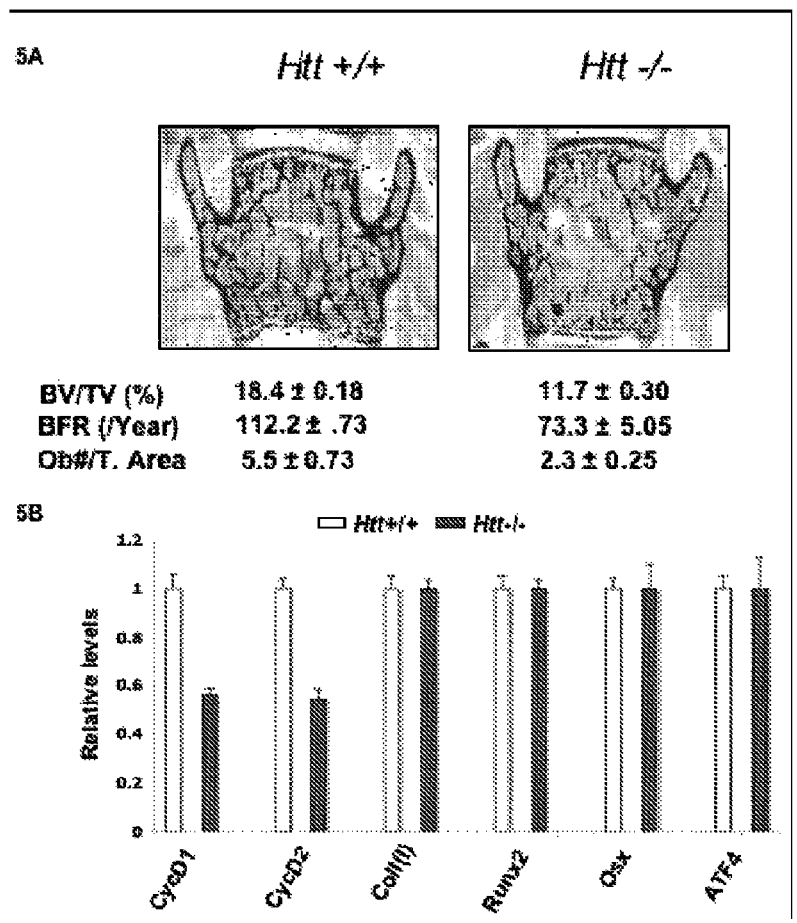
FIG. 5. 5Htt−/− mice have low bone mass and decreased osteoblast numbers (A). Realtime PCR analysis of gene expression in bone revealed a decreased expression of cyclins in 5Htt−/− mice while no changes in the expression of osteoblast differentiation markers or type I collagen genes can be detected (B).
Figure 6:
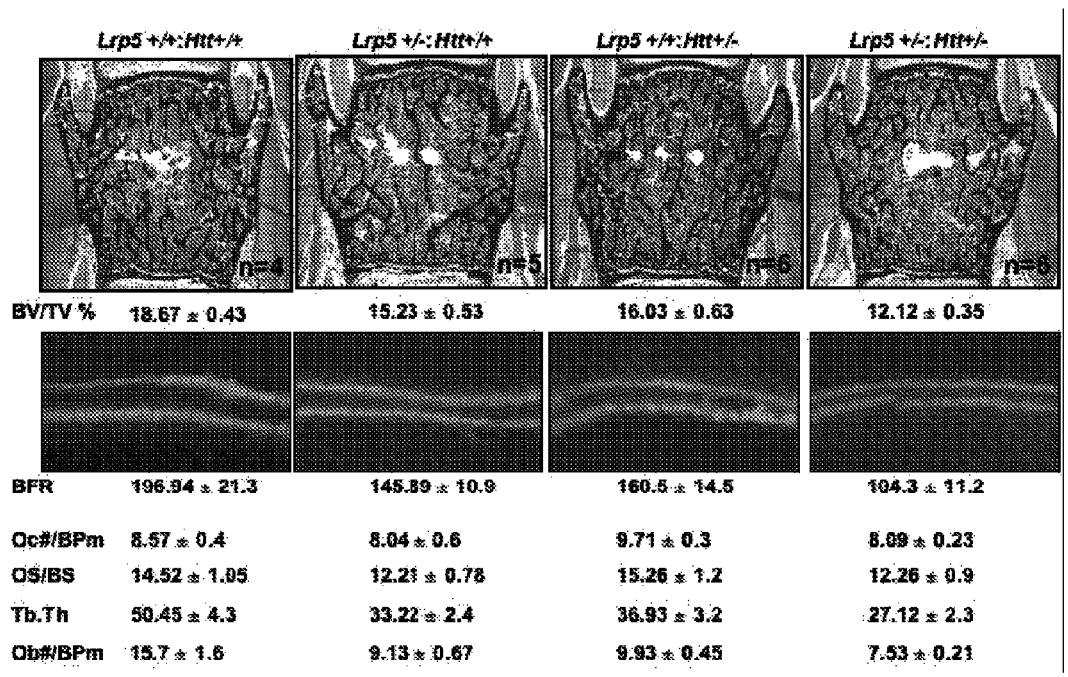
FIG. 6. Histologic and histomorphometric comparison of Lrp5/5Htt (Htt) compound mice. Lrp5+/−; Htt+/− double heterozygous mice have a more severe decrease in bone mass than the Lrp5+/− or 5Htt+/− single heterozygous mice. This is also true for the decrease in osteoblast numbers.

To answer this question, TPH1 expression in all tissues of WT and Lrp5−/− mice was analyzed by qPCR. It was found that TPH1 expression was also increased 3 fold in duodenum of Lrp5−/− compared to WT mice (FIG. 4A). However, TPH1 expression remained more than 1300 fold higher in duodenum than in osteoblasts in Lrp5−/− mice (FIG. 4B). These latter data suggested for the first time that the bone phenotype observed in Lrp5−/− mice may primarily have a gut origin. The increase in expression of TPH1 was also observed, albeit as expected to a lower level, in Lrp5+/− mice (FIG. 4C). This is an important observation since heterozygous Lrp5+/− mice also have a low bone mass phenotype. Importantly, in agreement with the absence of a bone phenotype in newborn Lrp5−/− mice, TPH1 expression was not elevated in newborn mice (FIG. 4C). The changes in TPH1 expression were reflected in increased serum serotonin levels in both Lrp5+/− and Lrp5−/− mice (FIG. 4D); which were absent at birth but present at 2, 4 and 8 weeks of age. Moreover these changes preceded the appearance of the bone phenotype in Lrp5−/− mice.

By contrast, the expression of TPH2 in the brain was not affected in Lrp5−/− mice and serotonin content in the brain was similar in WT and Lrp5−/− mice (FIGS. 4E and 4F). This observation is consistent with the fact that serotonin does not cross the blood brain barrier (Mann et al., 1992, Arch. Gen. Psychiatry, 49:442-446) and indicates that the link between Lrp5 function and serotonin biology has to be with peripheral serotonin.

Expression of the TPH1 gene was decreased compared to wild type (WT) in mice engineered with a mutation causing high bone mass in humans in one allele (Lrp5+/act duo) or both alleles (Lrp5 act duo) of the mouse Lrp5 gene specifically in cells of the duodenum. RNA was extracted from duodenum of one-month-old mice and expression of the TPH1 gene quantified by real-time PCR (FIG. 12).

TABLE 1

|  | WT | Lrp5 +/act duo | Lrp5 act duo |
|---|---|---|---|
| Relative TPH1 expression | 1 | 0.77 ± 0.000 | 0.54 ± 0.005 |

Figure 12:
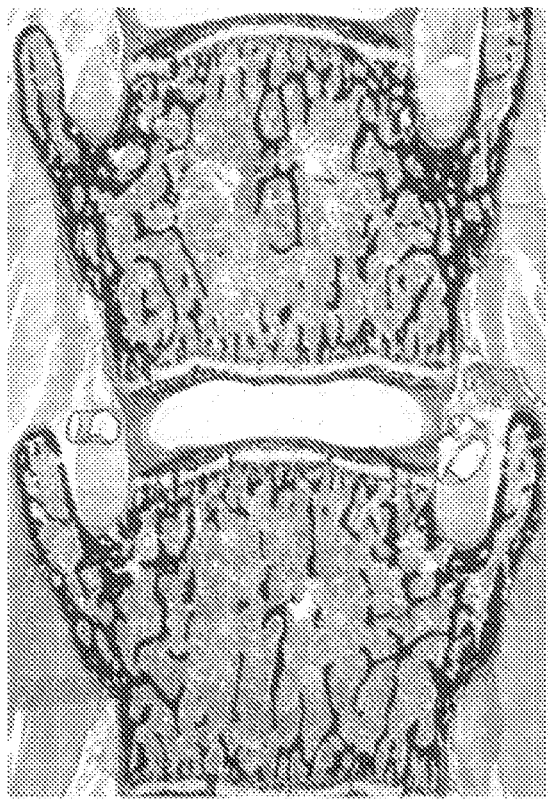
FIG. 12. Mice engineered to express in both alleles of their Lrp5 genes of their duodenal cells a mutation that in humans leads to high bone mass show a higher bone mass than wild-type (WT) mice. Vertebrae were embedded in plastic medium, sectioned at 5 micrometers and stained with the von Kossa/Van gieson reagent. The bone matrix was stained in black.
Figure 12:
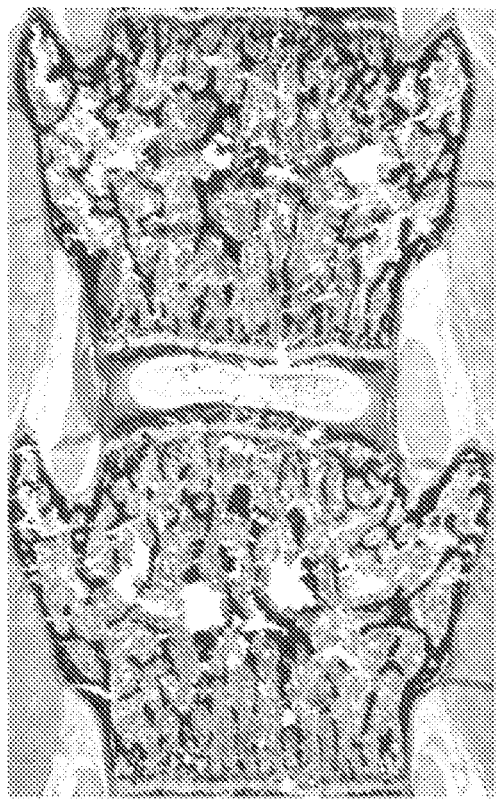

Mice engineered with a mutation causing high bone mass in human in the Lrp5 gene specifically in cells of the duodenum (Lrp5 act duo) show a higher bone mass than wild type mice (FIG. 12).

Taken together, the results of these analyses indicated that the increase in TPH expression caused by Lrp5 deficiency was restricted to TPH1 (and therefore to peripheral serotonin) and that it occurs both in osteoblasts and duodenal cells although its expression is at least 1300-fold higher in duodenum. This result raises two questions: is the increase in serum serotonin the cause of the Lrp5−/− mice bone phenotype and is this an endocrine effect mediated by the production of serotonin by duodenal cells and/or an autocrine effect related to the local production of serotonin by osteoblasts?

Lrp5−/− and 5Htt−/− Mice have Identical Bone Phenotypes

If the bone phenotype of the Lrp5−/− mice is secondary to an increase in the level of serum serotonin, then a mouse model characterized by an increase in serum serotonin should have not only the same histological bone phenotype as the Lrp5−/− micc but also the same molecular signature defined previously, i.e., decreased cyclin gene expression and normal type I collagen expression (FIG. 1). This is what was observed.

The Serotonin Synthesis Inhibitor (pCPA) Rescues the Bone Phenotype of Lrp5−/− Mice Consistent with the conclusion that the increase in serum serotonin level is responsible fully or partly for the bone phenotype of the Lrp5−/− mice is the discovery that pCPA, a serotonin synthesis inhibitor (Eldridge et al., 1981, Ann. Rev. Physiol. 43:121-135), prevented the appearance of the Lrp5−/− bone phenotype by decreasing serotonin production. WT and Lrp5−/− mice were treated with 300 mg/kg pCPA intraperitoneally three times per week, from 3 weeks to 12 weeks of age (FIG. 7A) and the changes in serum serotonin levels, TPH1 expression in gut and TPH2 expression in brain stem were analyzed. Bone histomorphometry was also performed. As shown in FIG. 7B, pCPA treatment corrected the bone abnormalities observed in Lrp5−/− mice without overtly affecting bone mass in WT mice. This rescue of the Lrp5−/− phenotype was achieved by normalization of the gut TPH1 mRNA and of serum serotonin levels (FIGS. 7C and 7D). Brain TPH2 mRNA levels were not affected in the treated mice, further demonstrating that the phenotype observed in Lrp5−/− bones is directly caused by changes in serum, not brain, serotonin levels.

Serotonin Binds to Specific Serotonin Receptors in Osteoblasts

From the working hypothesis that Lrp5 acts on bone formation through serum serotonin, a third inference was tested: osteoblasts should express some serotonin receptors, and serotonin treatment of osteoblasts should blunt the expression of Cyclin D1, D2 and E1 without affecting the expression of α(I) collagen, Runx2 or Osteocalcin. To address the first part of this point, the expression of each of the known serotonin receptors was analyzed by qPCR in WT osteoblasts. The expression of three different serotonin receptors in osteoblasts, all belonging to the G-protein coupled receptor superfamily was detected (Noda et al., 2004, Mol. Neurobiol. 29:31-39). HT1B was the most highly expressed receptor. It is coupled to $G_i$-type G proteins and inhibits adenylyl cyclase activity. HT2B is the second most abundant receptor and is coupled to the G proteins that activate a phosphatidyl-inositolcalcium second messenger system. Lastly, HT2A is the third receptor significantly expressed in osteoblasts. Like HT2B, it is coupled to the G proteins that activate a phosphatidylinositol-calcium second messenger system. Remarkably, HT1B, the most highly expressed serotonin receptor in osteoblasts, is also more highly expressed in these cells than in any other cells. Thus, there is at least a partially cell-specific signaling pathway occurring in osteoblasts that could be able to specifically transduce serotonin signaling in these cells. See FIG. 8 which shows real-time PCR analysis of the expression of known serotonin receptors expression in WT osteoblasts (A) and of the expression of cyclins and osteoblast-specific genes in primary osteoblasts treated with serotonin or vehicle (B).

To test whether serotonin regulates the expression of cyclins in osteoblasts, a real-time PCR analysis of cyclin expression in primary osteoblasts treated with serotonin or vehicle was performed. As shown in FIG. 8B, expression of Cyclin D1 and D2 was decreased in the presence of serotonin. In contrast, expression of Runx2, Osteocalcin and Type I collagen was not modified (FIG. 8B). That the molecular signature of serotonin treatment of osteoblasts is similar to the one displayed in absence of LrpS further strengthens the hypothesis of a functional link between Lrp5 and serotonin signaling in osteoblasts.

Figure 8:
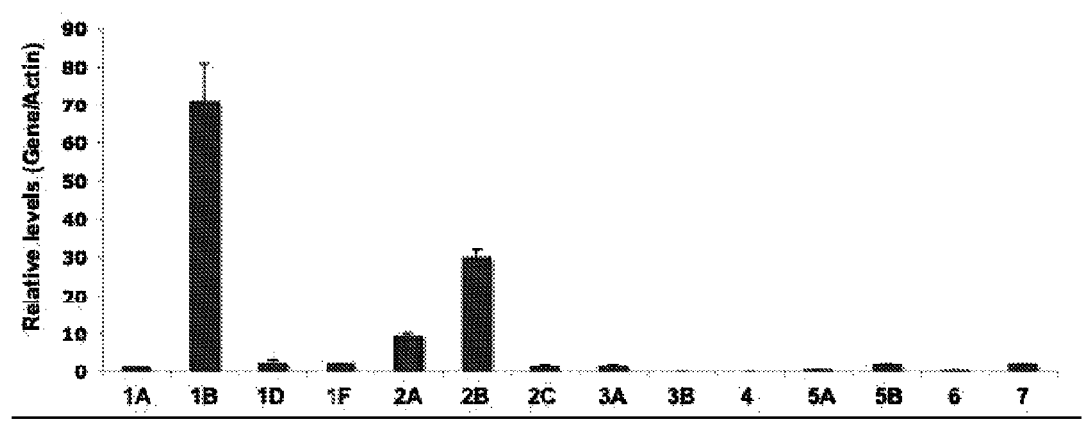
FIG. 8. Real-time PCR analysis of the expression of known serotonin receptors expression in WT osteoblasts (A) and of the expression of cyclins and osteoblast-specific genes in primary osteoblasts treated with serotonin or vehicle (B).
Figure 8:
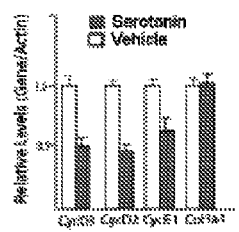
Figure 9:
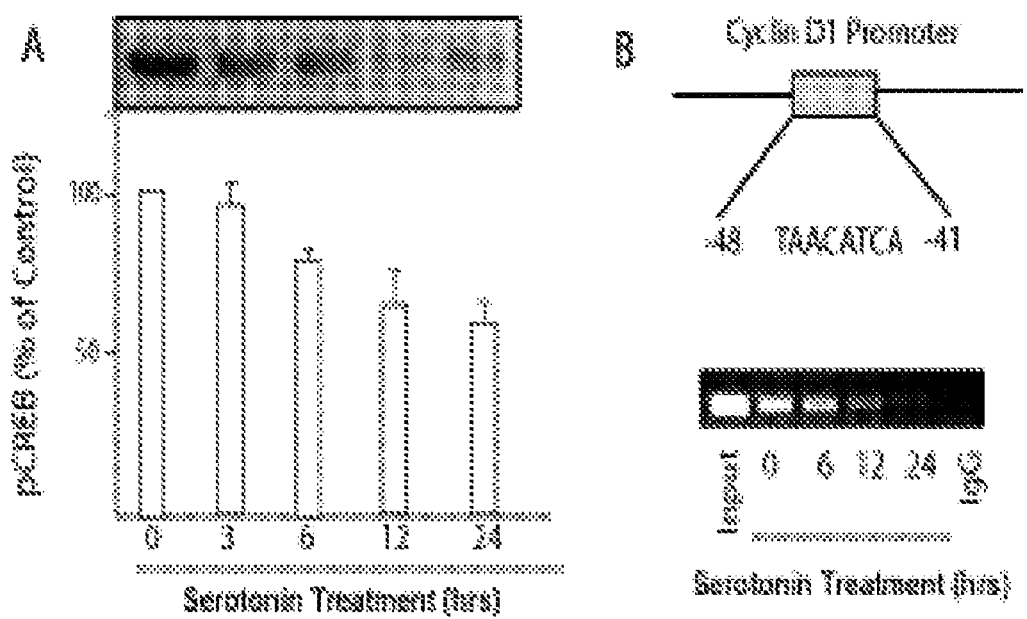
FIG. 9. Western blot analysis of CREB phosphorylation (A) and ChIP analysis of CREB binding to the Cyclin D1 promoter (B) in primary osteoblasts treated with serotonin for the indicated times.

Decreased expression of Cyclin D1 is a major feature of both LrpS deficiency and serotonin treatment of osteoblasts (FIGS. 1 and 8). One transcription factor that is known to modulate the expression of cyclin genes and is expressed in osteoblasts is CREB (Fu et al., 2005, Cell 122:803-815). Therefore, whether serotonin could decrease CREB activity in these cells was tested. As shown in FIG. 9A, serotonin treatment significantly decreased CREB phosphorylation in primary osteoblasts. Furthermore, a CREB binding site in the Cyclin D1 mouse promoter was identified and it was shown using ChIP assays that serotonin decreased binding of CREB to this promoter (FIG. 9B). These two observations raise the hypothesis that CREB could be mediating serotonin action on osteoblasts.

TPH1 Expression is Increased in Aging Animals

Figure 10:
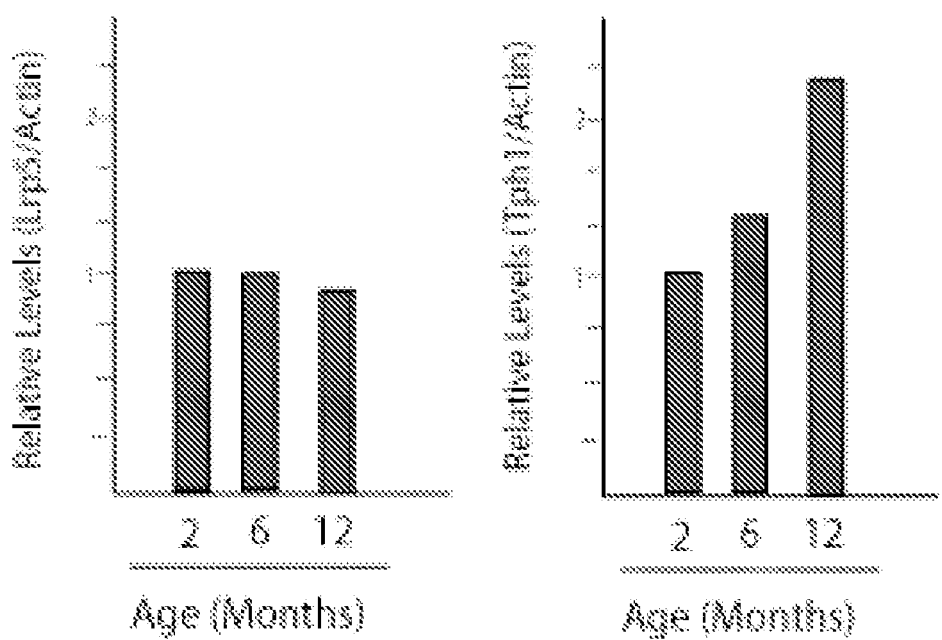
FIG. 10. Real-time PCR analysis of the expression of Tph1 (A) and Lrp5 (B) in duodenum of WT mice at the indicated ages.

It has been shown in *C. elegans* that TPH1 expression increases with age (Murakami et al., 2007 Feb. 28 [Epub ahead of print], Neurobiol Aging). To test if this was also the case in mammals, TPH1 expression in aging mice was analyzed. Using real time PCT, it was shown that, while expression of Lrp5 remained stable with age, expression of TPH1 doubled in 1 year-old compared to 2 month-old mice (FIG. 10). Since serum serotonin acts as a negative regulator of bone formation, such an increase in TPH1 expression with age exacerbates the bone loss associated with aging and therefore is a target for therapeutic intervention for age-related bone loss.

TPH1 Inhibitors Prevent and Treat Osteoporosis in Mice and Rats

Figure 14:
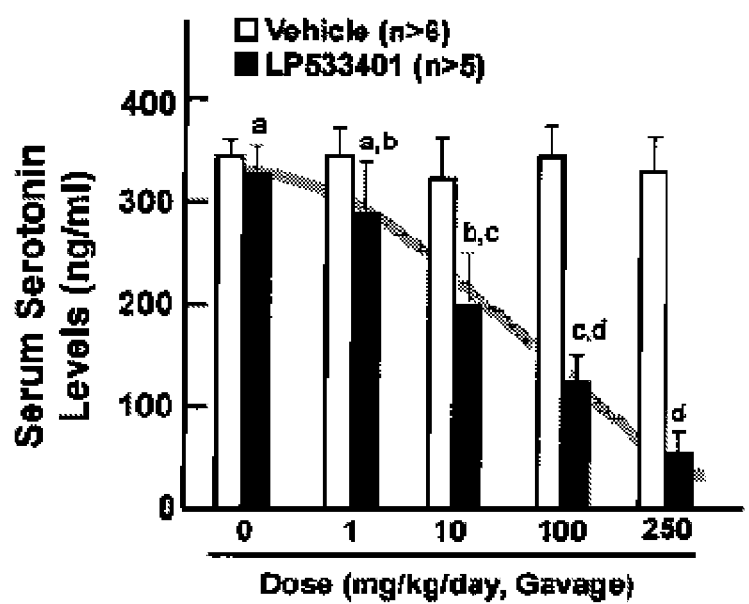
FIG. 14. Dose response of serum serotonin levels in wild-type mice for the Tph1 inhibitor LP-533,401.
Figure 15:
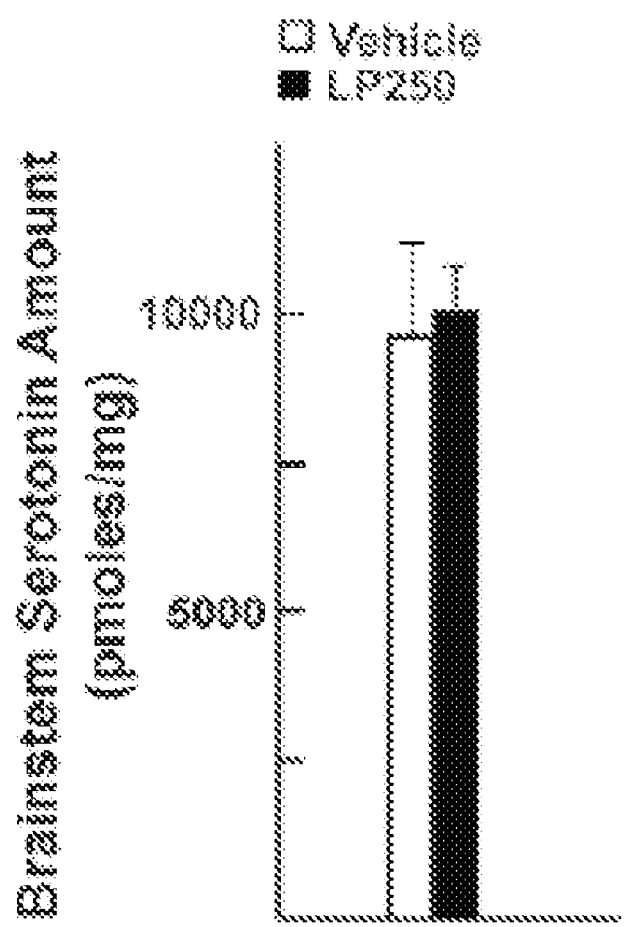
FIG. 15. HPLC analysis of serotonin content in the brain of wild-type mice that received vehicle or LP-533,401 (250 mg/kg, orally) for 1 day.

There was a dose-dependent decrease in serum serotonin levels in WT mice fed with increasing amounts of LP-533, 401 (FIG. 14). This decrease in serum serotonin levels reached 70% of control values when using 250 mg/kg of the compound while no change in brain serotonin content was observed (FIG. 15). To further demonstrate the therapeutic relevance of TPH1 inhibitors for the treatment and prevention of low bone mass diseases, LP-533,401 was administered to ovariectomized rodents. Ovariectomized rodents present, as post-menopausal women do (Rodan & Martin, 2000, Science 289:1508-1514), a marked increase in bone resorption not compensated by a similar increase in bone formation. Using this model, it was possible to demonstrate that oral administration once daily for up to 6 weeks of LP-533,401 prevents the development of osteoporosis and fully rescues pre-existing osteoporosis, in a dose-dependent manner, in ovariectomized mice and rats due to an increase in bone formation.

Figure 16:
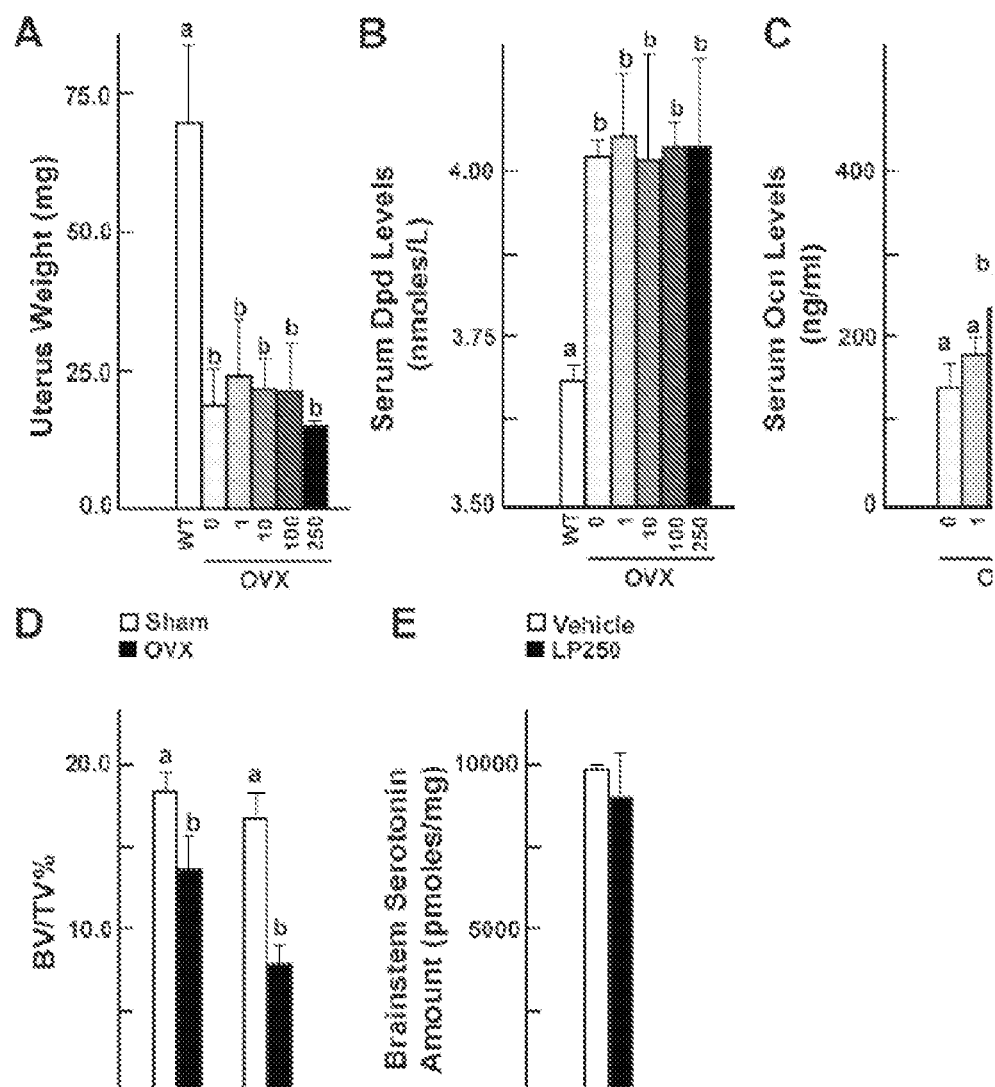
FIG. 16. (A-C) Uterus weight (A), serum deoxypyridinoline (Dpd) (B) and osteocalcin serum levels (C) in sham-operated (sham) or ovariectomized (OVX) mice that received different daily doses of LP-533,401 (0, 1, 10, 100 or 250 mg/kg, orally). (D) Histomorphometric analysis of vertebrae of mice 2- and 6-weeks after sham or bilateral OVX to determine bone loss before the onset of treatment. (E) HPLC analysis of serotonin content in the brain of wild-type mice that received vehicle or LP-533,401 (250 mg/kg, orally).
Figure 17:
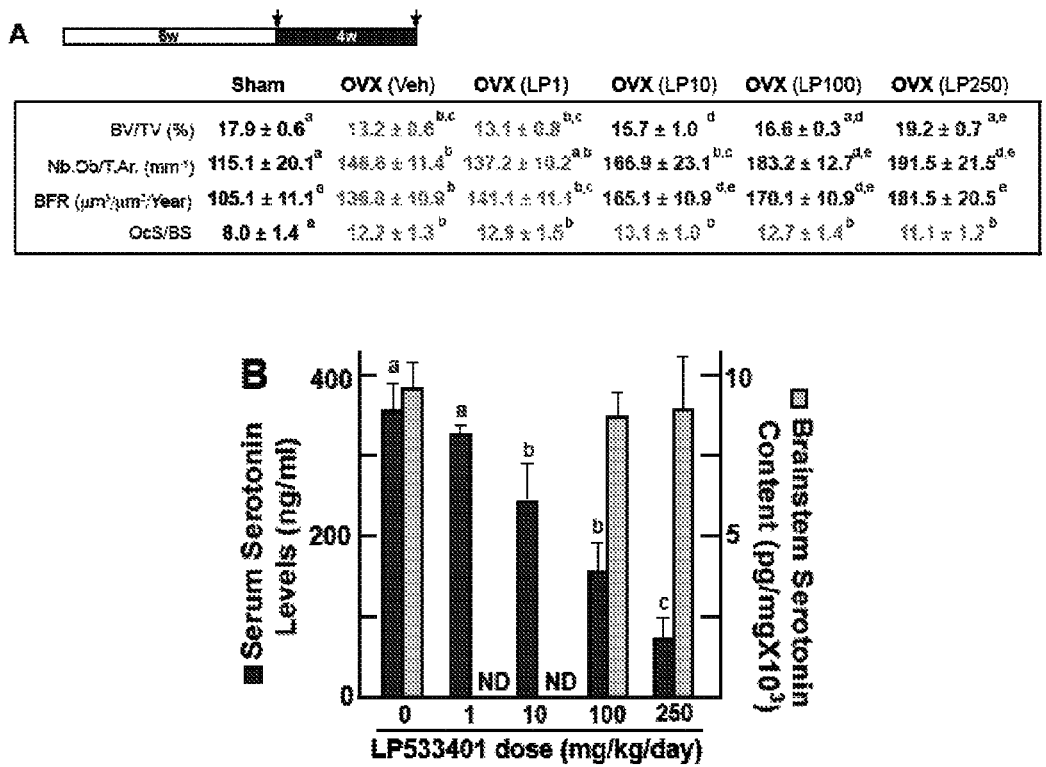
FIG. 17. (A-B) Histological analysis of vertebrae (A) and serum serotonin levels (B) of sham-operated (sham) and ovariectomized (OVX) mice treated orally with vehicle (Veh) or the indicated dose (1, 10, 100 or 250 mg/kg/day) of LP-533,401 (LP) for 4 weeks post-ovariectomy. BV/TV, Bone volume over trabecular volume; Nb.Ob/T.Ar, osteoblast number over trabecular area; BFR, bone formation rate; OcS/BS, osteoclast surface over bone surface.

Six week-old sham-operated or ovariectomized female C57B16/J mice were fed once daily with either vehicle or LP-533,401 at doses ranging from 1 to 250 mg/kg from day 1 to 28 post-ovariectomy (FIG. 16). Osteoclast surface area and serum deoxypyridinoline (Dpd) levels, a marker of bone resorption, were higher in ovariectomized mice than in sham-operated mice, regardless of their treatment, and, as a result, vehicle-treated ovariectomized mice developed a low bone mass phenotype (osteopenia) (FIG. 16A-D). In contrast, mice treated with 250, 100 or even 10 mg/kg of LP-533,401 had a bone mass that was higher than that of vehicle-treated ovariectomized (FIG. 17A-B). Consistent with the influence of serum serotonin on osteoblast proliferation and bone formation, this increase in bone mass in LP-533,401-treated ovariectomized mice was secondary to a major increase in bone formation parameters such as osteoblast numbers, bone formation rate and osteocalcin serum levels (FIG. 16C and FIG. 17A). There was also an increase in Cyclin D1 expression in the bones from LP-533,401-treated animals. While serum serotonin levels were decreased, brain serotonin content remained unaffected in LP-533,401-treated ovariectomized mice (FIG. 17B). These results establish that TPH1 inhibitors could prevent, even when used at low dose (10 mg/kg), the development of ovariectomy-induced osteoporosis.

Figure 18:
FIG. 18. Histological analysis of vertebrae or femurs of sham and OVX mice treated for 4 weeks with vehicle or the indicated dose (25, 100 or 250 mg/kg/day) of LP-533,401 (LP) from week 2 to 6 post-ovariectomy. BV/TV, Bone volume over trabecular volume; Nb.Ob/T.Ar, osteoblast number over trabecular area; BFR, bone formation rate; OcS/BS, osteoclast surface over bone surface.

TPH1 inhibitors can also revert an existing ovariectomy-induced osteopenia. Sham-operated or ovariectomized 6 week-old mice were left without treatment for 2 weeks, then were treated with vehicle or a daily dose of LP-533,401 (250 mg/kg/day) for 4 weeks. Vehicle-treated ovariectomized mice developed the expected osteopenia secondary to an increase in bone resorption parameters (FIG. 16D and FIG. 18); these parameters were also increased in LP-533,401-treated ovariectomized mice. However, in these latter animals the increase in bone formation parameters was of such amplitude that it normalized their bone mass (FIG. 18). Serum serotonin levels were decreased 80% but brain serotonin content was unaffected in LP-533,401 treated animals (FIG. 16 E and FIG. 18).

Figure 20:
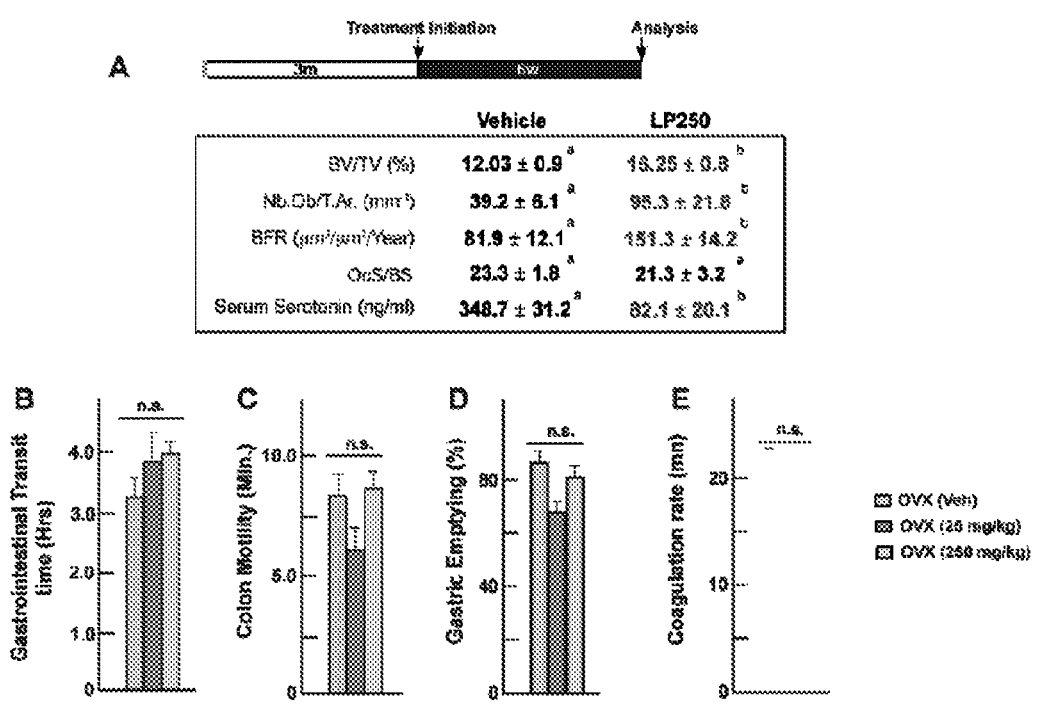
FIG. 20. (A) Histomorphometric analysis of vertebrae of 12 week-old mice that received vehicle or LP-533,401 (250 mg/kg/day, orally) for 6 weeks. (B-E) Gastrointestinal transit rate (B), colon motility (C), efficiency of gastric emptying (D) and blood coagulation rate (E) in 18 week-old ovariectomized (OVX) mice that received orally vehicle or indicated doses of LP-533,401 for 6 weeks.

TPH1 inhibitors can also rescue osteopenia if administered significantly later after ovariectomy and at lower doses. Six week-old mice, ovariectomized, were left untreated for a 6 week-period before being treated with vehicle or LP-533,401 at either 25, 100 or 250 mg/kg/day for another 6 weeks. LP-533,401, by increasing bone formation parameters, reverted the deleterious effects of ovariectomy on bone mass and increased it to levels similar (25 mg/kg) or significantly higher (100 or 250 mg/kg) than that seen in sham-operated mice (FIG. 19). This increase in bone mass affected vertebra and long bones and was also observed in naive mice (FIG. 20A). To rule out that LP-533,401, at the doses used in this study, has adverse effects on the gastroinstestinal tract or hemostasis, three cardinal parameters of gastrointestinal homeostasis were measured: total gastrointestinal transit, colonic mobility and gastric emptying. None of these parameters were affected in LP-533,401-treated mice, even when using 250 mg/kg/day (FIG. 20B-D). Likewise, coagulation rates were similar in vehicle- and LP-533,401-treated mice (FIG. 20E). Taken together, these results establish that LP-533,401, because of its bone anabolic ability, can rescue ovariectomy-induced osteoporosis in mice even when given at a low dose (25 mg/kg/day) and late after ovariectomy without deleterious consequences on hemostasis or intestinal motility.

Figure 21:
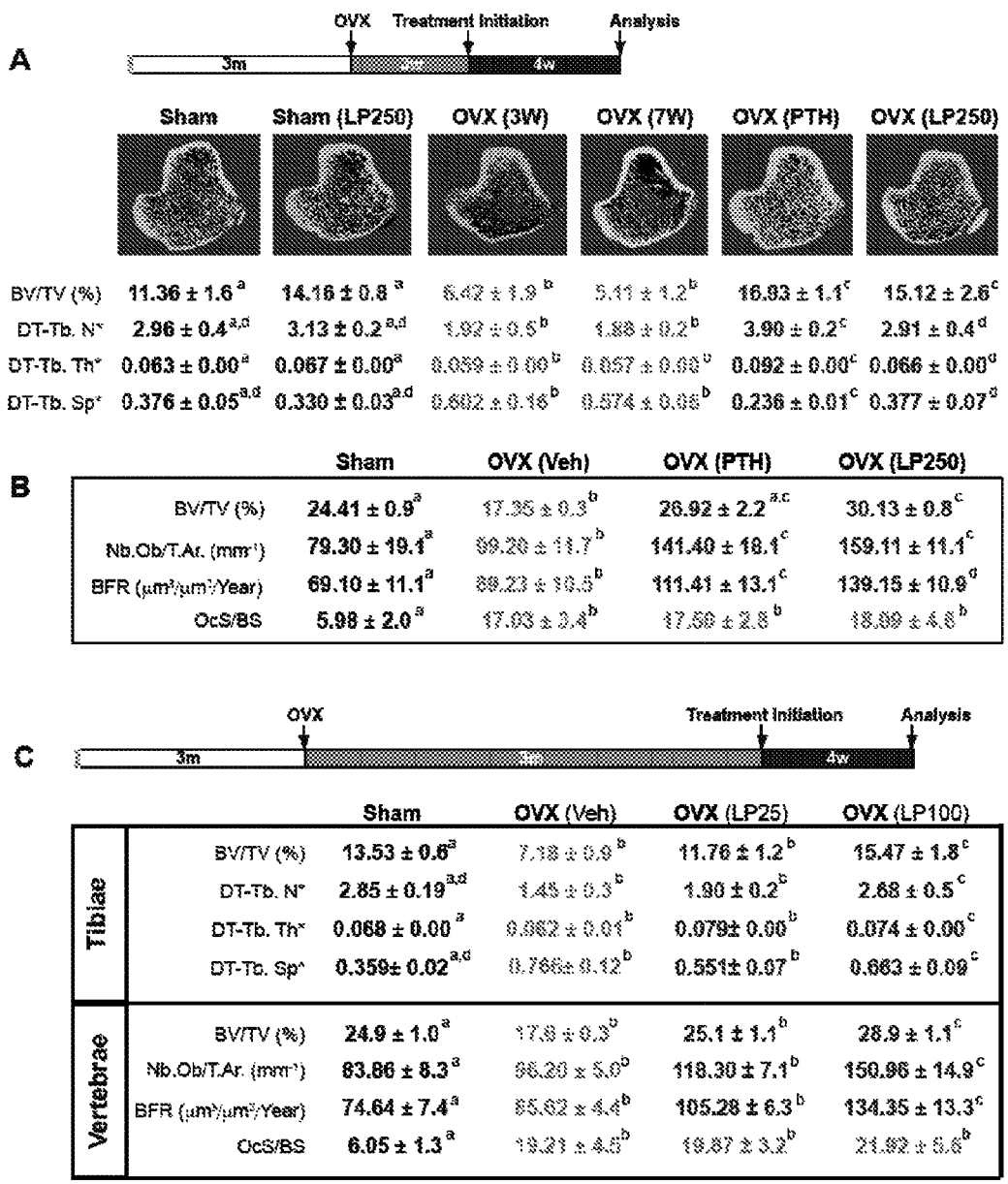
FIG. 21. (A-C) MicroComputed tomography analysis of the proximal tibia and histomorphometric analysis of vertebrae collected from rat sham-operated (sham) vehicle treated control, ovariectomized (OVX) for 3 (A) or 7 (A, B) or 12 weeks (C), and treated with vehicle or intermittent injections of PTH from week 3 to 7 post-ovariectomy (A, B) or the indicated dose (25, 100 or 250 mg/kg/day) of LP-533,401 (LP) for 4 weeks after OVX. BV/TV, Bone volume over trabecular volume; Tb.N*, trabecular number; Tb.Th*, trabecular thickness; Tb.Sp*, trabecular spacing; Nb.Ob/T.Ar, osteoblast number over trabecular area; BFR, bone formation rate; OcS/BS, osteoclast surface over bone surface.

Ovariectomized rats have been used as a model for postmenopausal osteoporosis and intermittent injections of parathyroid hormone (PTH) has been used as a standard to which novel bone anabolic agents are compared (Bilezikian et al., 2009, J. Bone Miner. Res. 24:373-385). Hence, rats were ovariectomized at 12 weeks of age and left untreated for 3 or 12 more weeks so that they developed a severe osteopenia (FIG. 21). Sham-operated or ovariectomized-rats were then treated for 4 weeks with either vehicle, a relatively high dose of PTH (80 µg/kg/day, s.c.) or increasing doses of LP-533,401 (25, 100 or 250 mg/kg/day).

Figure 22:
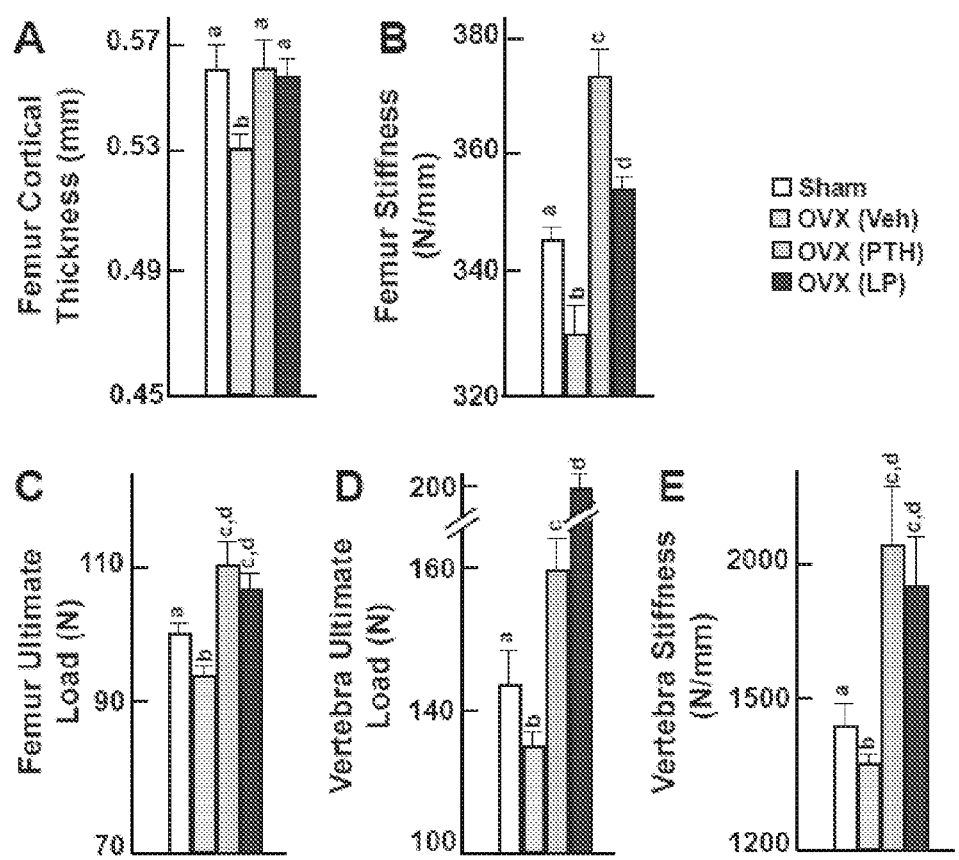
FIG. 22. (A-E) Cortical thickness, stiffness and ultimate load analysis in femur and vertebrae of rats sham-operated (sham) vehicle treated control, ovariectomized (OVX) for 3 or 7 weeks and treated with vehicle or intermittent injections of PTH from week 3 to 7 post-ovariectomy (A, B) or 250 mg/kg/day of LP-533,401 (LP) for 4 weeks after ovariectomy.

A histomorphometric analysis of vertebra showed that LP-533,401 fully rescued the ovariectomy-induced bone loss in rats whether it was given 3 or 12 weeks post-ovariectomy and even at the lowest dose used (25 mg/kg/day) (FIG. 21). This rescue was due to a significant increase in osteoblast number and bone formation rate while the number of osteoclasts per bone surface (OcS/BS) was similar in untreated, PTH- and LP-533,401-treated ovariectomized rats (FIG. 21B-C). To determine whether LP-533,401 also affects bone mass in long bones that are load bearing, micro-computed tomography (µCT) was used. Ovariectomy profoundly reduced bone volume, trabecular number (Tb.N*), trabecular thickness (Tb.Th*) and increased trabecular spacing (Tb.Sp*) in long bones (FIG. 21A). LP-533,401, at all doses tested, significantly increased Tb.N* and Tb.Th*, and reduced Tb.Sp* in these bones, thereby increasing, in a dose-dependent manner, bone mass in ovariectomized rats when compared to vehicle-treated controls. LP-533,401 appeared to be as efficient as the PTH regimen used in this experiment (FIG. 21A). Ovariectomy also leads to a significant decrease in cortical thickness at the femur mid-shaft, a key parameter of bone integrity (Parfitt et al., 1987, J. Bone Miner. Res. 2:595-610). This decrease was equally rescued by PTH and LP-533,401 (250 mg/kg/day) (FIG. 22A). To measure bone quality, femur and vertebra samples from untreated, PTH- and LP-533,401-treated ovariectomized rats were subjected to a three-point bending test and a compression analysis, to determine maximal load and stiffness, two surrogates of bone quality (FIG. 22B-E). Both parameters were significantly decreased after ovariectomy and restored to values seen in sham-operated rats by PTH and LP-533,401 (250 mg/kg/day) treatments (FIG. 22B-E). Thus, a daily oral administration of the TPH1 inhibitor LP-533,401 could revert the bone loss and architectural deterioration caused by long-term gonadal failure in rats.

Methods of Diagnosis and Treatment

The results disclosed herein show that elevated serum serotonin decreases bone mass and low serum serotonin increases it. Thus, certain embodiments of the invention are directed to methods for diagnosing and treating persons at risk of developing high or low bone mass diseases and to methods for treating or preventing diseases associated with abnormally low bone mass (such as osteoporosis and OPPG) by administering drugs that decrease the level of peripheral serum serotonin. Other embodiments are directed to new pharmaceutical compositions for treating or preventing low bone mass diseases.

One embodiment of the invention is directed to a method for determining if a patient is at risk of developing a bone disease by determining the patient's level of serum serotonin and then administering a compound disclosed herein that is a TPH1 inhibitor to the patient if the patient is at risk of developing a low bone mass disease. If the patient's level of serum serotonin is significantly higher (e.g., more than about 25% higher) than the level in a normal subject, then the patient is at risk of developing abnormally low bone mass and TPH1 inhibitors that reduce serotonin synthesis, optionally with serotonin receptor antagonists (that target HT1B, HT2A and/or HT2B), can be administered to reduce (and preferably normalize) serum serotonin levels and, optionally, block the effect of serotonin on serotonin receptors, thereby preventing low bone mass from developing or minimizing the extent of bone loss, should such loss develop. Patient monitoring will determine if an abnormal serum serotonin profile is chronic. If it is chronic, then the patient may need to continue treatment over a prolonged period (e.g., for one month, six months, one year, two years, three years, or many years) to normalize serum serotonin levels and/or maintain normal levels of serum serotonin.

When a patient's level of serum serotonin is compared to the level of serum serotonin in a normal subject, it should be understood that "normal subject" refers to a person who is matched to the patient in those characteristics that would be expected to affect serum serotonin levels, e.g., gender, age, general health, medications being taken, etc.

Methods of Treatment and Prevention of Low and High Bone Mass Diseases

The present invention provides a method of preventing or treating a low bone mass disease in a patient known or suspected to be in need of such prevention or treatment comprising administering to the patient a therapeutically effective amount of an agent that decreases serum serotonin levels. In certain embodiments, the method comprises administering to the patient therapeutically effective amounts of two or more compounds disclosed herein that decrease serum serotonin levels.

TPH1 inhibitors that may be used in certain of the methods of the present invention include the following, including any racemic mixtures and individual enantiomers, pharmaceutically acceptable salts or solvates thereof:

(121)

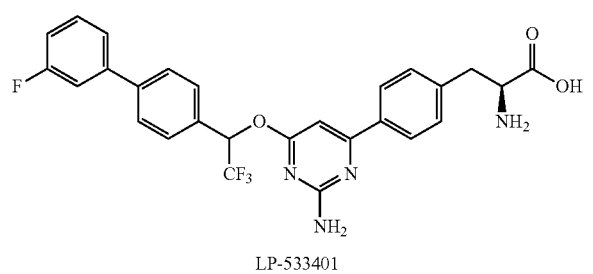

LP-533401

(122)

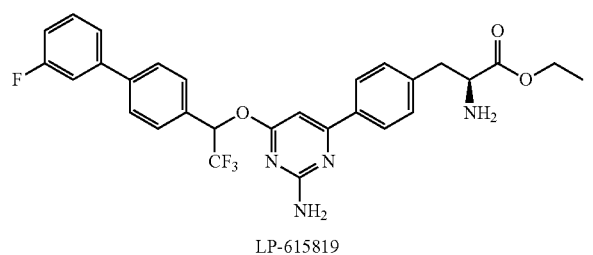

LP-615819

-continued (123)

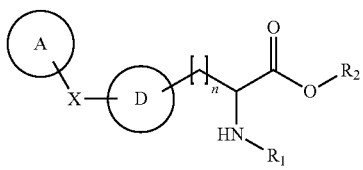

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(124)

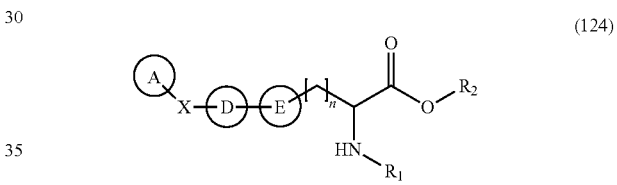

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(125)

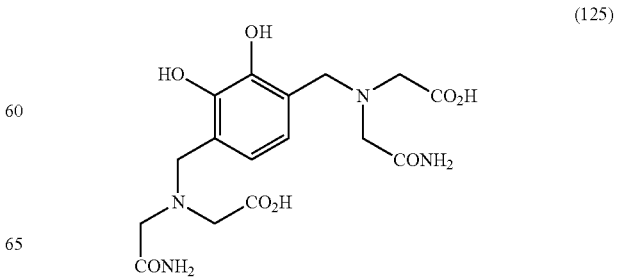

(126)

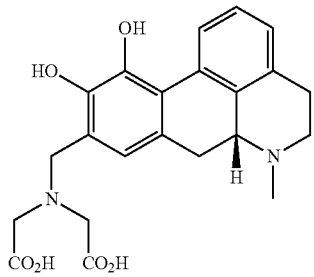

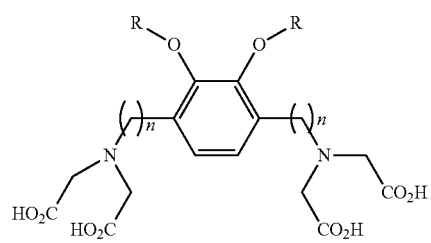

where R is hydrogen or lower alkyl; and
n is 1, 2, or 3;

(128)

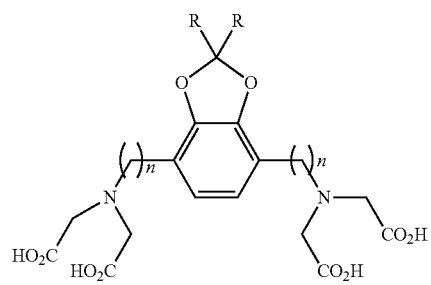

where R is hydrogen or lower alkyl; and
n is 1, 2, or 3;

(129)

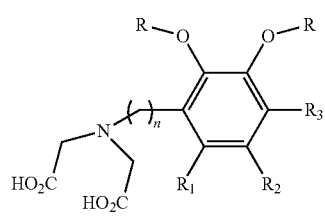

where R is hydrogen or lower alkyl;
R$_1$, R$_2$, and R$_3$, are independently:
  hydrogen;
  halogen;
  lower alkyl;
  alkoxy; or
  amino; and
n is 1, 2, or 3;

(130)

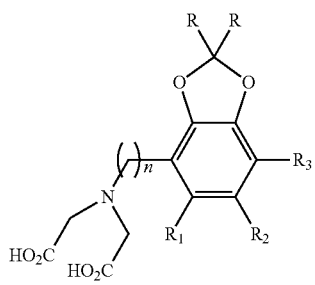

where R is hydrogen or lower alkyl;
R$_1$, R$_2$, and R$_3$, are independently:
  hydrogen;
  halogen;
  lower alkyl;
  alkoxy; or
  amino; and
n is 1, 2, or 3;

(131)

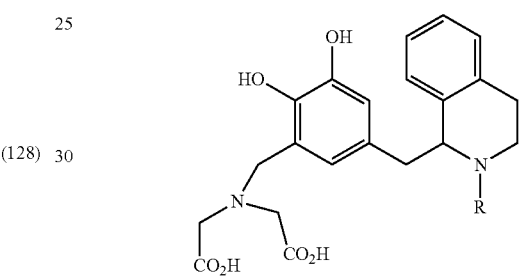

where R is hydrogen, lower alkyl, or cycloalkyl;

(132)

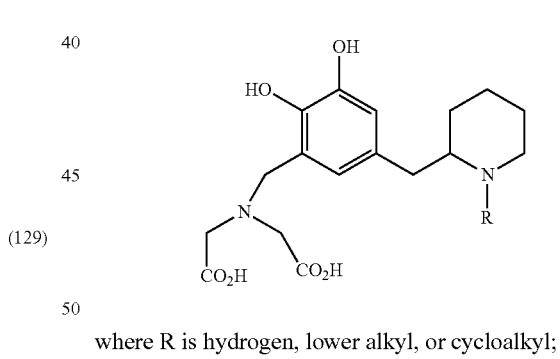

where R is hydrogen, lower alkyl, or cycloalkyl;

(133)

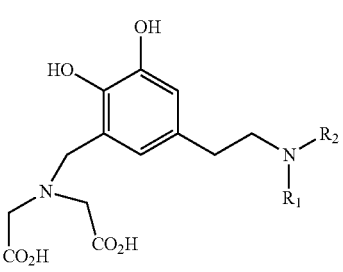

where R$_1$ and R$_2$ are independently hydrogen, lower alkyl, or cycloalkyl;

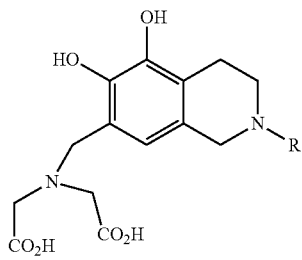

(134)

where R is hydrogen, lower alkyl, or cycloalkyl;

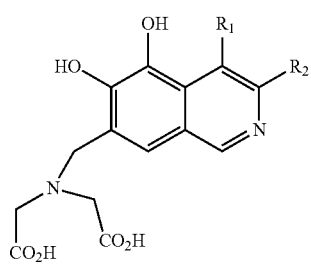

(135)

where $R_1$ and $R_2$ are independently hydrogen, lower alkyl, cycloalkyl, F, Cl, or OH;

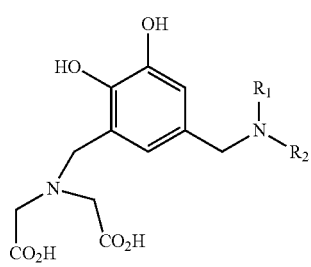

(136)

where $R_1$ and $R_2$ are independently hydrogen, lower alkyl, or cycloalkyl.

In preferred embodiments, the TPH1 inhibitors disclosed above as compounds (121)-(136) are administered to a patient in a dosage range of from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

In preferred embodiments, the TPH1 inhibitors disclosed above as compounds (121)-(136) are administered to a patient in a dosage range of from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

The dosage of TPH1 inhibitors disclosed as compounds (121)-(136) may depend on whether the TPH1 inhibitor is being administered for the prevention or for the treatment of a low bone mass disease. For prevention, preferred dose ranges include from about 5 mg/kg/day to about 250 mg/kg/day; from about 5 mg/kg/day to about 100 mg/kg/day; or from about 5 mg/kg/day to about 30 mg/kg/day; with about 10 mg/kg/day being especially preferred.

For treatment, preferred dose ranges for the TPH1 inhibitors disclosed as compounds (121)-(136) include from about 10 mg/kg/day to about 250 mg/kg/day; from about 10 mg/kg/day to about 50 mg/kg/day; or from about 10 mg/kg/day to about 30 mg/kg/day; with about 25 mg/kg/day being especially preferred.

Other TPH1 inhibitors that may be used in the methods of the present invention include the following, including any racemic mixtures and individual enantiomers, pharmaceutically acceptable salts or solvates thereof:

(137) (S)-2-Amino-3-(4-(4-amino-6-((R)-1-(naphthalen-2-yl)ethylamino)-1,3,5-triazin-2-yl)phenyl)propanoic acid;
(138) (S)-2-Amino-3-(4-(4-amino-6-((4'-methylbiphenyl-4-yl)methylamino-1,3,5-triazin-2-yl)phenyl)propanoic acid;
(139) (S)-2-Amino-3-(4-(4-morpholino-6-(naphthalen-2-yl-methylamino)-1,3,5-triazin-2-yl)phenyl)propanoic acid;
(140) (2S)-2-Amino-3-(4-(2-amino-6-(2,2,2-trifluoro-1-(2-(trifluoromethyl)phenyl)ethoxy)pyrimidin-4-yl)phenyl)propanoic acid;
(141) (2S)-2-Amino-3-(4-(2-amino-6-(2,2,2-trifluoro-1-p-tolylethoxy)pyrimidin-4-yl)phenyl)propanoic acid;
(142) (2S)-2-Amino-3-(4-(2-amino-6-(1-cyclohexyl-2,2,2-trifluoroethoxy)pyrimidin-4-yl(phenyl)propanoic acid;
(143) (S)-2-Amino-3-(4-(6-(2-fluorophenoxy)pyrimidin-4-yl)phenyl)propanoic acid;
(144) (2S)-2-Amino-3-(4-(4-(3-(4-chlorophenyl)piperidin-1-yl)-1,3,5-triazin-2-yl)phenyl)propanoic acid;
(145) (2S)-2-Amino-3-(4-(4-amino-6-(2,2,2-trifluoro-1-phenylethoxy)-1,3,5-triazin-2-yl)phenyl)propanoic acid;
(146) (S)-2-Amino-3-(5-(4-amino-6-((R)-(naphthalen-2-yl)ethylamino)-1,3,5-triazin-2-yl)pyridin-2-yl)propanoic acid;
(147) (S)-2-Amino-3-(3-(4-amino-6-(R)-1-(naphthalen-2-yl)ethylamino)-1,3,5-triazin-2-yl)-1H-pyrazol-1-yl)propanoic acid;
(148) (S)-2-Amino-3-(4'-(3-(cyclopentyloxy)-4-methoxybenzylamino)biphenyl-4-yl)propanoic acid;

(149) (S)-2-Amino-3-(4-(6-(3-(cyclopentyloxy)-4-methoxybenzylamino)pyrimidin-4-yl)phenyl)propanoic acid;
(150) (S)-2-Amino-3-(4-(6-(3-(cyclopentyloxy)-4-methoxybenzylamino)pyrazin-2-yl)phenyl)propanoic acid;
(151) (S)-2-Amino-3-(4-(5-((4'-methylbiphenyl-2-yl)methylamino)pyrazin-2-yl)phenyl)propanoic acid;
(152) (2S)-2-Amino-3-(4-(6-(2,2,2-trifluoro-1-phenylethoxy)-pyrimidin-4-yl)phenyl)propanoic acid;
(153) (2S)-2-Amino-3-(4-(6-(1-(3,4-difluorophenyl)-2,2,2-trifluoroethoxy)pyriinidin-4-yl)phenyl)propanoic acid;
(154) (S)-2-Amino-3-(4-(5-(3-(cyclopentyloxy)-4-methoxybenzylamino)-pyrazin-2-yl)phenyl)propanoic acid;
(155) (S)-2-Amino-3-(4-(5-((3-(cyclopentyloxy)-4-methoxybenzyl)-(methyl)amino)pyrazin-2-yl)phenyl)propanoic acid;
(156) (S)-2-Amino-3-(4-(5-((1,3-dimethyl-1H-pyrazol-4-yl)methylamino)pyrazin-2-yl)phenyl)propanoic acid;
(157) (S)-2-Amino-3-(4-(4-amino-6-((S)-1-(naphthalen-2-yl)ethylamino)-1,3,5-triazin-2-yloxy)phenyl)propanoic acid;
(158) (S)-2-Amino-3-(4-(4-amino-6-((R)-1-(biphenyl-2-yl)-2,2,2-trifluoroethoxy)-1,3,5-triazin-2-yl)phenyl)propanoic acid;
(159) (2S)-2-Amino-3-(4-(4-amino-6-(1-(6,8-difluoronaphthalene-2-yl)ethylamino)-1,3,5-triazin-2-yl)phenyl)propanoic acid;
(160) (2S)-2-Amino-3-(4-(4-amino-6-(2,2,2-trifluoro-1-(3'-methylbiphenyl-2-yl)ethoxy)-1,3,5-triazin-2-yl)phenv)propanoic acid;
(161) (S)-2-Amino-3-(4-(5-(3,4-dimethoxyphenylcarbamoyl)-pyrazin-2-yl)phenyl)propanoic acid;
(162) (5)-2-Amino-3-(4-(2-amino-6-(4-(2-(trifluoromethyl)phenyl)-piperidin-1-yl)pyrimidin-4-yl)phenyl)propanoic acid;
(163) (S)-2-Amino-3-(4-(2-amino-6-((R)-1-(naphthalen-2-yl)ethylamino)pyrimidin-4-yl)phenyl)propanoic acid;
(164) (S)-2-Amino-3-(4-(2-amino-6-(methyl(R)-1-(naphthalen-2-yl)ethyl)amino)pyrimidin-4-yl)phenyl)propanoic acid;
(165) (S)-2-Amino-3-(4-(2-amino-6-((S)-2,2,2-trifluoro-1-(6-methoxynaphthalen-2-yl)ethoxy)pyrimidin-4-yl)phenyl)propanoic acid;
(166) (S)-2-Amino-3-(4-(5-(biphenyl-4-ylmethylamino)pyrazin-2-yl)phenyl)propanoic acid;
(167) (S)-2-Amino-3-(4-(5-(naphthalen-2-ylmethylamino)pyrazin-2-yl)phenyl)propanoic acid;
(168) (S)-2-(Tert-butoxycarbonylamino)-3-(4-(5-(naphthalen-2-ylmethylamino)pyrazin-2-yl)phenyl)propanoic acid;
(169) (S)-2-Morpholinoethyl 2-amino-3-(4-(5-(naphthalen-2-ylmethylamino)pyrazin-2-yl)phenyl)propanoate;
(170) (S)-2-Amino-3-(4-(2-amino-6-(2,2,2-trifluoro-1-(3'-fluorobiphenyl-4-yl)ethoxy)pyrimidin-4-yl)phenyl)propanoic acid;
(171) (S)-2-Amino-3-(4-(2-amino-6-(benzylthio)pyrimidin-4-yl)phenyl)propanoic acid;
(172) (S)-2-Amino-3-(4-(2-amino-6-(naphthalen-2-ylmethylthio)pyrimidin-4-yl)phenyl)propanoic acid;
(173) (2S)-2-Amino-3-(4-(2-amino-6-(1-(3,4-difluorophenyl)-2,2,2-trifluoroethoxy)pyrimidin-4-yl)phenyl)propanoic acid;
(174) (2S)-2-Amino-3-(4-(2-amino-6-(2,2,2-trifluoro-1-(3'-methylbiphenyl-2-yl)ethoxy)pyrimidin-4-yl)phenyl)propanoic acid;
(175) (S)-2-Amino-3-(4-(5-(3-(cyclopentyloxy)-4-methoxybenzylamino)pyridin-3-yl)phenyl)propanoic acid;
(176) 2-Amino-3-(3-(4-amino-6-((R)-1-(naphthalen-2-yl)ethylamino)-1,3,5-triazin-2-yl)phenyl)propanoic acid;
(177) 2-Amino-3-(4-(4-amino-6-((R)-1-(naphthalen-2-yl)ethylamino)-1,3,5-triazin-2-yl)-2-fluorophenyl)propanoic acid;
(178) (2S)-2-Amino-3-(4-(4-amino-6-(1-(adamantyl)ethylamino)-1,3,5-triazin-2-yl)phenyl)propanoic acid;
(179) (S)-2-Amino-3-(4-(5-fluoro-4-((R)-1-(naphthalen-2-yl)ethylamino)pyrimidin-2-yl)phenyl)propanoic acid;
(180) (S)-2-Amino-3-(4-(2-amino-6-(4-(trifluoromethyl)benzylamino)pyrimidin-4-yl)phenyl)propanoic acid;
(181) 2-Amino-3-(5-(5-phenylthiophen-2-yl)-1H-indol-3-yl)propanoic acid;
(182) (S)-2-Amino-3-(4-(4-(4-phenoxyphenyl)-1H-1,2,3-triazol-1-yl)phenyl)propanoic acid;
(183) (S)-2-Amino-3-(4-(4-(4-(thiophene-2-carboxamido)phenyl)-1H-1,2,3-triazol-1-yl)phenyl)propanoic acid; and
(184) (S)-2-Amino-3-(4-(2-amino-6-(phenylethynyl)pyrimidin-4-yl)phenyl)propanoic acid;

Additional TPH1 inhibitors that may be used in the present invention include:
(185) N-[(1R,4R,9aS)-4-phenyl octahydropyrido[2,1-c][1,4]oxazin-1-yl]3,4,5-trimethoxybenzamide;
(186) 2,6-Piperidinedione, 3-[3-(dimethylamino)propyl]-3-(3-methoxyphenyl)-4,4-dimethyl-, monohydrochloride; and
(187) Triptosine (CAS registry number 86248-47-7; U.S. Pat. No. 4,472,387).

In preferred embodiments, the TPH1 inhibitors disclosed above as compounds (137)-(187) are administered to a patient in a dosage range of from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

In preferred embodiments, the TPH1 inhibitors disclosed above as compounds (137)-(187) are administered to a patient in a dosage range of from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

The dosage of TPH1 inhibitors disclosed as compounds (137)-(187) may depend on whether the TPH1 inhibitor is being administered for the prevention or for the treatment of a low bone mass disease. For prevention, preferred dose ranges include from about 5 mg/kg/day to about 250 mg/kg/day; from about 5 mg/kg/day to about 100 mg/kg/day; or from about 5 mg/kg/day to about 30 mg/kg/day; with about 10 mg/kg/day being especially preferred.

For treatment, preferred dose ranges for the TPH1 inhibitors disclosed as compounds (137)-(187) include from about 10 mg/kg/day to about 250 mg/kg/day; from about 10 mg/kg/day to about 50 mg/kg/day; or from about 10 mg/kg/day to about 30 mg/kg/day; with about 25 mg/kg/day being especially preferred.

Additional TPH1 inhibitors that may be used in the present invention are listed in the table below.

TABLE 2

(S)-2-amino-3-(4-(5-(2-fluoro-4,5-dimethoxybenzylamino)pyrazin-2-yl)phenyl)propanoic acid
(S)-2-amino-3-(4-(2-amino-6-(4-(2-methoxyphenyl)piperidin-1-yl)pyrimidin-4-yl)phenyl)propanoic acid
(S)-2-amino-3-(4-(6-(3-(cyclopentyloxy)-4-methoxybenzylamino)-2-(dimethylamino)pyrimidin-4-yl)phenyl)propanoic acid
(S)-2-amino-3-(4-(5-(3,4-dimethylbenzylamino)pyrazin-2-yl)phenyl)propanoic acid
(S)-2-amino-3-(4-(5-(biphenyl-2-ylmethylamino)pyrazin-2-yl)phenyl)propanoic acid
(S)-ethyl 2-amino-3-(4-(2-amino-6-(4-(trifluoromethyl)benzylamino)pyrimidin-4-yl)phenyl)propanoate
(S)-2-amino-3-(4-(5-(cyclopentylmethylamino)pyrazin-2-yl)phenyl)propanoic acid
(2S)-2-amino-3-(4-(2-amino-6-(3-(2-(trifluoromethyl)phenyl)pyrrolidin-1-yl)pyrimidin-4-yl)phenyl)propanoic acid
(2S)-2-amino-3-(4-(2-amino-6-(1,2,3,4-tetrahydronaphthalen-1-ylamino)pyrimidin-4-yl)phenyl)propanoic acid
(S)-2-amino-3-(4-(2-amino-6-((R)-1-(naphthalen-2-yl)ethoxy)pyrimidin-4-yl)phenyl)propanoic acid
(2S)-2-amino-3-(4-(2-amino-6-(1,2-diphenylethylamino)pyrimidin-4-yl)phenyl)propanoic acid
(S)-2-amino-3-(4-(2-amino-6-((R)-1-(4-(benzo[b]thiophen-3-yl)phenyl)ethylamino)pyrimidin-4-yl)phenyl)propanoic acid
(S)-2-amino-3-(4-(4-amino-6-((R)-1-(4'-methoxybiphenyl-4-yl)ethylamino)-1,3,5-triazin-2-yl)phenyl)propanoic acid
2-amino-3-(1-(4-amino-6-((R)-1-(naphthalen-2-yl)ethylamino)-1,3,5-triazin-2-yl)piperidin-4-yl)propanoic acid
(2S)-2-amino-3-(4-(4-amino-6-(1-(4-fluoronaphthalen-1-yl)ethylamino)-1,3,5-triazin-2-yl)phenyl)propanoic acid
(S)-2-amino-3-(4-(4-amino-6-((3'-fluorobiphenyl-4-yl)methylamino)-1,3,5-triazin-2-yl)phenyl)propanoic acid
2-amino-3-(4-(4-amino-6-((R)-1-(naphthalen-2-yl)ethylamino)-1,3,5-triazin-2-yl)-2-fluorophenyl)propanoic acid
(S)-2-amino-3-(4-(2-amino-6-((R)-2,2,2-trifluoro-1-(3'-methoxybiphenyl-4-yl)ethoxy)pyrimidin-4-yl)phenyl)propanoic acid
(2S)-2-amino-3-(4-(4-amino-6-(2,2,2-trifluoro-1-(3'-fluorobiphenyl-2-yl)ethoxy)-1,3,5-triazin-2-yl)phenyl)propanoic acid
(2S)-2-amino-3-(4-(4-amino-6-(1-(4-tert-butylphenyl)ethylamino)-1,3,5-triazin-2-yl)phenyl)propanoic acid
(2S)-2-amino-3-(4-(2-amino-6-(2,2,2-trifluoro-1-(3'-fluorobiphenyl-4-yl)ethoxy)pyrimidin-4-yl)phenyl)propanoic acid
(2S)-2-amino-3-(4-(4-amino-6-(6,7-dihydroxy-1-methyl-3,4-dihydroisoquinolin-2(1H)-yl)-1,3,5-triazin-2-yl)phenyl)propanoic acid
(2S)-2-amino-3-(4-(4-amino-6-(2,2,2-trifluoro-1-(3'-methylbiphenyl-4-yl)ethoxy)-1,3,5-triazin-2-yl)phenyl)propanoic acid TABLE 2-continued (S)-2-amino-3-(4-(4-amino-6-((R)-1-(naphthalen-2-yl)ethylamino)pyrimidin-2-yl)phenyl)propanoic acid
(S)-2-amino-3-(4-(2-amino-6-(benzylthio)pyrimidin-4-yl)phenyl)propanoic acid
(2S)-2-amino-3-(4-(2-amino-6-(2,2,2-trifluoro-1-(4'-fluorobiphenyl-4-yl)ethoxy)pyrimidin-4-yl)phenyl)propanoic acid
(2S)-2-amino-3-(4-(6-(3-(4-chlorophenoxy)piperidin-1-yl)pyrimidin-4-yl)phenyl)propanoic acid
(S)-3-(4-(4-amino-6-((R)-1-(naphthalen-2-yl)ethylamino)-1,3,5-triazin-2-yl)phenyl)-2-(2-aminoacetamido)propanoic acid
(S)-2-amino-3-(4-(6-((R)-1-(naphthalen-2-yl)ethylamino)-2-(trifluoromethyl)pyrimidin-4-yl)phenyl)propanoic acid
(S)-2-amino-3-(4-(2-amino-6-(4-(3-chlorophenyl)piperazin-1-yl)pyrimidin-4-yl)phenyl)propanoic acid
(S)-2-amino-3-(4-(2-amino-6-((R)-2,2,2-trifluoro-1-phenylethoxy)pyrimidin-4-yl)phenyl)propanoic acid
(2S)-2-amino-3-(4-(2-amino-6-(1,4-diphenylbutylamino)pyrimidin-4-yl)phenyl)propanoic acid
(2S)-2-amino-3-(4-(6-(1-(3'-chlorobiphenyl-2-yl)-2,2,2-trifluoroethoxy)pyrimidin-4-yl)phenyl)propanoic acid
(2S)-2-amino-3-(4-(4-amino-6-(1-(biphenyl-4-yl)-2,2,2-trifluoroethoxy)-1,3,5-triazin-2-yl)phenyl)propanoic acid
(2S)-2-amino-3-(4-(2-amino-6-(2,2,3,3,3-pentafluoro-1-(3-fluoro-4-methylphenyl)propoxy)pyrimidin-4-yl)phenyl)propanoic acid
(S)-ethyl 2-amino-3-(4-(2-amino-6-((R)-2,2,2-trifluoro-1-(3'-methoxybiphenyl-4-yl)ethoxy)pyrimidin-4-yl)phenyl)propanoate
(S)-2-amino-3-(4-(2-amino-6-((S)-2,2,2-trifluoro-1-(3'-methoxybiphenyl-4-yl)ethoxy)pyrimidin-4-yl)phenyl)propanoic acid
(2S)-2-amino-3-(4-(2-amino-6-(2,2,2-trifluoro-1-(3-fluoro-3'-methoxybiphenyl-4-yl)ethoxy)pyrimidin-4-yl)phenyl)propanoic acid
(2S)-2-amino-3-(4-(2-amino-6-(1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(3'-methoxy-5-methylbiphenyl-2-yl)ethoxy)pyrimidin-4-yl)phenyl)propanoic acid
(2S)-2-amino-3-(4-(2-amino-6-(2,2,2-trifluoro-1-(4'-methoxy-5-methylbiphenyl-2-yl)ethoxy)pyrimidin-4-yl)phenyl)propanoic acid
(2S)-2-amino-3-(4-(2-amino-6-(2,2,2-trifluoro-1-(3'-methoxy-3-(methylsulfonyl)biphenyl-4-yl)ethoxy)pyrimidin-4-yl)phenyl)propanoic acid
(2S)-2-amino-3-(4-(2-amino-6-(1-(2-(cyclopropylmethoxy)-4-fluorophenyl)-2,2,2-trifluoroethoxy)pyrimidin-4-yl)phenyl)propanoic acid
(2S)-2-amino-3-(4-(6-(1-(2-(cyclopropylmethoxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(2-(isopentyloxy)phenyl)ethoxy)pyrimidin-4-yl)phenyl)propanoic acid
(2S)-2-amino-3-(4-(5-(2,2,2-trifluoro-1-(3'-fluorobiphenyl-4-yl)ethoxy)pyrazin-2-yl)phenyl)propanoic acid
(2S)-2-amino-3-(4-(2-amino-6-(2,2,2-trifluoro-1-(4'-methoxybiphenyl-2-yl)ethoxy)pyrimidin-4-yl)phenyl)propanoic acid
(2S)-2-amino-3-(4-(2-amino-6-(1-(3'-carbamoylbiphenyl-2-yl)-2,2,2-trifluoroethoxy)pyrimidin-4-yl)phenyl)propanoic acid
(2S)-2-amino-3-(4-(2-amino-6-(1-(4'-carbamoylbiphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(4-(2-methoxyphenyl)phenyl)ethoxy)pyrimidin-4-yl)phenyl)propanoic acid
(2S)-2-amino-3-(4-(6-(2,2,2-trifluoro-1-(4-(2-methoxyphenoxy)phenyl)ethoxy)pyrimidin-4-yl)phenyl)propanoic acid
(2S)-2-amino-3-(4-(6-(2,2,2-trifluoro-1-(2-(isopentyloxy)phenyl)ethoxy)pyrimidin-4-yl)phenyl)propanoic acid
(2S)-3-(4-(6-(1-(3'-acetamidobiphenyl-2-yl)-2,2,2-trifluoroethoxy)-2-aminopyrimidin-4-yl)phenyl)-2-aminopropanoic acid
(2S)-3-(4-(6-(1-(4'-acetamidobiphenyl-2-yl)-2,2,2-trifluoroethoxy)-2-aminopyrimidin-4-yl)phenyl)-2-aminopropanoic acid TABLE 2-continued (2S)-2-amino-3-(4-(2-amino-6-(1-(4-cyanophenyl)-2,2,2-trifluoroethoxy)pyrimidin-4-yl)phenyl)propanoic acid
(S)-ethyl 2-amino-3-(4-(2-amino-6-((R)-2,2,2-trifluoro-1-p-tolylethoxy)pyrimidin-4-yl)phenyl)propanoate
(2S)-2-amino-3-(4-(2-amino-6-(2,2,2-trifluoro-1-(1-methoxybicyclo[2.2.2]oct-5-en-2-yl)ethoxy)pyrimidin-4-yl)phenyl)propanoic acid
(2S)-2-amino-3-(4-(2-amino-6-(1-(4-(cyclopentyloxy)phenyl)-2,2,2-trifluoroethoxy)pyrimidin-4-yl)phenyl)propanoic acid
(2S)-2-amino-3-(4-(6-(1-(4-(cyclopentyloxy)phenyl)-2,2,2-trifluoroethoxy)pyrimidin-4-yl)phenyl)propanoic acid
(2S)-2-amino-3-(4-(2-amino-6-(2,2,2-trifluoro-1-(4-(3-methoxyphenoxy)phenyl)ethoxy)pyrimidin-4-yl)phenyl)propanoic acid
(2S)-2-amino-3-(4-(2-amino-6-(1-(4,5-dimethoxybiphenyl-2-yl)-2,2,2-trifluoroethoxy)pyrimidin-4-yl)phenyl)propanoic acid
(2S)-2-amino-3-(4-(2-amino-6-(1-(4,5-dimethoxy-3'-methylbiphenyl-2-yl)-2,2,2-trifluoroethoxy)pyrimidin-4-yl)phenyl)propanoic acid
(2S)-2-amino-3-(4-(5-(2,2,2-trifluoro-1-(2'-methylbiphenyl-2-yl)ethoxy)pyrazin-2-yl)phenyl)propanoic acid
(2S)-2-amino-3-(4-(6-(2,2,2-trifluoro-1-(3-methoxyphenoxy)phenyl)ethoxy)pyrimidin-4-yl)phenyl)propanoic acid
(2S)-2-amino-3-(4-(2-amino-6-(1-(2-(3,5-difluorophenoxy)phenyl)-2,2,2-trifluoroethoxy)pyrimidin-4-yl)phenyl)propanoic acid
(2S)-2-amino-3-(4-(2-amino-6-(2,2,2-trifluoro-1-(4-(4-methoxyphenoxy)phenyl)ethoxy)pyrimidin-4-yl)phenyl)propanoic acid
(2S)-2-amino-3-(4-(2-amino-6-(1-(4'-((S)-2-amino-2-carboxyethyl)biphenyl-2-yl)-2,2,2-trifluoroethoxy)pyrimidin-4-yl)-phenyl)propanoic acid
(2S)-2-amino-3-(4-(2-amino-6-(1-(2-bromophenyl)-2,2,2-trifluoroethoxy)pyrimidin-4-yl)phenyl)propanoic acid
(2S)-2-amino-3-(4-(5-(2,2,2-trifluoro-1-(3'-methylbiphenyl-2-yl)ethoxy)pyrazin-2-yl)phenyl)propanoic acid
(2S)-2-amino-3-(4-(2-amino-6-(2,2,2-trifluoro-1-(4-methoxybiphenyl-2-yl)ethoxy)pyrimidin-4-yl)phenyl)propanoic acid
(2S)-2-amino-3-(4-(5-(2,2,2-trifluoro-1-(2-(4-methylthiophen-3-yl)ethoxy)pyrazin-2-yl)phenyl)propanoic acid
(2S)-2-amino-3-(4-(2-amino-6-(2,2,2-trifluoro-1-(4-methoxy-3'-methylbiphenyl-2-yl)ethoxy)pyrimidin-4-yl)phenyl)propanoic acid
(2S)-2-amino-3-(4-(2-amino-6-(2,2,2-trifluoro-1-(3'-(hydroxymethyl)biphenyl-2-yl)ethoxy)pyrimidin-4-yl)phenyl)propanoic acid
(2S)-2-amino-3-(4-(2-amino-6-(1-(3'-cyanobiphenyl-2-yl)-2,2,2-trifluoroethoxy)pyrimidin-4-yl)phenyl)propanoic acid
(2S)-2-amino-3-(4-(6-(1-(2-(3,5-difluorophenoxy)phenyl)-2,2,2-trifluoroethoxy)pyrimidin-4-yl)phenyl)propanoic acid
(2S)-2-amino-3-(4-(6-(2,2,2-trifluoro-1-(4-(4-methoxyphenoxy)phenyl)ethoxy)pyrimidin-4-yl)phenyl)propanoic acid
(2S)-2-amino-3-(4-(2-amino-6-(2,2,2-trifluoro-1-(2-(4-methylthiazol-2-yl)thiophen-3-yl)ethoxy)pyrimidin-4-yl)phenyl)propanoic acid
(2S)-2-amino-3-(4-(2-amino-6-(2,2,2-trifluoro-1-(5-(4-methoxyphenyl)isoxazol-3-yl)ethoxy)pyrimidin-4-yl)phenyl)propanoic acid
(2S)-2-amino-3-(4-(2-amino-6-(2,2,2-trifluoro-1-(1-phenyl-5-(trifluoromethyl)-1H-pyrazol-4-yl)ethoxy)pyrimidin-4-yl)phenyl)propanoic acid
(2S)-2-amino-3-(4-(2-amino-6-(1-(2-(cyclohexyloxy)-4-methylphenyl)-2,2,2-trifluoroethoxy)pyrimidin-4-yl)phenyl)propanoic acid
(2S)-2-amino-3-(4-(2-amino-6-(1-(2-(cyclopentyloxy)-4-methylphenyl)-2,2,2-trifluoroethoxy)pyrimidin-4-yl)phenyl)propanoic acid
(2S)-2-amino-3-(4-(2-amino-6-(1-(benzo[d]thiazol-6-yl)-2,2,2-trifluoroethoxy)pyrimidin-4-yl)phenyl)propanoic acid
(2S)-2-amino-3-(4-(2-amino-6-(2,2,2-trifluoro-1-(1-methyl-1H-imidazol-5-yl)ethoxy)pyrimidin-4-yl)phenyl)propanoic acid
(2S)-2-amino-3-(4-(6-(1-(2-(cyclopentyloxy)-4-methylphenyl)-2,2,2-trifluoroethoxy)pyrimidin-4-yl)phenyl)propanoic acid
(2S)-2-amino-3-(4-(6-(1-(2-(cyclohexyloxy)-4-methylphenyl)-2,2,2-trifluoroethoxy)pyrimidin-4-yl)phenyl)propanoic acid
(2S)-2-amino-3-(4-(2-amino-6-(2,2,2-trifluoro-1-(pyridin-3-yl)ethoxy)pyrimidin-4-yl)phenyl)propanoic acid
(2S)-2-amino-3-(4-(2-amino-6-(1-(1,3-dimethyl-1H-pyrazol-5-yl)-2,2,2-trifluoroethoxy)pyrimidin-4-yl)phenyl)propanoic acid
(S)-2-amino-3-(4-(2-amino-6-(3-hydroxyphenyl)pyrimidin-4-yl)phenyl)propanoic acid
(2S)-2-amino-3-(4-(2-amino-6-(2,2,2-trifluoro-1-(3'-hydroxybiphenyl-2-yl)ethoxy)pyrimidin-4-yl)phenyl)propanoic acid
(S)-2-amino-3-(4-(2-amino-6-(3,5-difluorophenyl)pyrimidin-4-yl)phenyl)propanoic acid
(2S)-2-amino-3-(4-(2-amino-6-(1-(3',5'-difluorobiphenyl-2-yl)-2,2,2-trifluoroethoxy)pyrimidin-4-yl)phenyl)propanoic acid
(2S)-2-amino-3-(4-(6-(2,2,2-trifluoro-1-(3'-fluorobiphenyl-3-yl)ethoxy)pyrazin-2-yl)phenyl)propanoic acid
(2S)-2-amino-3-(4-(2-amino-6-(1-(5-ethoxy-2-methyl-2,3-dihydrobenzofuran-6-yl)-2,2,2-trifluoroethoxy)pyrimidin-4-yl)phenyl)propanoic acid
(2S)-2-amino-3-(4-(2-amino-6-(1-(benzofuran-5-yl)-2,2,2-trifluoroethoxy)pyrimidin-4-yl)phenyl)propanoic acid
(2S)-2-amino-3-(4-(2-amino-6-(2,2,2-trifluoro-1-(2-m-tolylfuran-3-yl)ethoxy)pyrimidin-4-yl)phenyl)propanoic acid
(S)-ethyl 3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoate
(2S)-2-amino-3-(4-(6-(2,2,2-trifluoro-1-(2-(4-methylthiophen-3-yl)ethoxy)pyrazin-2-yl)phenyl)propanoic acid
(2S)-2-amino-3-(4-(2-amino-6-(2,2,2-trifluoro-1-(5-methyl-3-phenylisoxazol-4-yl)ethoxy)pyrimidin-4-yl)phenyl)propanoic acid
(S)-2-amino-3-(4-(2-amino-6-(3-(methylthio)phenyl)pyrimidin-4-yl)phenyl)propanoic acid
(2S)-2-amino-3-(4-(2-amino-6-(2,2,2-trifluoro-1-(3'-(methylthio)biphenyl-2-yl)ethoxy)pyrimidin-4-yl)phenyl)propanoic acid
(2S)-2-amino-3-(4-(2-amino-6-(1-(3'-((dimethylamino)methyl)biphenyl-2-yl)-2,2,2-trifluoroethoxy)pyrimidin-4-yl)phenyl)propanoic acid
(S)-2-amino-3-(4-(2-amino-6-(3-(trifluoromethoxy)phenyl)pyrimidin-4-yl)phenyl)propanoic acid
(2S)-2-amino-3-(4-(2-amino-6-(2,2,2-trifluoro-1-(3'-(trifluoromethoxy)biphenyl-2-yl)ethoxy)pyrimidin-4-yl)phenyl)propanoic acid
(S)-3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoic acid
(2S)-2-amino-3-(4-(2-amino-6-(2,2,2-trifluoro-1-(1-methyl-5-phenyl-1H-pyrazol-4-yl)ethoxy)pyrimidin-4-yl)phenyl)propanoic acid
(2S)-2-amino-3-(4-(2-amino-6-(2,2,2-trifluoro-1-(4-(methylsulfonyl)phenyl)ethoxy)pyrimidin-4-yl)phenyl)propanoic acid
(S)-2-amino-3-(4-(2-amino-6-((R)-1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(1-(2-chloro-4-(methylsulfonyl)phenyl)-2,2,2-trifluoroethoxy)pyrimidin-4-yl)phenyl)propanoic acid
(2S)-2-amino-3-(4-(2-amino-6-(2,2,2-trifluoro-1-(3-(furan-2-yl)thiophen-2-yl)ethoxy)pyrimidin-4-yl)phenyl)propanoic acid
(2S)-2-amino-3-(4-(2-amino-6-(1-(2-(cyclopentyloxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(2-(3-methoxyphenyl)cyclohex-1-enyl)ethoxy)pyrimidin-4-yl)phenyl)propanoic acid
(2S)-2-amino-3-(4-(2-amino-6-(2,2,2-trifluoro-1-(pyrimidin-5-yl)ethoxy)pyrimidin-4-yl)phenyl)propanoic acid
(2S)-2-amino-3-(4-(5-(2,2,2-trifluoro-1-(3'-methoxybiphenyl-3-yl)ethoxy)pyrazin-2-yl)phenyl)propanoic acid
(S)-2-amino-3-(4-(2-amino-6-((S)-1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(2-(furan-2-carboxamido)phenyl)ethoxy)pyrimidin-4-yl)phenyl)propanoic acid
(2S)-2-amino-3-(4-(2-amino-6-(1-(4-chloro-2-(methylsulfonyl)phenyl)-2,2,2-trifluoroethoxy)pyrimidin-4-yl)phenyl)propanoic acid
(S)-isopropyl 2-amino-3-(4-(2-amino-6-((R)-2,2,2-trifluoro-1-(3'-methoxybiphenyl-4-yl)ethoxy)pyrimidin-4-yl)phenyl)propanoate TABLE 2-continued (2S)-2-amino-3-(4-(6-(1-(2-(cyclopentyloxy)-4-fluorophenyl)-2,2,2-trifluoroethoxy)pyrimidin-4-yl)phenyl)propanoic acid
(2S)-2-amino-3-(4-(6-(1-(2-(cyclohexyloxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(1-(thiophen-2-yl)cyclohexyl)ethoxy)pyrimidin-4-yl)phenyl)propanoic acid
(2S)-2-amino-3-(4-(2-(2,2,2-trifluoro-1-(3'-methoxybiphenyl-4-yl)ethoxy)thiazol-5-yl)phenyl)propanoic acid
(2S)-2-amino-3-(4-(2-amino-6-(1-(2-(cyclohexyloxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(1-(4-methoxyphenyl)cyclohexyl)ethoxy)pyrimidin-4-yl)phenyl)propanoic acid
(2S)-2-amino-3-(4-(6-(2,2,2-trifluoro-1-(4-fluoro-2-methylphenyl)ethoxy)pyrimidin-4-yl)phenyl)propanoic acid
(2S)-2-amino-3-(4-(2-amino-6-(2,2,2-trifluoro-1-(4-fluoro-2-methylphenyl)ethoxy)pyrimidin-4-yl)phenyl)propanoic acid
(2S)-2-amino-3-(4-(2-amino-6-(oxazol-2-yl(phenyl)methoxy)pyrimidin-4-yl)phenyl)propanoic acid
(S)-2-amino-3-(4-(2-amino-6-(1-cyclohexyl-2,2,2-trifluoroethylideneaminooxy)pyrimidin-4-yl)phenyl)propanoic acid
(2S)-2-amino-3-(4-(2-amino-6-(1-(2-(3-(dimethylamino)phenyl)furan-3-yl)-2,2,2-trifluoroethoxy)pyrimidin-4-yl)phenyl)propanoic acid
(2S)-2-amino-3-(4-(2-amino-6-(2,2,2-trifluoro-1-(5-phenylthiophen-2-yl)ethoxy)pyrimidin-4-yl)phenyl)propanoic acid
(S)-phenyl 2-amino-3-(4-(2-amino-6-((R)-2,2,2-trifluoro-1-(3'-methoxybiphenyl-4-yl)ethoxy)pyrimidin-4-yl)phenyl)propanoate
(S)-2-amino-3-(4-(2-amino-6-((R)-1-(3'-((dimethylamino)methyl)biphenyl-4-yl)-2,2,2-trifluoroethoxy)pyrimidin-4-yl)phenyl)propanoic acid
(S)-2-amino-3-(4-(1-(3-methoxybenzoyl)-1H-pyrazol-4-yl)phenyl)propanoic acid
(2S)-2-amino-3-(4-(6-(2,2,2-trifluoro-1-(5-phenylfuran-2-yl)ethoxy)pyrimidin-4-yl)phenyl)propanoic acid
(2S)-2-amino-3-(4-(2-amino-6-(1-(4-chloro-2-fluorophenyl)-2,2,2-trifluoroethoxy)pyrimidin-4-yl)phenyl)propanoic acid
(S,E)-2-amino-3-(4-(2-amino-6-(4-(trifluoromethyl)styryl)pyrimidin-4-yl)phenyl)propanoic acid
(2S)-2-amino-3-(4-(2-amino-6-(1-(3,4-dichlorophenyl)-2,2,2-trifluoroethoxy)pyrimidin-4-yl)phenyl)propanoic acid
(2S)-2-amino-3-(4-(2-amino-6-(1-(4-chloro-3-fluorophenyl)-2,2,2-trifluoroethoxy)pyrimidin-4-yl)phenyl)propanoic acid
(S)-2-amino-3-(4-(2-amino-6-((R)-1-(3'-(dimethylamino)biphenyl-4-yl)-2,2,2-trifluoroethoxy)pyrimidin-4-yl)phenyl)propanoic acid
(2S)-2-amino-3-(4-(2-amino-6-(1-chloro-2,2,2-trifluoro-1-(4-methoxybiphenyl-2-yl)ethoxy)pyrimidin-4-yl)phenyl)propanoic acid
(2S)-2-amino-3-(4-(6-(2,2,2-trifluoro-1-(5-phenylthiophen-2-yl)ethoxy)pyrimidin-4-yl)phenyl)propanoic acid
(S)-2-amino-3-(4-(5-(4-phenoxyphenyl)-1H-1,2,3-triazol-1-yl)phenyl)propanoic acid
(S,E)-2-amino-3-(4-(2-amino-6-(2-(biphenyl-4-yl)vinyl)pyrimidin-4-yl)phenyl)propanoic acid
(S)-2-amino-3-(4-(4-amino-6-((R)-2,2,2-trifluoro-1-(3'-methoxybiphenyl-4-yl)ethoxy)pyrimidin-2-yl)phenyl)propanoic acid
(S)-2-amino-3-(4-(4'-methoxybiphenyl-4-ylsulfonamido)phenyl)propanoic acid
(2S)-2-amino-3-(4-(2-amino-6-(2,2,2-trifluoro-1-(6-(3-methoxyphenyl)pyridin-3-yl)ethoxy)pyrimidin-4-yl)phenyl)propanoic acid
(2S)-2-amino-3-(4-(2-amino-6-(2,2,2-trifluoro-1-(6-(2-fluoro-3-methoxyphenyl)pyridin-3-yl)ethoxy)pyrimidin-4-yl)phenyl)propanoic acid
2-amino-3-(5-(4'-methylbiphenyl-4-yl)-1H-indol-3-yl)propanoic acid
2-amino-3-(5-m-tolyl-1H-indol-3-yl)propanoic acid
(2S)-2-amino-3-(4-(2-(2-methoxyphenyl)furan-3-carboxamido)phenyl)propanoic acid
2-amino-3-(5-(1-benzyl-1H-pyrazol-4-yl)-1H-indol-3-yl)propanoic acid TABLE 2-continued (2S)-2-amino-3-(4-(2-amino-6-(2,2,2-trifluoro-1-(6-(thiophen-2-yl)pyridin-3-yl)ethoxy)pyrimidin-4-yl)phenyl)propanoic acid
2-amino-3-(6-(1-benzyl-1H-pyrazol-4-yl)-1H-indol-3-yl)propanoic acid
(S)-2-amino-3-(4-((2-(4-(trifluoromethyl)phenyl)thiazol-4-yl)methylamino)phenyl)propanoic acid
(S)-2-amino-3-(4-((4'-methoxybiphenyl-4-ylsulfonamido)methyl)phenyl)propanoic acid
(S)-2-amino-3-(4-(3-(2-methoxydibenzo[b,d]furan-3-yl)ureido)phenyl)propanoic acid
(S)-2-amino-3-(4-(3-(2,2-diphenylethyl)ureido)phenyl)propanoic acid
(S)-2-amino-3-(4-(phenylethynyl)phenyl)propanoic acid
(S)-2-amino-3-(4-(2-amino-6-((5-(1-methyl-5-(trifluoromethyl)-1H-pyrazol-3-yl)thiophen-2-yl)methoxy)pyrimidin-4-yl)phenyl)propanoic acid
(2S)-2-amino-3-(4-(2-amino-6-(1,1,1-trifluoro-3-((R)-2,2,3-trimethylcyclopent-3-enyl)propan-2-yloxy)pyrimidin-4-yl)phenyl)propanoic acid
(2S)-2-amino-3-(4-(2-amino-6-(3-(2-hydroxyethylcarbamoyl)piperidin-1-yl)pyrimidin-4-yl)phenyl)propanoic acid
(2S)-2-amino-3-(4-(2-amino-6-(3-(pyridin-2-yloxy)piperidin-1-yl)pyrimidin-4-yl)phenyl)propanoic acid
(S)-2-amino-3-(4-(2-amino-6-(4-chloro-3-(piperidine-1-carbonyl)phenyl)pyrimidin-4-yl)phenyl)propanoic acid In preferred embodiments, the TPH1 inhibitors disclosed above in Table 2 are administered to a patient in a dosage range of from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

In preferred embodiments, the TPH1 inhibitors disclosed above in Table 2 are administered to a patient in a dosage range of from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

The dosage of TPH1 inhibitors disclosed in Table 2 may depend on whether the TPH1 inhibitor is being administered for the prevention or for the treatment of a low bone mass disease. For prevention, preferred dose ranges include from about 5 mg/kg/day to about 250 mg/kg/day; from about 5 mg/kg/day to about 100 mg/kg/day; or from about 5 mg/kg/day to about 30 mg/kg/day; with about 10 mg/kg/day being especially preferred.

For treatment, preferred dose ranges for the TPH1 inhibitors disclosed in Table 2 include from about 10 mg/kg/day to about 250 mg/kg/day; from about 10 mg/kg/day to about 50 mg/kg/day; or from about 10 mg/kg/day to about 30 mg/kg/day; with about 25 mg/kg/day being especially preferred.

In certain embodiments, the TPH1 inhibitors disclosed herein reduces serum serotonin to a level that is at least about 10% less than the level before treatment with the TPH1 inhibitor. In certain embodiments, the TPH1 inhibitor reduces serum serotonin to a level that is about 10% less, about 20% less, about 30% less, about 40% less, about 50% less, about 60% less, about 70% less, about 80% less, or about 90% less, than the level before treatment with the TPH1 inhibitor.

Synthesis of the compounds described herein can be carried out by methods similar to those disclosed in U.S. Patent Application Publication 2007/0191370, U.S. Patent Application Publication 2008/0153852, U.S. Patent Application Publication 2009/0005381, and U.S. Patent Application Publication 2009/0029993. Moieties such as A, X, D, and E can be prepared and linked according to the methods described in those patent applications. By choosing suitable starting materials for the remaining portion of the structures disclosed herein, the remaining portion can be incorporated with the A-X-D or A-X-D-E portion in the final structure and thus the compounds disclosed herein can be prepared.

One skilled in the art would be guided by the Examples herein and could, for example, choose intermediates such as the following from Scheme 1 of Example 9

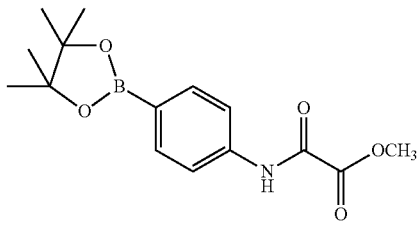 [SMILES: COC(=O)C(=O)Nc1ccc(B2OC(C)(C)C(C)(C)O2)cc1]

and link the intermediate compounds to suitable moieties such as A, $X_1$, D, and E that had been prepared according to the disclosures of the patent application described above. By choosing other intermediates similar to the intermediate shown above, one skilled in the art could readily synthesize other TPH1 inhibitors disclosed herein.

Synthesis of specific compounds disclosed herein as well as the compounds within the generic formulas disclosed herein can also be carried out by methods similar to those disclosed in International Patent Publication WO 2007/089335 and International Patent Publication WO 2008/073933. Moieties such as A, X, D, and E can be prepared and linked according to the methods described in WO 2007/089335, in particular the methods disclosed at pages 35-41. Further methods that can turned to for guidance are shown on pages 14-17 of WO 2008/073933. By choosing suitable starting materials for the remaining portion of the structures disclosed herein (e.g., the $X^1$-2-oxoacetate or $X^1$-2-oxoacetic acid moiety in certain of the generic formulas described above) the remaining portion can be incorporated with the A-X-D or A-X-D-E portion in the final structure and thus the compounds of the present invention can be prepared.

Certain compounds disclosed herein can be prepared according to the methods disclosed in International Patent Publication WO 2009/123978, incorporated herein by reference in its entirely and specifically for that purpose of its disclosure of the synthesis of the compounds disclosed herein.

The ability of selective TPH1 inhibitor CBMIDA to reduce peripheral serotonin measured in serum was tested. Either 250 or 500 mg/kg doses of CBMIDA were administered orally twice in 20 hours to 4 week old mice, 4-5 mice per group. As a control, some mice were untreated and some received 250 mg/kg pCPA orally. The results showed that there was a dose response to CBMIDA administration such that 250 mg/kg caused about a 45% reduction of peripheral serotonin, and 500 mg/kg reduced peripheral serotonin by about 80%. pCPA (250 mg/kg) caused about a 50% reduction of serum serotonin. These results showed that pCPA was more effective than CBMIDA and at the amounts used (250 mg/kg), pCPA did not cross the blood brain barrier. Therefore, pCPA did not decrease serotonin in the brain, where serotonin has the opposite effect of peripheral serotonin. CBMIDA has been reported to be a dually active bisphosphonate that is able to both inhibit bone resorption and stimulate bone formation in cell cultures (Xie et al., 2005, Bioorganic & Medicinal Chemistry Letters 15:3267-3270, incorporated herein by reference in its entirety).

The structures of CBMIDA and pCPA are as follows:

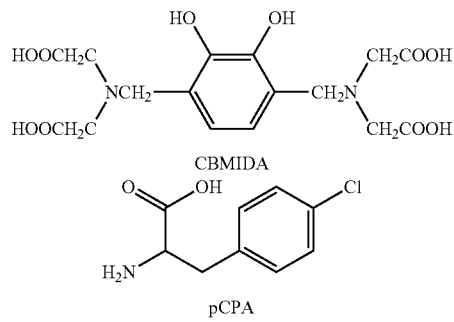

The present invention also encompasses the use of certain derivatives of the TPH1 inhibitors disclosed herein. For example, prodrugs of the TPH1 inhibitors could be produced by esterifying the carboxylic acid functions of the TPH1 inhibitors with a lower alcohol, e.g., methanol, ethanol, propanol, isopropanol, butanol, etc. The use of prodrugs of the TPH1 inhibitors that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the TPH1 inhibitors are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the TPH1 inhibitors disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

In certain embodiments, the TPH1 inhibitor inhibits TPH1 without significantly affecting the level of brain-derived serotonin. Methods of obtaining such inhibitors include: (1) screening for compounds that inhibit TPH1 to a much greater extent than TPH2; and (2) screening for compounds that, while they inhibit both TPH1 and TPH2, cannot cross the blood brain barrier and thus are effectively specific for TPH1 when administered to the patient outside the central nervous system. Of course, compounds that both inhibit TPH1 to a much greater extent than TPH2 and cannot cross the blood brain barrier are also suitable. Preferably, compounds that inhibit TPH1 to a much greater extent than TPH2 have an $IC_{50}$ for TPH2 that is at least about 10-fold greater than their $IC_{50}$ for TPH1.

In certain embodiments, the agent is a TPH1 inhibitor that does not significantly affect the level of expression of Type 1 collagen, osteocalcin, Runx2, Osterix, or Atf4 in osteoblasts. In certain embodiments, the agent is a TPH1 inhibitor that decreases the expression of Cyclin D1, D2 and E1 in osteoblasts.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

A chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

If the stereochemistry of a structure or a portion of a structure is not indicated with, for example, bold or dashed lines, the structure or the portion of the structure is to be interpreted as encompassing all stereoisomers of it, unless the chemical name associated with the structure indicates otherwise. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding the above, it is understood that the methods of the invention also encompass the use pure R and S enantiomers of the compounds disclosed herein as racemic mixtures. Thus, the disclose of a compound without indication of any particular stereochemistry should be considered a disclosure of the use of that compound in the form of all racemic mixtures (e.g., a mixture of about 50% R and 50% S enantiomers) as well as a disclosure of the use of essentially pure enantiomers (i.e., about 100% R or about 100% S enantiomers).

In certain embodiments of the invention, a therapeutically effective amount of one or more of the compounds described herein is administered alone or in combination with other compounds that are known to increase bone mass to a subject who has or is at risk of developing a low bone mass disease in order to treat or prevent such disease.

The efficacy of low bone density therapy by administering TPH1 inhibitors can be monitored by measuring bone density changes before and over time after treatment to determine drug efficacy.

The present invention provides a method of preventing or treating a low bone mass disease in a patient known or suspected to be in need of such prevention or treatment comprising administering to the patient a therapeutically effective amount of a compound that is a TPH1 inhibitor together with a serotonin receptor antagonist.

In certain embodiments, the serotonin receptor antagonist is an HT1B, HT2A or HT2B receptor antagonist. In preferred embodiments, the serotonin receptor antagonist is an HT1B antagonist.

The serotonin receptor antagonist may be one of the many known antagonists of peripheral serotonin receptors HT1B, HT2A or HT2B that are present on osteoblasts. Antagonists that are selective for HT1B, HT2A or HT2B receptors are preferred. The efficacy of low bone density therapy by administering HT1B, HT2A or HT2B antagonists can be monitored by measuring bone density changes before and over time after treatment to determine drug efficacy. Diseases associated with low bone mass can be treated with HT1B antagonists such as those listed in Table 3 below.

TABLE 3

| | |
|---|---|
| selective 5-HT1B antagonist GR 55562 | Mlinar and Corradetti, Neurosci., 2003, 18: 1559-1571 |
| elzasonan | U.S. patent Application |
| AZD1134 | Publication 2005/0203130 |
| AR-A2 | |
| trazodone hydrochloride (antidepressant) | U.S. Pat. No., 7,198,914 |
| highly selective 5-HT 1B antagonist (SB216641) | U.S. patent Application Publication 2006/0135415 |
| the selective antagonist at terminal 5-HT$_{1B}$ receptors, N-[3-(2-dimethylamino) ethoxy-4-methoxyphenyl]-2'-methyl-4'-(5-methyl-1,2,4-oxadiazol-3-yl)-(1,1'-biphenyl)-4-carboxamide (SB216641, 0.1-0.8 mg/kg) | Rojas-Corrales et al., Eur. J. Pharmacol., 511: 21-26 |
| GR 127,935 Mixed HT1B/1D antagonist | Naunyn Schmiedebergs Arch. Pharmacol., 1997, 355: 423-430; Wurch, et al., British J. Pharmacol., 1997, 120: 153-159 |
| Cyanopindolol -GR 125,743 Methiothepin ketanserin | J. Neurochem., 2000, 75: 2113-2122 2'-Methyl-4-(5-methyl-[1,2,4]oxadiazol-3-yl)-biphenyl-4-carboxylic acid [4-methoxy-3-(4-methyl-piperazin-1-yl)-phenyl]-amide (GR 127,935), ketanserin and methiothepin and each behaved as silent, competitive antagonists at rb 5-HT1B receptors British Journal of Pharmacology (1997) 120, 153 ± 159 |
| ICS 205-930 (Sandoz) is a selective antagonist at 5-hydroxytryptamine3 receptors and exerts marked effects on gastrointestinal motility in animalsGut specific | Br J Clin Pharmacol. 1989 September; 28(3): 315-322 |
| pindolol a beta-adrenoceptor blocker/5-hydroxytryptamine$_{1A/1B}$ receptor antagonist | Pindolol is also a nonselective beta blocker; rapidly and well absorbed from the GI tract |
| AR-A000002 - A Novel Selective 5-HT$_{1B}$ Antagonist anxiolytic and antidepressant potential of the selective 5-HT$_{1B}$ antagonist, AR-A000002 ((R)-N-[5-Methyl-8-(4-methylpiperazin-1-yl)-1,2,3,4-tetrahydro-2-naphthyl]-4- | Journal of Pharmacology And Experimental Therapeutics *Fast Forward* First published on November 25, 2002; |

TABLE 3-continued

| | |
|---|---|
| morpholinobenzamide). AR-A000002 functions as a 5-HT$_{1B}$ antagonist in vivo | |
| cyanopindolol, 5-HT-moduline and methiothepin | Daws, et al., Neuroscience Letters, 1999, 266: 165-168; Daws, et al., J. Neurochem., 2000, 75: 2113-2122 |
| GR 55562, a selective 5-HT1B antagonist selective 5-HT$_{1B}$ receptor antagonist 3-[3-(dimethylamino)propyl]-4-hydroxy-N-[4-(4-pyridinyl)phenyl]benzamide dihydrochloride (GR 55562; K$_B$≈100 nM) | British Journal of Pharmacology (2003) 138, 71-80 |
| SB224289 | Brain Res. 2004 May 8; 1007(1-2): 86-97 |
| SB 216641 | Roca-Vinardell et al., Anesthesiology, 2003, 98: 741-747 |
| Nonselective 5-HT(1B/D) receptor antagonists such as ketanserin, ritanserin and methiothepin | |

In certain embodiments, the TPH1 inhibitor and the serotonin receptor antagonist are administered together in a single pharmaceutical composition. In other embodiments, the TPH1 inhibitor and the serotonin receptor antagonist are administered in separate pharmaceutical compositions.

In certain embodiments of the methods described herein, the low bone mass disease is osteoporosis, osteoporosis pseudoglioma syndrome (OPPG), osteopenia, osteomalacia, renal osteodystrophy, faulty bone formation, faulty bone resorption, Paget's disease, bone fracture, broken bones, or bone metastasis. In preferred embodiments, the low bone mass disease is osteoporosis.

The amount of compounds disclosed herein to be administered to a patient depends on many factors, as discussed herein. However, in humans, for example, the amount may range from about 1 mg/day to about 2 g/day; preferably from about 15 mg/day to about 500 mg/day; or from about 20 mg/day to about 250 mg/day; or from about 40 mg/day to about 100 mg/day. Other preferred dosages include about 2 mg/day, about 5 mg/day, about 10 mg/day, about 15 mg/day, about 20 mg/day, about 25 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 250 mg/day, about 300 mg/day, about 350 mg/day, about 400 mg/day, about 500 mg/day, about 600 mg/day, about 700 mg/day, about 800 mg/day, and about 900 mg/day.

Other dose ranges that may be used include from about 50 mg/day to about 15 g/day; from about 50 mg/day to about 10 g/day; from about 50 mg/day to about 5 g/day; from about 50 mg/day to about 1 g/day; from about 50 mg/day to about 900 mg/day; from about 50 mg/day to about 800 mg/day; from about 50 mg/day to about 700 mg/day; from about 50 mg/day to about 600 mg/day; from about 50 mg/day to about 500 mg/day; from about 50 mg/day to about 400 mg/day; from about 50 mg/day to about 300 mg/day; or from about 50 mg/day to about 200 mg/day.

Other dose ranges that may be used include from about 100 mg/day to about 15 g/day; from about 100 mg/day to about 10 g/day; from about 100 mg/day to about 5 g/day; from about 100 mg/day to about 1 g/day; from about 100 mg/day to about 900 mg/day; from about 100 mg/day to about 800 mg/day; from about 100 mg/day to about 700 mg/day; from about 100 mg/day to about 600 mg/day; from about 100 mg/day to about 500 mg/day; from about 100 mg/day to about 400 mg/day; from about 100 mg/day to about 300 mg/day; or from about 100 mg/day to about 200 mg/day.

Other dose ranges that may be used include from about 200 mg/day to about 15 g/day; from about 200 mg/day to about 10 g/day; from about 200 mg/day to about 5 g/day; from about 200 mg/day to about 1 g/day; from about 200 mg/day to about 900 mg/day; from about 200 mg/day to about 800 mg/day; from about 200 mg/day to about 700 mg/day; from about 200 mg/day to about 600 mg/day; from about 200 mg/day to about 500 mg/day; from about 200 mg/day to about 400 mg/day; or from about 200 mg/day to about 300 mg/day.

Other dose ranges that may be used include from about 300 mg/day to about 15 g/day; from about 300 mg/day to about 10 g/day; from about 300 mg/day to about 5 g/day; from about 300 mg/day to about 1 g/day; from about 300 mg/day to about 900 mg/day; from about 300 mg/day to about 800 mg/day; from about 300 mg/day to about 700 mg/day; from about 300 mg/day to about 600 mg/day; from about 300 mg/day to about 500 mg/day; or from about 300 mg/day to about 400 mg/day.

Other dose ranges that may be used include from about 400 mg/day to about 15 g/day; from about 400 mg/day to about 10 g/day; from about 400 mg/day to about 5 g/day; from about 400 mg/day to about 1 g/day; from about 400 mg/day to about 900 mg/day; from about 400 mg/day to about 800 mg/day; from about 400 mg/day to about 700 mg/day; from about 400 mg/day to about 600 mg/day; or from about 400 mg/day to about 500 mg/day.

Other dose ranges that may be used include from about 500 mg/day to about 15 g/day; from about 500 mg/day to about 10 g/day; from about 500 mg/day to about 5 g/day; from about 500 mg/day to about 4 g/day; from about 500 mg/day to about 3 g/day; from about 500 mg/day to about 2 g/day; from about 500 mg/day to about 1 g/day; from about 500 mg/day to about 900 mg/day; from about 500 mg/day to about 800 mg/day; from about 500 mg/day to about 700 mg/day; or from about 500 mg/day to about 600 mg/day.

Other dose ranges that may be used include from about 600 mg/day to about 15 g/day; from about 600 mg/day to about 10 g/day; from about 600 mg/day to about 5 g/day; from about 600 mg/day to about 4 g/day; from about 600 mg/day to about 3 g/day; from about 600 mg/day to about 2 g/day; from about 600 mg/day to about 1 g/day; from about 600 mg/day to about 900 mg/day; from about 600 mg/day to about 800 mg/day; or from about 600 mg/day to about 700 mg/day.

Other dose ranges that may be used include from about 700 mg/day to about 15 g/day; from about 700 mg/day to about 10 g/day; from about 700 mg/day to about 5 g/day; from about 700 mg/day to about 4 g/day; from about 700 mg/day to about 3 g/day; from about 700 mg/day to about 2 g/day; from about 700 mg/day to about 1 g/day; from about 700 mg/day to about 900 mg/day; or from about 700 mg/day to about 800 mg/day.

Other dose ranges that may be used include from about 800 mg/day to about 15 g/day; from about 800 mg/day to about 10 g/day; from about 800 mg/day to about 5 g/day; from about 800 mg/day to about 4 g/day; from about 800 mg/day to about 3 g/day; from about 800 mg/day to about 2 g/day; from about 800 mg/day to about 1 g/day; or from about 800 mg/day to about 900 mg/day.

Other dose ranges that may be used include from about 900 mg/day to about 15 g/day; from about 900 mg/day to about 10 g/day; from about 900 mg/day to about 5 g/day; from about 900 mg/day to about 4 g/day; from about 900 mg/day to about 3 g/day; from about 900 mg/day to about 2 g/day; or from about 900 mg/day to about 1 g/day.

Other dose ranges that may be used include from about 1 g/day to about 15 g/day; from about 1 g/day to about 10 g/day; from about 1 g/day to about 5 g/day; from about 1 g/day to about 4 g/day; from about 1 g/day to about 3 g/day; or from about 1 g/day to about 2 g/day.

Other dosages that may be used include from about 1 g/day, about 2 g/day, about 3 g/day, about 4 g/day, about 5 g/day, about 6 g/day, about 7 g/day, about 8 g/day, about 9 g/day, about 10 g/day, about 11 g/day, about 12 g/day, about 13 g/day, about 14 g/day, or about 15 g/day.

The amount of compound disclosed herein to be administered to a patient may range from about 5 mg/kg/day to about 500 mg/kg/day, from about 5 mg/kg/day to about 400 mg/kg/day, from about 5 mg/kg/day to about 300 mg/kg/day, from about 5 mg/kg/day to about 250 mg/kg/day, from about 5 mg/kg/day to about 200 mg/kg/day, from about 5 mg/kg/day to about 150 mg/kg/day, from about 5 mg/kg/day to about 100 mg/kg/day, from about 5 mg/kg/day to about 75 mg/kg/day, from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

Other dose ranges that may be used include from about 10 mg/kg/day to about 500 mg/kg/day, from about 10 mg/kg/day to about 400 mg/kg/day, from about 10 mg/kg/day to about 300 mg/kg/day, from about 10 mg/kg/day to about 250 mg/kg/day, from about 10 mg/kg/day to about 200 mg/kg/day, from about 10 mg/kg/day to about 150 mg/kg/day, from about 10 mg/kg/day to about 100 mg/kg/day, from about 10 mg/kg/day to about 75 mg/kg/day, from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

Other dose ranges that may be used include from about 15 mg/kg/day to about 500 mg/kg/day, from about 15 mg/kg/day to about 400 mg/kg/day, from about 15 mg/kg/day to about 300 mg/kg/day, from about 15 mg/kg/day to about 250 mg/kg/day, from about 15 mg/kg/day to about 200 mg/kg/day, from about 15 mg/kg/day to about 150 mg/kg/day, from about 15 mg/kg/day to about 100 mg/kg/day, from about 15 mg/kg/day to about 75 mg/kg/day, from about 15 mg/kg/day to about 50 mg/kg/day, from about 15 mg/kg/day to about 40 mg/kg/day, from about 15 mg/kg/day to about 30 mg/kg/day, from about 15 mg/kg/day to about 25 mg/kg/day, or from about 15 mg/kg/day to about 20 mg/kg/day.

Other dose ranges that may be used include from about 20 mg/kg/day to about 500 mg/kg/day, from about 20 mg/kg/day to about 400 mg/kg/day, from about 20 mg/kg/day to about 300 mg/kg/day, from about 20 mg/kg/day to about 250 mg/kg/day, from about 20 mg/kg/day to about 200 mg/kg/day, from about 20 mg/kg/day to about 150 mg/kg/day, from about 20 mg/kg/day to about 100 mg/kg/day, from about 20 mg/kg/day to about 75 mg/kg/day, from about 20 mg/kg/day to about 50 mg/kg/day, from about 20 mg/kg/day to about 40 mg/kg/day, from about 20 mg/kg/day to about 30 mg/kg/day, or from about 20 mg/kg/day to about 25 mg/kg/day.

Other dose ranges that may be used include from about 25 mg/kg/day to about 500 mg/kg/day, from about 25 mg/kg/day to about 400 mg/kg/day, from about 25 mg/kg/day to about 300 mg/kg/day, from about 25 mg/kg/day to about 250 mg/kg/day, from about 25 mg/kg/day to about 200 mg/kg/day, from about 25 mg/kg/day to about 150 mg/kg/day, from about 25 mg/kg/day to about 100 mg/kg/day, from about 25 mg/kg/day to about 75 mg/kg/day, from about 25 mg/kg/day to about 50 mg/kg/day, from about 25 mg/kg/day to about 40 mg/kg/day, or from about 25 mg/kg/day to about 30 mg/kg/day.

Other dose ranges that may be used include from about 30 mg/kg/day to about 500 mg/kg/day, from about 30 mg/kg/day to about 400 mg/kg/day, from about 30 mg/kg/day to about 300 mg/kg/day, from about 30 mg/kg/day to about 250 mg/kg/day, from about 30 mg/kg/day to about 200 mg/kg/day, from about 30 mg/kg/day to about 150 mg/kg/day, from about 30 mg/kg/day to about 100 mg/kg/day, from about 30 mg/kg/day to about 75 mg/kg/day, from about 30 mg/kg/day to about 50 mg/kg/day, or from about 30 mg/kg/day to about 40 mg/kg/day.

Other dose ranges that may be used include from about 40 mg/kg/day to about 500 mg/kg/day, from about 40 mg/kg/day to about 400 mg/kg/day, from about 40 mg/kg/day to about 300 mg/kg/day, from about 40 mg/kg/day to about 250 mg/kg/day, from about 40 mg/kg/day to about 200 mg/kg/day, from about 40 mg/kg/day to about 150 mg/kg/day, from about 40 mg/kg/day to about 100 mg/kg/day, from about 40 mg/kg/day to about 75 mg/kg/day, from about 40 mg/kg/day to about 60 mg/kg/day, or from about 40 mg/kg/day to about 50 mg/kg/day.

Other dose ranges that may be used include from about 50 mg/kg/day to about 500 mg/kg/day, from about 50 mg/kg/day to about 400 mg/kg/day, from about 50 mg/kg/day to about 300 mg/kg/day, from about 50 mg/kg/day to about 250 mg/kg/day, from about 50 mg/kg/day to about 200 mg/kg/day, from about 50 mg/kg/day to about 175 mg/kg/day, from about 50 mg/kg/day to about 150 mg/kg/day, from about 50 mg/kg/day to about 125 mg/kg/day, from about 50 mg/kg/day to about 100 mg/kg/day, from about 50 mg/kg/day to about 75 mg/kg/day, or from about 50 mg/kg/day to about 60 mg/kg/day.

Other dose ranges that may be used include from about 60 mg/kg/day to about 500 mg/kg/day, from about 60 mg/kg/day to about 400 mg/kg/day, from about 60 mg/kg/day to about 300 mg/kg/day, from about 60 mg/kg/day to about 250 mg/kg/day, from about 60 mg/kg/day to about 200 mg/kg/day, from about 60 mg/kg/day to about 175 mg/kg/day, from about 60 mg/kg/day to about 150 mg/kg/day, from about 60 mg/kg/day to about 125 mg/kg/day, from about 60 mg/kg/day to about 100 mg/kg/day, or from about 60 mg/kg/day to about 75 mg/kg/day.

Other dose ranges that may be used include from about 70 mg/kg/day to about 500 mg/kg/day, from about 70 mg/kg/day to about 400 mg/kg/day, from about 70 mg/kg/day to about 300 mg/kg/day, from about 70 mg/kg/day to about 250 mg/kg/day, from about 70 mg/kg/day to about 200 mg/kg/day, from about 70 mg/kg/day to about 175 mg/kg/day, from about 70 mg/kg/day to about 150 mg/kg/day, from about 70 mg/kg/day to about 125 mg/kg/day, or from about 70 mg/kg/day to about 100 mg/kg/day.

Other dose ranges that may be used include from about 80 mg/kg/day to about 500 mg/kg/day, from about 80 mg/kg/day to about 400 mg/kg/day, from about 80 mg/kg/day to about 300 mg/kg/day, from about 80 mg/kg/day to about 250 mg/kg/day, from about 80 mg/kg/day to about 200 mg/kg/day, from about 80 mg/kg/day to about 175 mg/kg/day, from about 80 mg/kg/day to about 150 mg/kg/day, from about 80 mg/kg/day to about 125 mg/kg/day, or from about 80 mg/kg/day to about 100 mg/kg/day.

Other dose ranges that may be used include from about 90 mg/kg/day to about 500 mg/kg/day, from about 90 mg/kg/day to about 400 mg/kg/day, from about 90 mg/kg/day to about 300 mg/kg/day, from about 90 mg/kg/day to about 250 mg/kg/day, from about 90 mg/kg/day to about 200 mg/kg/day, from about 90 mg/kg/day to about 175 mg/kg/day, from about 90 mg/kg/day to about 150 mg/kg/day, from about 90 mg/kg/day to about 125 mg/kg/day, or from about 90 mg/kg/day to about 100 mg/kg/day.

Other dose ranges that may be used include from about 100 mg/kg/day to about 500 mg/kg/day, from about 100 mg/kg/day to about 400 mg/kg/day, from about 100 mg/kg/day to about 300 mg/kg/day, from about 100 mg/kg/day to about 250 mg/kg/day, from about 100 mg/kg/day to about 200 mg/kg/day, from about 100 mg/kg/day to about 175 mg/kg/day, from about 100 mg/kg/day to about 150 mg/kg/day, or from about 100 mg/kg/day to about 125 mg/kg/day.

Other dosages that may be used include about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 45 mg/kg/day, about 50 mg/kg/day, about 60 mg/kg/day, about 70 mg/kg/day, about 80 mg/kg/day, about 90 mg/kg/day, about 100 mg/kg/day, about 125 mg/kg/day, about 150 mg/kg/day, about 175 mg/kg/day, about 200 mg/kg/day, about 250 mg/kg/day, or about 350 mg/kg/day.

Routine experimentation will determine the appropriate value for each patient by monitoring the compound's effect on serum serotonin levels, which can be frequently and easily monitored. The agent can be administered once or multiple times per day. Serum serotonin levels can be monitored before and during therapy to determine the appropriate amount of TPH1 inhibitor to administer to lower serum serotonin levels or bring serum serotonin levels to normal and to maintain normal levels over extended periods of time. In a preferred embodiment, a patient is tested to determine if his/her serum serotonin levels are significantly elevated above normal levels (about 25% above) before administering treatment with TPH1 inhibitors and/or HT1B, HT2A or HT2B receptor antagonists. The frequency of administration may vary from a single dose per day to multiple doses per day. Preferred routes of administration include oral, intravenous and intraperitoneal, but other forms of administration may be chosen as well.

Another embodiment of the present invention is directed to pharmaceutical formulations of TPH1 inhibitors combined with SSRIs for administration to a subject being treated with long term SSRI administration, in order to prevent bone loss or to maintain or increase normal bone mass.

In certain embodiments, the therapeutic agents of the invention act selectively on peripheral serotonin or are administered in an amount that decreases serum serotonin without increasing brain-derived serotonin.

In other embodiments, the TPH1 inhibitors and serotonin receptor antagonists are formulated and administered together with bisphosphonates such as FOSAMAX® (alendronate sodium), FOSAMAX PLUS D™ (alendronate sodium/cholecalciferol), BONIVA® (ibandronate sodium) or other bone building drugs, vitamins or minerals to potentiate their effects on increasing bone mass.

Monitoring the therapeutic efficacy of TPH1 inhibitors and serotonin synthesis inhibitors is straightforward, as one can administer the inhibitors in an amount and for a duration that reduces peripheral serum serotonin levels, and over time increases bone mass. Both serum serotonin and bone mass can be easily measured. Example 1 provides the details of one immunoassay for monitoring the level of serum serotonin. Example 3 provides further assays for serum serotonin that may be used. Monitoring serum serotonin is simple and can be done frequently during the course of therapy to establish the appropriate dose for each patient. Any method known in the art for assaying serum serotonin can be used. Increased bone mass can be measured as described herein using various means of measuring bone density and markers of bone growth or can be measured by other methods known in the art.

U.S. Provisional Patent Application Ser. No. 60/976,403, filed Sep. 28, 2007, and International Patent Application PCT/US08/77870, filed Sep. 26, 2008 and published Apr. 9, 2009 as WO 2009/045900, incorporated by reference herein in their entireties, disclose that brain-derived serotonin increases bone mass and decreases sympathetic tone. Another embodiment of the present invention for treating or preventing low bone mass diseases is directed to methods for treating or preventing low bone mass by administering agents that decrease sympathetic tone, such as beta blockers, together with a TPH1 inhibitor, optionally with an HT1B, HT2A or HT2B serotonin receptor antagonist. The use of any compound that decreases sympathetic tone comes within the scope of the invention. Preferably the compound is a beta-2 receptor antagonist, many of which are described in the art. Among the beta blockers that can be used are three beta-2 specific blockers that can be used to reduce sympathetic tone and increase bone mass in combination with TPH1 inhibitors described herein: IPS339, ICI118,551, and Sandoz L1 32-468 (Br. J. Ophthalmol. 1984 April; 68(4): 245-247). Butaxamine is also a beta-2 blocker that may be used in the present invention. Non-selective beta blockers include: metipranolol, nadol (a beta-specific sympatholytic which non-selectively blocks beta-2 adrenergic receptors); oxprenolol (a lipophilic beta blocker which passes the blood-brain barrier more easily than water soluble beta blockers), penbutolol, pindolol (a beta blocker that acts on serotonin 5-HT1A receptors in the brain, resulting in increased postsynaptic serotonin concentrations), and propranolol (known to readily cross the blood-brain barrier, timolol and sotalol. The beta blockers can be administered together with agents that directly or indirectly increase brain-derived serotonin, including HT2C receptor agonists, agents that increase TPH2 activity or expression, and agents that specifically decrease reuptake of BDS.

Certain other embodiments of the invention are directed to a pharmaceutical composition that includes a TPH1 inhibitor and an HT1B, HT2A or HT2B antagonist administered separately at one or more times on the same day, or over a period of days, sometimes alternating administration of the various respective agents.

Some embodiments are directed to pharmaceutical compositions for treating or preventing anxiety or depression that include both SSRIs and drugs that reduce the level of serum serotonin (e.g., TPH1 inhibitors, optionally with HT1B antagonists) in order to prevent patients who take serotonin reuptake inhibitors from developing osteoporosis. These preparations would permit the SSRIs to elevate brain-derived serotonin to treat anxiety without increasing peripheral serotonin, which can cause low bone mass diseases like osteoporosis.

Elevated brain-derived serotonin increases bone mass by acting through HT2C receptors on target neurons in the hypothalamus. Thus, some embodiments of the present invention include administering combination drug therapy using pharmaceuticals that decrease peripheral serotonin and increase brain-derived serotonin. For example, an HT2C agonist may be combined with a TPH1 inhibitor.

In certain embodiments, the methods of the present invention comprise the step of identifying a patient in need of therapy for a low bone mass disease. Thus, the present invention provides a method comprising:

(a) identifying a patient in need of therapy for a low bone mass disease;

(b) administering to the patient a therapeutically effective amount of an agent that decreases serum serotonin levels.

The present invention encompasses the use of a TPH1 inhibitor, optionally together with a serotonin receptor antagonist (e.g., an HT1B antagonist), for the manufacture of a medicament for preventing or treating a low bone mass disease (e.g., osteoporosis). The present invention encompasses the use of a TPH1 inhibitor, optionally together with a serotonin receptor antagonist (e.g., an HT1B antagonist) for preventing or treating a bone disease (e.g., osteoporosis). In certain embodiments, the present invention encompasses the use of a compound selected from compounds (1)-(120) optionally together with a serotonin receptor antagonist (e.g., an HT1B antagonist), for the manufacture of a medicament for preventing or treating a low bone mass disease (e.g., osteoporosis). In certain embodiments, the present invention encompasses the use of a compound selected from compounds (102)-(120) for use as a medicament. In certain embodiments, the present invention encompasses the use of a compound selected from compounds (102)-(120) for use in the treatment of a disease or disorder mediated by peripheral serotonin (e.g., osteoporosis). In certain embodiments, the present invention encompasses the use of a compound selected from compounds (102)-(120), optionally together with a serotonin receptor antagonist (e.g., an HT1B antagonist), for the manufacture of a medicament for preventing or treating diseases or disorders mediated by peripheral serotonin (e.g., osteoporosis).

Pharmaceutical Compositions

Therapeutic agents such as the TPH1 inhibitors, serotonin receptor antagonists, serotonin receptor agonists, SSRIs, and beta blockers described herein may be formulated into pharmaceutical compositions. The therapeutic agents may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount of a TPH1 inhibitor or serotonin receptor antagonist.

Pharmaceutically acceptable derivatives of any of the TPH1 inhibitors, serotonin receptor antagonists, or serotonin receptor agonists described herein come within the scope of the invention. A "pharmaceutically acceptable derivative" of a TPH1 inhibitor, serotonin receptor antagonist, or serotonin receptor agonist means any non-toxic derivative of a TPH1 inhibitor, serotonin receptor antagonist, or serotonin receptor agonist described herein that, upon administration to a recipient, exhibits that same or similar biological activity with respect to reducing serum serotonin expression or modulating serotonin receptor activity as the TPH1 inhibitor, serotonin receptor antagonist, or serotonin receptor agonists described herein.

Pharmaceutically acceptable salts of the therapeutic agents described herein for use in treating or preventing bone diseases associated with abnormally low bone mass, include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the therapeutic agents disclosed herein. Water or oil-soluble or dispersible products may be obtained by such quaternization.

The therapeutic agents of the present invention are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of the present invention are also meant to include compounds which differ only in the presence of one or more isotopically enriched atoms. For example, therapeutic agents in which a molecule of hydrogen is replaced by deuterium or tritium, or the replacement of a carbon molecule by $^{13}C$- or $^{14}C$-enriched carbon are within the scope of this invention.

In a preferred embodiment, the therapeutic agents of the present invention are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the compound with which it is formulated. Pharmaceutically acceptable carriers, adjuvants or vehicles that may be used in the pharmaceutical compositions of this invention encompass any of the standard pharmaceutically accepted solid carriers as well as liquid carriers such as a phosphate-buffered saline solution, water, as well as emulsions such as an oil/water emulsion or a triglyceride emulsion. An example of an acceptable triglyceride emulsion useful in the intravenous and intraperitoneal administration of the compounds is the triglyceride emulsion commercially known as INTRALIPID®, Solid carriers may include excipients such as starch, milk, sugar, certain types of clay, stearic acid, talc, gums, glycols, or other known excipients. Carriers may also include flavor and color additives or other ingredients.

In the practice of the invention, the pharmaceutical compositions of the present invention are preferably administered orally. However, the pharmaceutical compositions may be administered parenterally, by inhalation spray, topically, rectally, nasally, buccally, vaginally or via an implanted reservoir. Preferably, the pharmaceutical compositions are administered orally, intraperitoneally or intravenously. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions of this invention may also be administered by nasal aerosol or inhalation. Such pharmaceutical compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

Where the pharmaceutical compositions contain both agents that act peripherally like HT1B antagonists or TPH1 inhibitors and agents that act centrally like HT2C agonists, the compositions can be formulated to increase delivery of the centrally acting therapeutic agents to the central nervous system. If a compound having therapeutic utility does not easily cross the blood brain barrier, it can be modified using various methods in medicinal chemistry known in the art that attach various side groups to improve permeability through the blood brain barrier.

Serotonin receptor antagonists (e.g., HT1B receptor antagonists) can be derivatized or otherwise designed to enhance uptake by bone, using medicinal chemistry methods known in the art.

The TPH1 inhibitors and HT1B antagonists of the present invention can be derivatized by the formation of a reversible linkage with one or more suitable groups to yield "pro-drugs," i.e., chemical derivatives that, after absorption by the host, are converted into the parent compound. Liberation of the parent compound may be by chemical hydrolysis or enzymatic attack. A derivative or pro-drug can have enhanced permeability for the target organ. In the case of TPH1 inhibitors, the target organ is the duodenum where 95% of peripheral serotonin is made. HT1B antagonists could be formulated to have enhanced penetration of bone to reach the osteoblast target. The prodrug has an enhanced permeability according to the present invention if, after administration of the pro-drug or derivative thereof to a living organism, a higher amount of the compound reaches the target organ, resulting in a higher level of effective agent, as compared to administration of the base compound without derivatization.

The amount of the therapeutic agents of the present invention that may be combined with the carrier materials to produce a pharmaceutical composition in a single dosage form will vary depending upon the host treated and the particular mode of administration. It should be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician as well as the severity of the particular disease being treated. Despite their variety, accounting for these factors in order to select an appropriate dosage or treatment regimen would require no more than routine experimentation.

The dosage of TPH1 inhibitor administered may also depend on whether the TPH1 inhibitor is being administered for the prevention or for the treatment of a low bone mass disease. For prevention, preferred dose ranges include from about 5 mg/kg/day to about 250 mg/kg/day; from about 5 mg/kg/day to about 100 mg/kg/day; or from about 5 mg/kg/day to about 30 mg/kg/day; with about 10 mg/kg/day being especially preferred.

For treatment, preferred dose ranges include from about 10 mg/kg/day to about 250 mg/kg/day; from about 10 mg/kg/day to about 50 mg/kg/day; or from about 10 mg/kg/day to about 30 mg/kg/day; with about 25 mg/kg/day being especially preferred.

Additional therapeutic agents, which are normally administered to treat bone diseases associated with abnormally high or abnormally low bone mass, may also be present in the pharmaceutical compositions of this invention. As used herein, additional therapeutic agents that are normally administered to treat a particular disease, or condition, are known as "appropriate for the disease, or condition, being treated." Examples of appropriate agents for osteoporosis include FOSAMAX®, other bisphosphonates, FORTEO® (parathyroid hormone) and beta-blockers. Those additional agents may be administered separately from the therapeutic agents of the invention, as part of a multiple dosage regimen. Alternatively, those agents may be part of a single dosage form, mixed together with the therapeutic agents of the invention in a single pharmaceutical composition. If administered as part of a multiple dosage regime, the two active agents may be administered simultaneously, sequentially or within a period of time from one another. The amount of both the therapeutic agent of the invention and the additional therapeutic agent (in those compositions which comprise an additional therapeutic agent as described above) that may be combined with the carrier materials to produce a single dosage form will vary depending upon the host treated and the particular mode of administration as well as on the nature of the therapeutic agent of the invention and the additional therapeutic agent.

Assays for TPH1 Inhibiting Activity

The ability of the compounds disclosed herein to inhibit TPH1 may be assayed by any methods known in the art. In particular, the ability of the compounds disclosed herein to inhibit TPH1 may be assayed by a method comprising:

(a) providing a source of TPH1;

(b) exposing the source of TPH1 to L-tryptophan in the absence of a compound disclosed herein;

(c) measuring the amount of 5-hydroxytryptophan produced by the source of TPH1 in the absence of the compound disclosed herein;

(d) exposing the source of TPH1 to L-tryptophan in the presence of the compound disclosed herein;

(e) measuring the amount of 5-hydroxytryptophan produced by the source of TPH1 in the presence of the compound disclosed herein;

(f) comparing the amount of 5-hydroxytryptophan produced by the source of TPH1 in the presence of the compound disclosed herein to the amount of 5-hydroxytryptophan produced by the source of TPH1 in the absence of the compound disclosed herein, thus determining the ability of the compound disclosed herein to inhibit TPH1.

In certain embodiments, the method described above includes the further step of administering the compound disclosed herein to a patient in need of therapy for a low bone mass disease.

In certain embodiments, the source of TPH1 is an isolated TPH1 enzyme, preferably human. Isolated TPH1 can be produced by in vitro expression of TPH1, e.g., in a coupled in vitro transcription/translation system. Alternatively, the source of TPH1 may be partially or highly purified preparations from cells expressing TPH1. In other embodiments, the source of TPH1 is a whole cell expressing TPH1, preferably human. In some embodiments, the whole cell has been transfected with a expression vector comprising TPH1 so that the cell expresses recombinant TPH1, preferably human.

The mRNA and amino acid sequence of human TPH1 can be found in GenBank, at accession no. X52836. The genomic sequence can be found at AF057280. These nucleotide sequences can be used in methods well-known in the art to construct suitable expression vectors for expressing TPH1 recombinantly in cells, or in vitro.

Activators of TPH2 may be identified by a method comprising:

(a) providing a source of TPH2;

(b) exposing the source of TPH2 to L-tryptophan in the absence of a candidate compound;

(c) measuring the amount of 5-hydroxytryptophan produced by the source of TPH2 in the absence of the candidate compound;

(d) exposing the source of TPH2 to L-tryptophan in the presence of the candidate compound;

(e) measuring the amount of 5-hydroxytryptophan produced by the source of TPH2 in the presence of the candidate compound;

(f) where, if the amount of 5-hydroxytryptophan produced by the source of TPH2 in the presence of the candidate compound is greater than the amount of 5-hydroxytryptophan produced by the source of TPH2 in the absence of the candidate compound, the candidate compound is a TPH2 activator.

"Greater than" for the purpose of the herein-described methods of identifying TPH2 activators from a collection of candidate compounds refers to an amount that would not be attributed by those of skill in the art to normal variation seen in the method. Preferably, "greater than" is at least about 50%, at least about 75%, at least about 100%, at least about 250%, or at least about 500% more than the amount observed in the absence of the candidate compound.

In certain embodiments, the method described above includes the further step of administering the TPH2 activator identified in step (f) to a patient I need of therapy for a low bone mass disease.

In certain embodiments, the source of TPH2 is an isolated TPH2 enzyme, preferably human. Isolated TPH2 can be produced by in vitro expression of TPH1, e.g., in a coupled in vitro transcription/translation system. Alternatively, the source of TPH2 may be partially or highly purified preparations from cells expressing TPH2. In other embodiments, the source of TPH2 is a whole cell expressing TPH2, preferably human. In some embodiments, the whole cell has been transfected with an expression vector comprising TPH2 so that the cell expresses recombinant TPH2, preferably human.

The mRNA and amino acid sequence of human TPH2 can be found in GenBank, at accession no. AY098914. The genomic sequence can be found at AC090109. These nucleotide sequences can be used in methods well-known in the art to construct suitable expression vectors for expressing TPH2 recombinantly in cells, or in vitro.

Antagonists of a serotonin receptor may be identified by a method comprising:

(a) providing a cell expressing the serotonin receptor;

(b) exposing the cell expressing the serotonin receptor to serotonin or a serotonin analogue in the absence of a candidate compound;

(c) measuring the activation of the serotonin receptor in the absence of the candidate compound;

(d) exposing the cell expressing the serotonin receptor to serotonin or a serotonin analogue in the presence of a candidate compound;

(e) measuring the activation of the serotonin receptor in the presence of the candidate compound;

(f) where, if the amount of activation of the serotonin receptor in the presence of the candidate compound is less than the amount of activation of the serotonin receptor in the absence of the candidate compound, the candidate compound is a serotonin receptor antagonist.

Antagonists of a serotonin receptor may also be identified by a method comprising:

(a) providing a cell expressing the serotonin receptor;

(b) exposing the cell expressing the serotonin receptor to serotonin or a serotonin analogue in the absence of a candidate compound;

(c) measuring the binding of the serotonin or the serotonin analogue to the serotonin receptor in the absence of the candidate compound;

(d) exposing the cell expressing the serotonin receptor to serotonin or a serotonin analogue in the presence of a candidate compound;

(e) measuring the binding of the serotonin or the serotonin analogue to the serotonin receptor in the presence of the candidate compound;

(f) where, if the binding of the serotonin or the serotonin analogue to the serotonin receptor in the presence of the candidate compound is less than the binding of the serotonin or the serotonin analogue to the serotonin receptor in the absence of the candidate compound, the candidate compound is a serotonin receptor antagonist.

By "serotonin analogue" is meant a substance that binds to a serotonin receptor with binding characteristics similar to those of serotonin and/or activates a serotonin receptor in a manner similar to that of serotonin.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1

Assessment of Effect of Catechol-3,6-bis methyleneiminodiacetic acid (CBMIDA) on Peripheral Serotonin Production in Mice Animals One month old C57B1/6 inbred male mice, weighing 15-16 g were used in the experiments. Animals were housed under 12 h light/12 h dark conditions in a room with controlled temperature (22° C.) and humidity (60%). Mice had ad libitum access to food and water, and were used after a minimum of 4 days of acclimatization to the housing conditions. All experiments were conducted following Columbia University Guidelines for the Animal Use and Care of laboratory mice.

Experimental Protocol

Before the experiments, animals were separated into individual cages one day prior to the experiment. Compounds were fed orally (gavage) to the mouse, calculated according to the weight of the mouse, twice a day at 1700 h and at 1100 h. Oral feeding was selected over intravenous or intraperitoneal infusion of the compound for better inhibition of Tryptophan hydroxylase-1 (TPH1) present in the gut vs TPH2 that synthesizes serotonin and is present in the brain, TPH2. This route created two potential barriers for the compound to reach the brain. First, the intestinal blood barrier that has poor permeability to the EDTA-based compounds (as is the case with CBMIDA), hence does not allow all the amount given orally to be absorbed in the circulation (only 5-10% is transported to blood). The second barrier is the blood-brain barrier that shows poor permeability to a large number of compounds including EDTA compounds. Control animals received the same volume of vehicle. Blood was collected through heart puncture on isofluorane-anaesthesized animals and allowed to clot for 5 minutes on ice. The serum was separated, snap chilled in liquid nitrogen and frozen at −80° C. till analyzed. Brainstems from all the animals were collected and processed for brain serotonin measurement through HPLC. Mice were observed for any physical or behavioral abnormality during the course of investigation.

Serotonin Measurements in Serum

The Serotonin ELISA kit obtained from the Fitzgerald company was used to measure derivatized serotonin from serum. Derivatization is part of the sample preparation. Serotonin present in the serum was first quantitatively acylated into N-Acylserotonin using the acylation reagent. The principle of the assay is based on competitive ELISA, wherein serotonin that is bound to the solid phase of the plate and the N-acylserotonin compete for the fixed number of antiserum binding sites. When the reaction is in equilibrium, free antigen and free antigen-antiserum complexes are removed by washing.

The antibody bound to the solid phase serotonin is then detected using antirabbit/peroxidase. The substrate TMB/Peroxidase reaction is read at 450 nm. The amount of antibody bound to the solid phase serotonin is inversely proportional to the concentration of serotonin in the sample.

Drugs Used in the Study

Catechol-3,6-bis methyleneiminodiacetic acid (CBMIDA) (basic structure is an EDTA-like compound and the catechol ring is at the centre) synthesized at the Columbia University Chemistry division, and para-chlorophenylalanine (pCPA) obtained from Sigma Aldrich Corp. were used. Each compound was dissolved with twice molar solution of $NaHCO_3$ in water and given to mouse orally at 250 and 500 mg/kg/dose.

The structure of pCPA is:

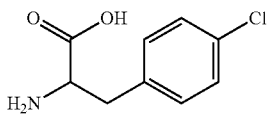

The structure of CBMIDA is:

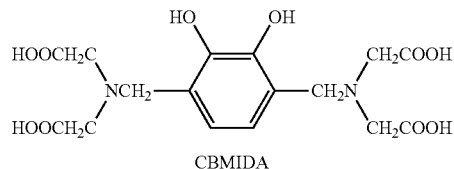

CBMIDA

Results

Figure 11:
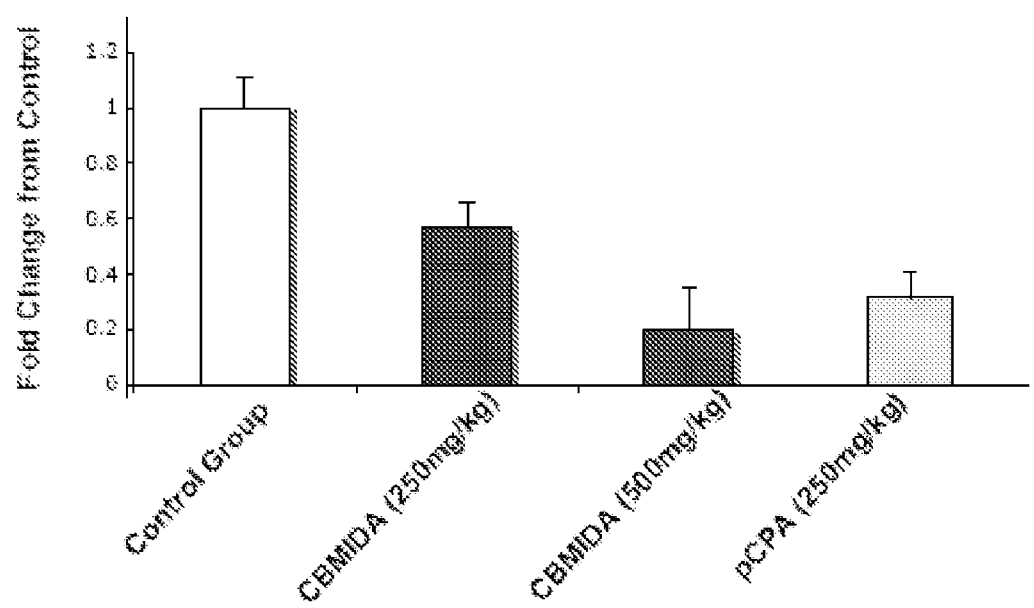
FIG. 11. Oral feeding of CBMIDA reduces peripheral serotonin.

As can be seen in FIG. 11, oral administration of CBMIDA decreased serotonin serum levels to 80% below normal at a dose of 500 mg/kg twice daily. Lowering this dose to 250 mg/kg produced the effect but to a lesser extent. In fact when one compares the two doses versus control animals, a dose response curve is produced. While pCPA, a well known inhibitor of tryptophan hydroxylase used as a control, decreased the serum serotonin levels as expected to >60% below normal range.

Example 2

Measurement of Serum Serotonin

Two possible methods of measuring serum serotonin levels are as follows:

(1) Initial steps are performed at room temperature using polypropylene tubes and pipettes. Establishing free flow by venipuncture, blood is collected from an antecubital vein with a 19-gauge, thin-walled butterfly needle into EDTA-containing vacuum tubes. The tubes are centrifuged (Sorvall GLC-2B) at 800 rpm (100×g) for 15 minutes at room temperature. The upper layer of platelet-rich plasma (PRP), about 0.3 cm from the interface layer (buffy coat), is removed with a plastic pipette and transferred to a new polypropylene test tube. The tube containing the platelet-poor plasma (PRP) is iced for 10 min before being centrifuged at 11,000 rpm (14,500×g) in a Sorvall SS-34 rotor for 6 min at 4° C. to yield the platelet pellet and platelet poor plasma (PPP). The supernate containing PPP is removed and placed into a new polypropylene test tube in a volume of 500 microliters in Eppendorf tubes. The platelet-rich pellets are resuspended in 1 ml saline. Mixing or vortexing, before transfer to an Eppendorf tube, is sometimes required to maintain a homogenous suspension without clumps. The aliquoted plasma supernate (PPP) and the resuspended pellet (PRP) are kept at −20. For the serotonin assay, the samples are resuspended in saline. The 'hormonal' element of serotonin that is of most interest is the circulating level in PPP but the PRP fraction will also be measured. The method is an ELISA obtained from Fitzgerald Industries International (Concord, Mass.). It measures the derivatized serotonin from serum or plasma samples or urine samples. Derivatization is part of the sample preparation. Serotonin present in the biological fluids (e.g., serum) is first quantitatively acylated using the acylation reagent into N-acylserotonin. The assay is based on the competitive ELISA principle wherein serotonin that is bound to the solid phase of the plate and the N-acylserotonin competes for the fixed number of antiserum binding sites. When the reaction is in equilibrium, free antigen and free antigen-antiserum complexes are removed by washing. The antibody bound to the solid phase serotonin is then detected by the anti-rabbit/peroxidase. The substrate TMB/Peroxidase reaction is read at 450 nm. The amount of antibody bound to the solid phase serotonin is inversely proportional to the concentration of serotonin in the sample. Although the ELISA assay is useful, we will have the opportunity to apply an even more precise assay namely HPLC coupled with electrochemical detection.

(2) Another method relies on HPLC coupled with electrochemical detection. Samples obtained in the manner described above are precipitated with 1N $HClO_4$ (1:1), diluted and aliquoted into HPLC vials containing 32.5 µl of 0.02 M acetic acid. The fractions are injected via a Gilson 223 XL autoinjector onto the column. 20 µl of the microdialysis sample are injected onto a 100×2 mm C18 Hypersil 3 µm column and separated with a mobile phase consisting of 4.1 g/l sodium acetate, 500 mg/l $Na_2$-EDTA, 50 mg/l heptane sulfonic acid, 4.5% methanol v/v, and 30 µl/l of triethylamine, pH 4.75 at a flow rate of 0.4 ml/min using a Shimadzu LC-10 AD pump. Serotonin is detected amperometrically at a glassy carbon electrode at 500 mV vs Ag/AgCl. The detection limit, 0.5 fmol serotonin per 20 µl sample or 10 pM, is well within the circulating concentrations of serotonin. Since serotonin measured in PPP is not bound to any appreciable degree by plasma proteins, these measurements can be regarded as equivalent to free serotonin levels.

Example 3

Generation of Mutant Animals and Animal Treatments

Generation of Lrp5−/− (Kato et al., 2002, J. Cell Biol. 157:303-314) β-catenin floxed/floxed (Glass et al., 2005, Dev. Cell 8:751-764), α1(I)collagen-cre transgenic (Dacquin et al., 2002, Dev. Dyn. 224:245-251) and Htt−/− (Ansorge et al., 2008, J. Neurosci. 28:199-207) mice were as described previously. Lrp5+/−;Htt+/− double heterozygous mice were generated by crossing Lrp5+/− and Htt+/− mice. Three week-old Wt or Lrp5−/− mice were administered pCPA on alternate days for 9 weeks by i.p. All animal protocols were approved by the Animal Care Committees of Columbia University.

Example 4

Morphometric Measurements

Static histomorphometry measurements were performed as previously described in accordance with standard nomenclature, using the Osteomeasure Analysis System (Osteometrics, Inc) (Ducy et al., 2000, Cell 100:197-207). Four to 9 animals were assigned per group.

Example 5

Cell Cultures

Calvaria osteoblasts were extracted by triple collagenase/trypsin digestion from 4 day-old CD1 pups and differentiated with ascorbic acid as previously described (Duey et al., 2000, Cell 100:197-207).

Example 6

Gene Expression Studies

Osteoblasts were treated in serum-free medium with vehicle or Serotonin (50 to 100 µM, Sigma) for 24 hr. Total RNA were extracted with Trizol (Invitrogen). cDNA were generated using the ABI Reverse transcriptase system and random hexanucleotide primers. Real-time PCR was performed using superarray primers on a Stratagene real time PCR cycler and Actin expression was used as endogenous control. Chromatin immunoprecipitation assays (ChIP) were performed by standard procedures using primary osteoblasts. Microarray analysis was performed as described previously (Glass et al., 2005, Dev. Cell 8:751-764).

Example 7

Biochemical Studies

Osteoblasts were treated in serum-free medium with vehicle or Serotonin (50 to 100 µM, Sigma) for 24 hr. Lysates from primary osteoblasts or crushed frozen bones were prepared in RIPA buffer in the presence of protease and phosphatase inhibitors. Twenty to 60 µg of proteins were separated by SDS-PAGE in reducing conditions and transferred on nitrocellulose membrane using standard protocols. Membranes were incubated with primary antibodies including total or anti-Phospho CREB (Cell Signaling Technology).

Example 8

Hormone Measurements

Serotonin serum levels were quantified using immunoassay kits from Fitzgerald (Serotonin) and serotonin levels in the different regions of the brain were quantified by HPLC method as described previously (Mann et al., 1992, Arch. Gen. Psychiatry 49:442-446).

Example 9

Synthesis of Methyl 2-(4-(2-amino-6-(2,2,2-trifluoro-1-(3'-fluorobiphenyl-4-yl)ethoxy)pyrimidin-4-yl)phenylamino)-2-oxoacetate (Scheme 1)

4-chloro-6-(2,2,2-trifluoro-1-(3'-fluorobiphenyl-4-yl) ethoxy)pyrimidin-2-amine (320 mg, 0.806 mmol), methyl 2-oxo-2-(4-(4,4,5,5-tetramethyl-1,3,2-dioxaborolan-2-yl) phenylamino)acetate (320 mg, 0.95 mmol), dichlorobis (triphenylphosphine)palladium (79 mg, 0.11 mmol), and $Na_2CO_3$ (212 mg, 2.0 mmol) were added to a mixture of ethanol (10 mL) and water (10 mL) in a round-bottom flask. The flask was heated to reflux for 8 hours. The reaction mixture was cooled and solvent was removed. The residue was dissolved in 10 mL of 0.5 M NaOH solution, filtered, and the filtration was extracted with EtOAc. The organic portion was dried and the solvent was removed to get 250 mg of the above-named compound. $^1$H NMR (300 MHz, $CD_3OD$): δ δ 7.90 (m, 2H), 7.77 (s, 3H), 7.60 (m, 2H), 7.44 (m, 2H), 7.22 (m, 1H), 7.10 (m, 1H), 7.05 (s, 1H), 6.83 (m, 1H), 5.09 (m, 1H), 3.67 (s, 3H); M+1=541.

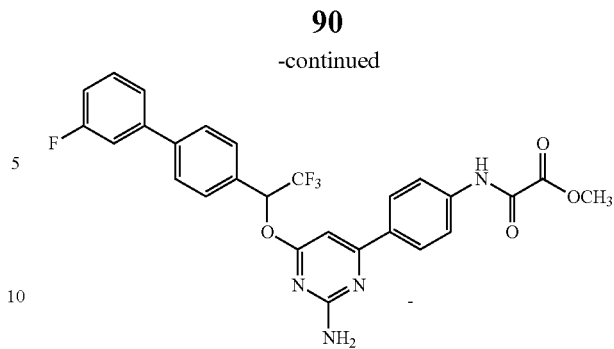

Example 10

Synthesis of (2S)-2-amino-3-(4-(2-amino-6-(2,2,2-trifluoro-1-(3'-fluorobiphenyl-4-yl)ethoxy)pyrimidin-4-yl)phenoxy)propanoic acid (Scheme 2)

4-chloro-6-(2,2,2-trifluoro-1-(3'-fluorobiphenyl-4-yl) ethoxy)pyrimidin-2-amine (80 mg, 0.20 mmol), (S)-methyl 3-(4-(4,4,5,5-tetramethyl-1,3,2-dioxaborolan-2-yl)phenoxy)-2-(tritylamino)propanoate (113 mg, 0.20 mmol), dichlorobis(triphenylphosphine)palladium (2 mg, 0.03 mmol), and $Na_2CO_3$ (42 mg, 0.40 mmol) were added to a mixture of ethanol (5 mL) and water (5 mL) in a round-bottom flask. The flask was heated to reflux for 8 hours. The reaction mixture was cooled and solvent was removed. The residue was purified by chromatography to get (2S)-methyl 3-(4-(2-amino-6-(2,2,2-trifluoro-1-(3'-fluorobiphenyl-4-yl) ethoxy)pyrimidin-4-yl)phenoxy)-2-(tritylamino)propanoate, which was deprotected by TFA and LiOH respectively to afford 50 mg of (2S)-2-amino-3-(4-(2-amino-6-(2,2,2-trifluoro-1-(3'-fluorobiphenyl-4-yl)ethoxy)pyrimidin-4-yl)phenoxy)propanoic acid as the HCl salt. $^1$H NMR (300 MHz, $CD_3OD$): δ 7.95 (m, 2H), 7.71 (s, 3H), 7.61 (m, 2H), 7.48 (m, 2H), 7.26 (m, 1H), 7.11 (m, 1H), 7.01 (s, 1H), 6.78 (m, 1H), 4.65 (m, 1H), 4.40-4.55 (m, 3H); M+1=543.

Scheme 1

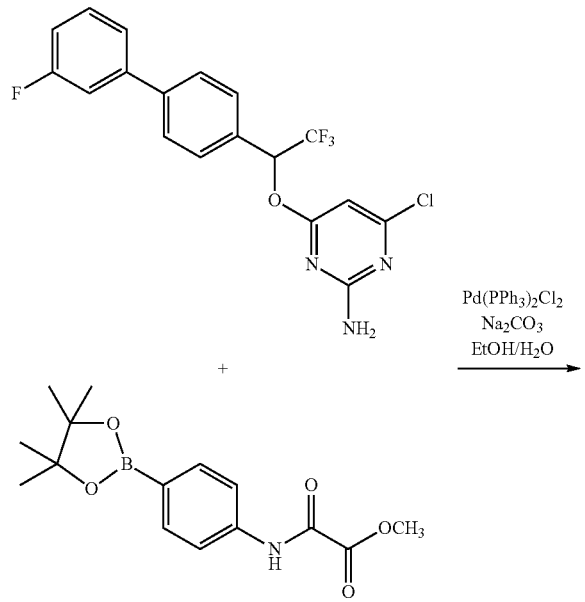

Scheme 2

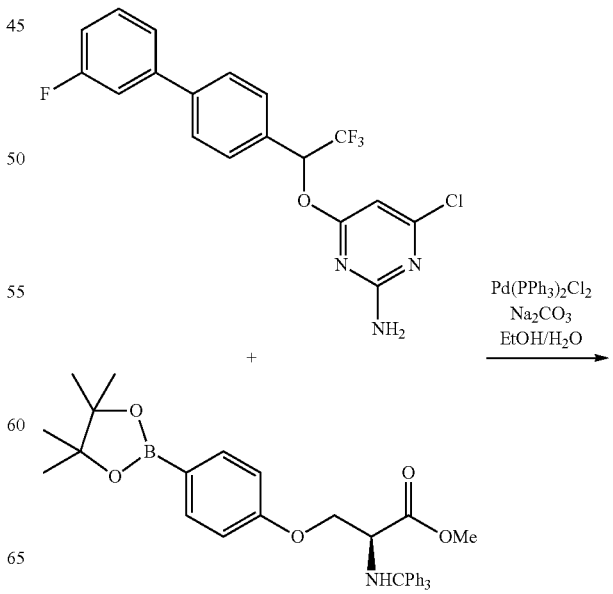

-continued

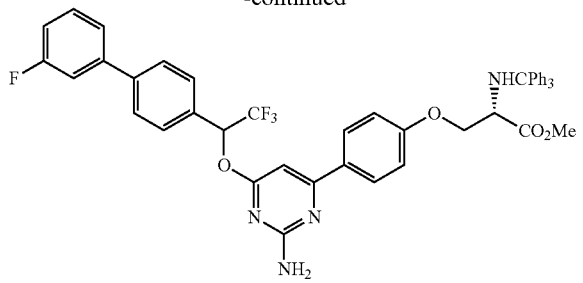

Example 11

The following three compounds were tested for their ability to effect peripheral serotonin levels in wild-type mice:

(1) Methyl 2-(4-(2-amino-6-(2,2,2-trifluoro-1-(3'-fluorobiphenyl-4-yl)ethoxy)pyrimidin-4-yl)phenylamino)-2-oxoacetate (the compound of Example 9)

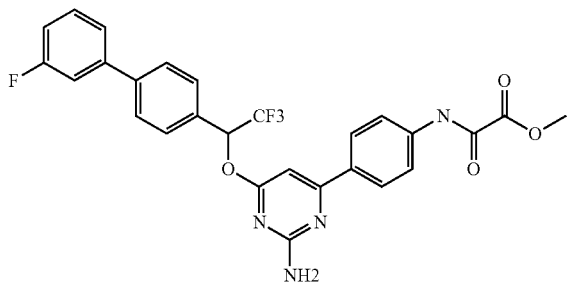 [SMILES: COC(=O)C(=O)Nc1ccc(-c2cc(OC(c3ccc(-c4cccc(F)c4)cc3)C(F)(F)F)nc(N)n2)cc1]

(2) (2S)-2-amino-3-(4-(2-amino-6-(2,2,2-trifluoro-1-(3'-fluorobiphenyl-4-yl)ethoxy)pyrimidin-4-yl)phenoxy)propanoic acid (the compound of Example 10)

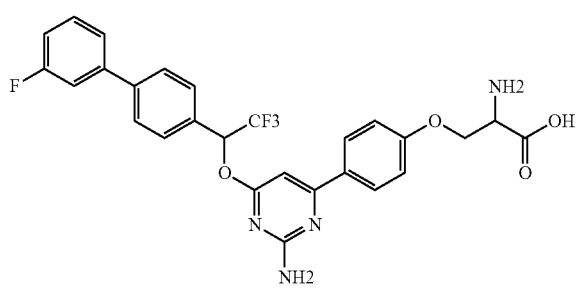 [SMILES: Nc1nc(OC(c2ccc(-c3cccc(F)c3)cc2)C(F)(F)F)cc(-c2ccc(OCC(N)C(=O)O)cc2)n1]

(3) (2S)-2-amino-3-(4-(2-amino-6-(2,2,2-trifluoro-1-(3'-fluorobiphenyl-4-yl)ethoxy)pyrimidin-4-yl)phenyl)propanoic acid (LP-533401)

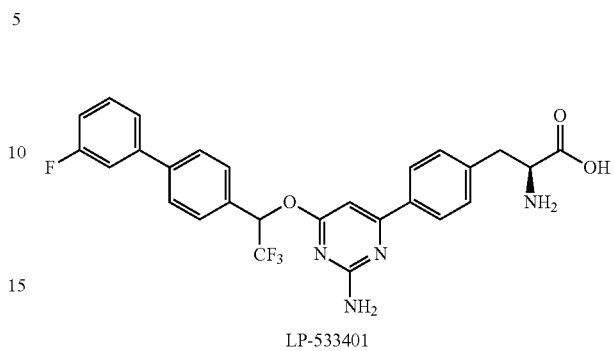

LP-533401

Also tested as a negative control was vehicle alone. Each compound as well as vehicle was administered to 5 mice and the resulting peripheral serotonin levels were as follows:

TABLE 4

| Compound | Peripheral serotonin (ng/ml) (mean ± SEM) |
|---|---|
| Vehicle | 541 ± 47.64 |
| LP-533401 | 88.56 ± 12.93 |
| Methyl 2-(4-(2-amino-6-(2,2,2-trifluoro-1-(3'-fluorobiphenyl-4-yl)ethoxy)pyrimidin-4-yl)phenylamino)-2-oxoacetate | 23.76 ± 8.25 |
| (2S)-2-amino-3-(4-(2-amino-6-(2,2,2-trifluoro-1-(3'-fluorobiphenyl-4-yl)ethoxy)pyrimidin-4-yl)phenoxy)propanoic acid | 93.77 ± 12.15 |

Figure 13:
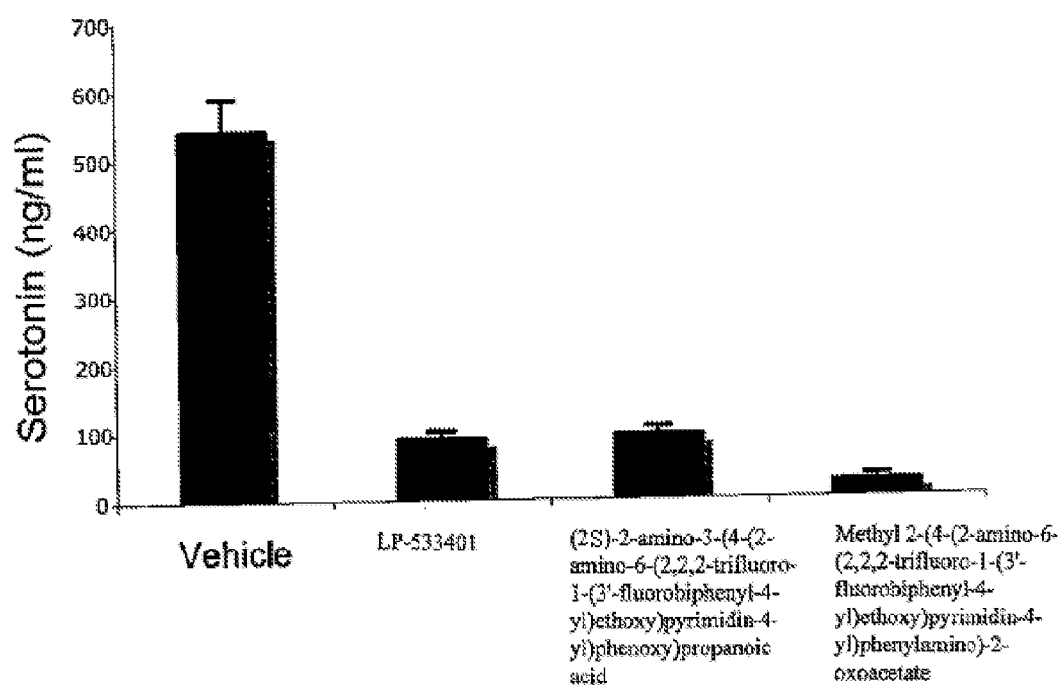
FIG. 13. Effect of LP-533401; Methyl 2-(4-(2-amino-6-(2,2,2-trifluoro-1-(3'-fluorobiphenyl-4-yl)ethoxy)pyrimidin-4-yl)phenylamino)-2-oxoacetate; and (2S)-2-amino-3-(4-(2-amino-6-(2,2,2-trifluoro-1-(3'-fluorobiphenyl-4-yl)ethoxy)pyrimidin-4-yl)phenoxy)propanoic acid on peripheral serotonin levels in wild-type mice.

The results can also be seen in FIG. 13.

Example 12

In Vitro TPH1 Inhibition Assays

The rat mastocytoma cell line RBL-2H3, which endogenously expresses TPH1 was obtained from The American Type Culture Collection (ATCC). The cells were seeded at 15,000 cells/well in a 48-well plate in complete medium. Cells were treated with LP-533,401 at various concentrations for 3 days. At the end of the treatment, cells were washed in PBS and lysed for the analysis of serotonin content.

Example 13

Preventive and Curative Experimental Regimen in Mice

Six-week-old wild-type virgin female mice were purchased from the Jackson Laboratories and subjected to either bilateral ovariectomy or a sham operation after a few days of acclimatization to the animal facility post-arrival. Ovariectomy was performed under isofluorane anesthesia through dorsal, subrenal incision. In the first experiment, mice were treated from day 1 post-ovariectomy for 4 weeks with LP-533,401 (1, 10, 100 or 250 mg/kg/day) or vehicle. In the second experiment, mice were treated for 4 weeks from 2 to 6-weeks post-ovariectomy with LP-533,401 (250 mg/kg/day) or vehicle. In the third set of experiments, mice were treated for 6 weeks from 6 to 12-weeks post-ovariectomy with LP-533,401 (250 mg/kg/day) or vehicle. LP-533,401 was dissolved in polyethylene glycol:5% dextrose (40:60) and given daily by gavage at the doses indicated. Animals were observed daily for any behavioral abnormalities. Mice were sacrificed at the end of the experimental regimen and processed for the skeletal and physiological analysis.

Example 14

Curative Experimental Regimen in Rats

Virgin female Sprague-Dawley rats (National Institute of Nutrition, Hyderabad, India) were obtained at 3 months of age and allowed to acclimate to the facility for 1 week before study initiation and surgical procedures. They were housed under a 12 hour:12 hour light:dark cycle and provided throughout the study with water and PMI (Purina Mills, Incorporated) Certified Rodent Laboratory Chow. Rats were subjected to either bilateral ovariectomy or a sham operation under isoflurane anesthesia. To maintain a comparable body weight between groups, rats were paired-fed post-ovariectomy. The rats were divided into two groups of sham-operated and ovariectomized animals and left untreated for 3 weeks to allow bone loss to occur. One group of sham and one group of ovariectomized rats (n=10/group) were killed as baseline controls to determine bone loss before the start of LP-533,401 or PTH administration. The remaining animals (n=5-10/group) received vehicle or LP-533,401 (250 mg/kg/day) by gavage, or recombinant human PTH (80 ug/kg) by daily subcutaneous (s.c.) injection for 4 weeks. The 80 ug/kg dose of PTH was selected as being optimal for reversal of ovariectomy-induced bone loss in rats based on previous studies, while the dose of LP-533,401 was selected based on the effective dose for bone loss-reversal observed in mice experiments. To label bone-forming surfaces, animals were injected s.c. with calcein (8 mg/kg) at 10 and 3 days before death. Animals were killed by an overdose of Isofluorane anesthesia. The right tibia and lumbar vertebra 2 (L2) were collected, cleaned of excess soft tissue, fixed overnight in 10% formalin and processed for μCT or histomorphometric analysis. The right femur and L3 were cleaned of excess tissue and stored at −20° C. prior to biomechanical testing.

Example 15

Bone Histomorphometric Analyses

Bone histomorphometry was performed as previously described (Duey et al., 2000, Cell 100:197-207; Takeda et al., 2002, Cell 111:305-317; Parfitt et al., 1987, J. Bone Miner. Res. 2:595-610). Briefly, lumbar vertebrae were dissected, fixed for 24 hr in 10% formalin, dehydrated in graded ethanol series, and embedded in methyl methacrylate resin according to standard protocols (Parfitt et al., 1987, J. Bone Miner. Res. 2:595-610). Von Kossa/Von Gieson staining was performed using 7 μm sections for bone volume over tissue volume (BV/TV) measurement. Bone formation rate (BFR) was analyzed by the calcein double-labeling method (Ducy et al., 2000, Cell 100:197-207). Calcein (Sigma Chemical Co., St. Louis, Mo.) was dissolved in calcein buffer (0.15 M NaCl, 2% $NaHCO_3$) and injected twice at 0.125 mg/g body weight on day 1 and 4, and then mice were killed on day 6. Unstained 4 μm sections were used for bone formation rate (BFR) measurements. For the analysis of parameters of osteoblasts and osteoclasts, 4 μm sections were stained with toluidine blue and tartrate-resistant acid phosphatase (TRAP), respectively (2). Histomorphometric analyses were performed using the Osteomeasure Analysis System (Osteometrics, Atlanta, Ga.).

Example 16

μCT Analysis

Trabecular bone architecture of proximal tibia was assessed using a micro computed tomography (μCT) system (VivaCT 40, SCANCO Medical AG, Bassersdorf, Switzerland). Tibia bone specimen was stabilized with gauze in a 2 ml centrifuge tube filled with 70% ethanol and fastened in the specimen holder of the μCT scanner. One hundred μCT slices, corresponding to a 1.05 mm region distal from the growth plate, were acquired at an isotropic spatial resolution of 10.5 μm. A global thresholding technique was applied to binarize gray-scale μCT images where the minimum between the bone and bone marrow peaks in the voxel gray value histogram was chosen as the threshold value. The trabecular bone compartment was segmented by a semi-automatic contouring method and subjected to a model-independent morphological analysis (Hildebrand et al., 1999, J. Bone Miner. Res. 14:1167-1174) by the standard software provided by the manufacture of the μCT scanner. 3D morphological parameters, including model independent measures by distance transformation (DT) of bone volume fraction (BV/TV), Tb.Th* (trabecular thickness), Tb.N* (trabecular number), Tb.Sp* (trabecular separation) and connectivity density (Conn.D) were evaluated. The Conn.D is a quantitative description of the trabecular connection (Feldkamp et al., 1989, J. Bone Miner. Res. 4:3-11; Gundersen et al., 1993, Bone 14:217-222).

Example 17

Biochemistry

Blood samples were collected from mice and rats through cardiac puncture under isoflurane anesthesia, kept on ice for 5 min, and centrifuged at 13,000 rpm for 10 min at 4° C. Serum samples were stored at −80° C. until hormonal analyses were performed. Serum serotonin levels were quantified by ELISA (Serotonin kit, Fitzgerald) while serotonin levels in brain regions were quantified by HPLC as described previously (Mann et al., 1992, Arch. Gen. Psychiatry 49:442-446). Serum levels of total deoxypyridinoline (DPD) cross-links was measured using the Merta tDPD kit (Quidel corp. Sandiago, Calif.) and Osteocalcin using Rat and Mouse Ocn IRMA kit.

Example 18

Biomechanical Testing

The mechanical properties of right femur and the 3rd lumbar vertebrae (LVB) were determined using three-point bending and axial unconfined compression, respectively. To achieve parallel ends, vertebrae were mounted on a custom-designed jig and cut using a low-speed diamond saw with a double-blade (Isomet, Buehler, Lake Bluff, Ill., USA). On the day of testing, the sample was equilibrated to room temperature in PBS for an hour, and then mounted on a hydraulic test system for mechanical loading (Instron, Norwood, Mass., USA). The loading protocol included a 5 N pre-load for 3 minutes, which was followed by continuous load at 0.005 mm/s until failure. The displacement and mechanical load were recorded and the data were processed to determine the ultimate load (N) and stiffness (N/mm) of each femur and vertebra, respectively.

Example 19

Statistical Analyses

Statistical significance was assessed by Student's t test or a one way ANOVA followed by Newman-Keuls test for comparison between more than 2 groups. $P<0.05$ was considered significant. Different letters indicate significant differences among groups.

What is claimed is:

1. The compound

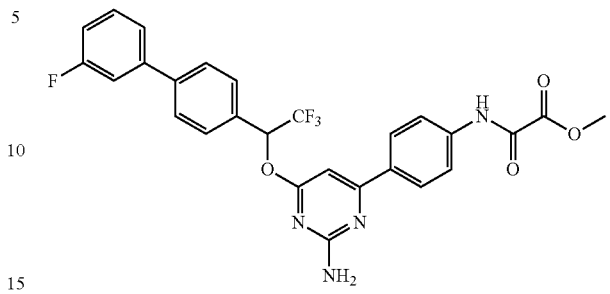

or a pharmaceutically acceptable salt thereof.

2. A pharmaceutical composition comprising a therapeutically effective amount of the compound or a pharmaceutically acceptable salt thereof of claim 1 and at least one pharmaceutically acceptable excipient.

3. A method of treating osteoporosis in a patient in need thereof, comprising administering to said patient a pharmaceutically effective amount of the compound of claim 1.

4. A method of treating renal osteodystrophy or bone metastasis in patient in need thereof comprising administering to the patient a pharmaceutically effective amount of the compound of claim 1.

* * * * *